(12) United States Patent
Crowe et al.

(10) Patent No.: US 9,040,262 B2
(45) Date of Patent: May 26, 2015

(54) BIOCATALYSTS FOR EZETIMIBE SYNTHESIS

(75) Inventors: Michael Crowe, Singapore (SG); Oscar Alvizo, Fremont, CA (US); Behnaz Behrouzian, Sunnyvale, CA (US); Yong Koy Bong, Singapore (SG); Steven J. Collier, Singapore (SG); Anupam Gohel, Singapore (SG); Jagadeesh Mavinahalli, Singapore (SG); Naga Modukuru, Singapore (SG); Emily Mundorff, Poughkeepsie, NY (US); Derek Smith, Singapore (SG); Shiwei Song, Singapore (SG); Wan Lin Yeo, Singapore (SG)

(73) Assignee: Codexis, Inc., Redwood City, CA (US)

( * ) Notice: Subject to any disclaimer, the term of this patent is extended or adjusted under 35 U.S.C. 154(b) by 327 days.

(21) Appl. No.: 13/695,856

(22) PCT Filed: May 4, 2011

(86) PCT No.: PCT/US2011/035194
§ 371 (c)(1),
(2), (4) Date: Nov. 2, 2012

(87) PCT Pub. No.: WO2011/140219
PCT Pub. Date: Nov. 10, 2011

(65) Prior Publication Data
US 2013/0052699 A1 Feb. 28, 2013

Related U.S. Application Data

(60) Provisional application No. 61/331,245, filed on May 4, 2010.

(51) Int. Cl.
| | | |
|---|---|---|
| C12P 17/10 | (2006.01) | |
| C12N 9/04 | (2006.01) | |
| C12N 1/15 | (2006.01) | |
| C07H 21/04 | (2006.01) | |
| C07K 14/47 | (2006.01) | |
| C12P 17/14 | (2006.01) | |
| A61K 38/00 | (2006.01) | |

(52) U.S. Cl.
CPC .............. *C07K 14/47* (2013.01); *C12N 9/0006* (2013.01); *C12P 17/14* (2013.01); *A61K 38/00* (2013.01)

(58) Field of Classification Search
CPC ....... C12P 17/10; C12P 17/14; C12N 9/0004; C07K 14/47
USPC ....................... 435/121, 189, 320.1
See application file for complete search history.

(56) References Cited

U.S. PATENT DOCUMENTS

| | | |
|---|---|---|
| 5,064,761 A | 11/1991 | Schneider et al. |
| 5,200,335 A | 4/1993 | Hummel et al. |
| 5,225,339 A | 7/1993 | Wong et al. |
| 5,342,767 A | 8/1994 | Wong et al. |
| 5,385,833 A | 1/1995 | Bradshaw et al. |
| 5,427,933 A | 6/1995 | Chen et al. |
| 5,491,077 A | 2/1996 | Chartrain et al. |
| 5,538,867 A | 7/1996 | Durliat et al. |
| 5,559,030 A | 9/1996 | Matsuyama et al. |
| 5,618,707 A | 4/1997 | Homann et al. |
| 5,700,670 A | 12/1997 | Yamagishi et al. |
| 5,712,388 A | 1/1998 | Matsumoto et al. |
| 5,739,321 A | 4/1998 | Wu et al. |
| 5,767,115 A | 6/1998 | Rosenblum et al. |
| 5,891,685 A | 4/1999 | Yamagishi et al. |
| 5,891,703 A | 4/1999 | Van Der Laan et al. |
| 6,033,823 A | 3/2000 | Van Der Laan et al. |
| 6,037,158 A | 3/2000 | Hummel et al. |
| 6,117,679 A | 9/2000 | Stemmer |
| 6,133,001 A | 10/2000 | Homann et al. |
| 6,207,822 B1 | 3/2001 | Thiruvengadam et al. |
| 6,225,099 B1 | 5/2001 | Hummel et al. |
| 6,376,246 B1 | 4/2002 | Crameri et al. |
| 6,399,339 B1 | 6/2002 | Wolberg et al. |
| 6,413,750 B1 | 7/2002 | Hummel et al. |
| 6,495,023 B1 | 12/2002 | Zeikus et al. |
| 6,586,182 B1 | 7/2003 | Patten et al. |
| 6,627,757 B2 | 9/2003 | Fu et al. |
| 6,645,746 B1 | 11/2003 | Kizaki et al. |
| 6,800,477 B2 | 10/2004 | Patel et al. |
| 7,067,675 B2 | 6/2006 | Reddy et al. |
| 7,083,962 B2 | 8/2006 | Kimoto et al. |
| 8,288,141 B2 | 10/2012 | Savile et al. |
| 2002/0061564 A1 | 5/2002 | Rozzell |
| 2003/0054520 A1 | 3/2003 | Bommanus et al. |
| 2003/0068811 A1 | 4/2003 | Patel et al. |

(Continued)

FOREIGN PATENT DOCUMENTS

| | | |
|---|---|---|
| EP | 0369691 B1 | 7/1994 |
| EP | 1013758 A1 | 6/2000 |

(Continued)

OTHER PUBLICATIONS

Geneseq Accession No. AXW52051 dated Apr. 29, 2010.
Geneseq Accession No. AXW52079 dated Apr. 29, 2010.
Geneseq Accession No. AWI71982 dated May 14, 2009.
Amidjojo et al., 2005, "Asymmetric Synthesis of Tert-butyl (3R, 5S)6-chloro-dihydroxyhexanoate with *Lactobacillus kefir*," Appl Microbiol Biotechnol., 69:9-15.
Baerga-Ortiz et al., 2006, "Directed Mutagenesis Alters the Stereochemistry of Catalysis by Isolated Ketoreductase Domains from the Erythromycin Polyketide Synthase," Chem Biol., 13(3):277-85.
Bisel et al., 2007, "Stereochemical clarification of the enzyme-catalysed reduction of 2-acetylchromen-4-one," Tetrahedron Asymmetry, 18(9):1142-1144.

(Continued)

*Primary Examiner* — Tekchand Saidha
*Assistant Examiner* — Md. Younus Meah
(74) *Attorney, Agent, or Firm* — Codexis, Inc.

(57) ABSTRACT

The present disclosure relates to non-naturally occurring polypeptides useful for preparing Ezetimibe, polynucleotides encoding the polypeptides, and methods of using the polypeptides.

10 Claims, No Drawings

(56) References Cited

U.S. PATENT DOCUMENTS

| | | | |
|---|---|---|---|
| 2004/0214297 | A1 | 10/2004 | Davis et al. |
| 2004/0265978 | A1 | 12/2004 | Gupta et al. |
| 2005/0095619 | A1 | 5/2005 | Davis et al. |
| 2005/0124029 | A1 | 6/2005 | Van Der Laan et al. |
| 2006/0195947 | A1 | 8/2006 | Davis et al. |
| 2006/0286646 | A1 | 12/2006 | Patel et al. |
| 2007/0083055 | A1 | 4/2007 | Sturmer et al. |
| 2007/0243594 | A1 | 10/2007 | Gupta et al. |
| 2008/0220990 | A1 | 9/2008 | Fox |
| 2008/0248539 | A1 | 10/2008 | Giver et al. |
| 2008/0318295 | A1 | 12/2008 | Ching et al. |
| 2009/0093031 | A1 | 4/2009 | Liang et al. |
| 2009/0104671 | A1 | 4/2009 | Yasohara et al. |
| 2009/0155863 | A1 | 6/2009 | Liang et al. |
| 2009/0162909 | A1 | 6/2009 | Campopiano et al. |
| 2009/0191605 | A1 | 7/2009 | Liang et al. |
| 2009/0311762 | A1 | 12/2009 | Tschentscher et al. |
| 2009/0312196 | A1 | 12/2009 | Colbeck et al. |
| 2010/0055751 | A1 | 3/2010 | Voladri et al. |
| 2010/0062499 | A1 | 3/2010 | Mundorff et al. |
| 2010/0151534 | A1 | 6/2010 | Savile et al. |

FOREIGN PATENT DOCUMENTS

| | | |
|---|---|---|
| EP | 1176203 A1 | 1/2002 |
| EP | 1179595 A1 | 2/2002 |
| EP | 1908845 A1 | 4/2008 |
| WO | 95/22625 A1 | 8/1995 |
| WO | 97/20078 A1 | 6/1997 |
| WO | 97/35966 A1 | 10/1997 |
| WO | 98/27230 A1 | 6/1998 |
| WO | 00/42651 A2 | 7/2000 |
| WO | 01/40450 A1 | 6/2001 |
| WO | 01/75767 A2 | 10/2001 |
| WO | 02/086126 A2 | 10/2002 |
| WO | 2005/017135 A1 | 2/2005 |
| WO | 2005/018579 A2 | 3/2005 |
| WO | 2005/033094 A2 | 4/2005 |
| WO | 2005/054491 A1 | 6/2005 |
| WO | 2007/010944 A1 | 1/2007 |
| WO | 2007/012428 A1 | 2/2007 |
| WO | 2008/042876 A2 | 4/2008 |
| WO | 2008/085300 A1 | 7/2008 |
| WO | 2008/103248 A1 | 8/2008 |
| WO | 2008/151324 A1 | 12/2008 |
| WO | 2009/036404 A2 | 3/2009 |
| WO | 2010/025085 A2 | 3/2010 |
| WO | 2010/025238 A2 | 3/2010 |
| WO | 2010/113175 A2 | 10/2010 |
| WO | 2011/022548 A2 | 2/2011 |

OTHER PUBLICATIONS

Bradshaw et al., 1992, "*Lactobacillus kefir* Alcohol Dehydrogenase: A Useful Catalyst for Synthesis," J. Org. Chem., 57(5):1532-1536.

Breyer-Pfaff et al., 1999, "High-affinity Stereoselective Reduction of the Enantiomers of Ketotifen and of Ketonic Nortriptyline Metabolites by Aldo-Keto Reductases from Human Liver," Biochem. Pharmacol., 59:249-260.

Cha et al., 2002, "Stereochemical control in diastereoselective reduction of α-substituted-β-ketoesters using a reductase purified from *Kluyveromyces marxianus*," Biotechnol. Lett., 24:1695-1698.

Daussmann et al., 2006, "Oxidoreductases and Hydroxynitrilase Lyases: Complementary Enzymatic Technologies for Chiral Alcohols," Eng Life Sci., 6(2):125-129.

Fuganti et al., 1993, "Microbial Generation of (2R,3S)- and (2S,3S)-Ethyl 2-Benzamidomethyl-3-hydroxybutyrate, a Key Intermediate in the Synthesis of (3S,1'R)-3-(1'-Hydroxyethyl)azetidin-2-one," J Chem. Soc. Perkin Trans., 1:2247-2249.

Genbank Accession No. 1NXQ_A dated Sep. 24, 2008.
Genbank Accession No. AB036927 dated Feb. 2, 2001.
Genbank Accession No. ABJ63353.1 dated Mar. 5, 2010.
Genbank Accession No. AJ544275 dated Feb. 5, 2010.
Genbank Accession No. AAN73270 dated Nov. 3, 2003.
Genbank Accession No. AAP94029 dated Apr. 1, 2004.
Genbank Accession No. AF160799 dated Dec. 9, 1999.
Genbank Accession No. BAA24528.1 dated Jan. 28, 1998.
Genbank Accession No. CAD66648 dated Feb. 5, 2010.
Genbank Accession No. CP00046 dated Mar. 5, 2010.
Genbank Accession No. JC7338 dated Jun. 3, 2002.
Genbank Accession No. NO011476 dated May 17, 2010.
Genbank Accession No. NP010656.1 dated May 17, 2010.
Genbank Accession No. NP010159.1 dated May 17, 2010.
Genbank Accession No. NP014490.1 dated May 17, 2010.
Genbank Accession No. NP631415.1 dated Mar. 30, 2010.
Genbank Accession No. P41747 dated Apr. 20, 2010.
Genbank Accession No. Q07551 dated Apr. 20, 2010.
Genbank Accession No. Q9UUN9 dated Mar. 2, 2010.
Genbank Accession No. X64841.1 dated Jan. 8, 1997.
Genbank Accession No. ZP00318704.1 dated Jun. 17, 2004.
Genbank Accession No. ZP00202558.1dated Oct. 4, 2004.

Goldberg et al., 2007, "Biocatalytic ketone reduction-a powerful tool for the production of chiral alcohols-part I: processes with isolated enzymes," Appl Microbiol Biotechnol, 76(2):237-248.

Gröger et al., 2004, "Preparative asymmetric reduction of ketones in a biphasic medium with an (S)-alcohol dehydrogenase under in situ-cofactor-recycling with a formate dehydrogenase," Tetrahedron, 60:633-640.

Hönig et al., 1994, "Enzymatic Resolutions of Heterocyclic Alcohols," Biocatalysis, 9:61-69.

Hummel et al., 1989, "Dehydrogenases for the synthesis of chiral compounds," Eur. J. Biochem., 184:1-13.

Hummel, 1990, "Reduction of acetophenone to R(+)-phenylethanol by a new alcohol dehydrogenase from *Lactobacillus kefir*," Appl Microbiol Biotechnol, 34(1): 15-19.

Hummel, 1999, "Large-scale applications of NAD(P)-dependent oxidoreductases: recent developments," Trends Biotechnol., 17(12):487-492.

Jörnvall et al., 1995, "Short-chain dehydrogenase/reductases (SDR)," Biochemistry, 34(18):6003-6013.

Kallberg et al., 2002, "Short-chain dehydrogenase/reductase (SDR) relationships: A large family with eight clusters common to human, animal, and plant genomes," Protein Sci., 11(3):636-641.

Kallberg et al., 2002, "Short-chain dehydrogenases/reductases (SDRs) Coenzyme-based functional assignments in completed genomes," Eur. J. Biochem., 269:4409-4417.

Kaluzna et al., 2005, "Ketoreductases: stereoselective catalysts for the facile synthesis of chiral alcohols," Tetrahedron: Asymmetry, 16: 3682-3689.

Kataoka et al., 2003, "Novel bioreduction system for the production of chiral alcohols," Appl Microbiol Biotechnol., 62:437-445.

Nakamura et al. 2003, "Recent developments in asymmetric reduction of ketones with biocatalysts," Tetrahedron: Asymmetry, 14: 2659-2681.

Neifind et al., 2000, "Crystallization and preliminary characterization of crystals of R-alcohol dehydrogenase from *Lactobacillus brevis*," Acta Crystallogr. D. Biol. Crystallogr., 56:1696-1698.

Niefind et al., 2003, "The Crystal Structure of R-specific Alcohol Dehydrogenase from *Lactobacillus brevis* Suggests the Structural Basis of its Metal Dependency," J Mol Bio., 327(2):317-28.

Petrash et al., 2001, "Functional Genomic Studies of Aldo-keto Reductases," Chem Biol Interact., 130-132 (1-3):673-83.

Rodrigues et al., 2004, "Recent Advances in the Biocatalytic Asymmetric Reduction of Acetophenones and α,β-Unsaturated Carbonyl Compounds," Food Technol. Biotechnol., 42 (4) 295-303.

Santaniello et al., 1984, "Chiral Synthesis of a Component of *Amanita muscaria*, (−)-4-hydroxypyrrolidin-2-one, and Assessment of its Absolute Configuration," J. Chem. Res., Synop., 132-133.

Schlieben et al., 2005, "Atomic Resolution Structures of R-specific Alcohol Dehydrogenase from *Lactobacillus brevis* Provide the Structural Bases of its Substrate and Cosubstrate Specificity," J. Mol. Biol., 349(4):801-13.

(56) References Cited

OTHER PUBLICATIONS

Stemmer et al., 1994, "DNA shuffling by random fragmentation and reassembly: in vitro recombination for molecular evolution," Prod. Natl. Acad. Sci.USA, 91:10747-10751.

Sulzenbacher et al., 2004, "Crystal Structure of *E. coli* Alcohol Dehydrogenase YqhD: Evidence of a Covalently Modified NADP Coenzyme," Journal Mol. Biol., 342:489-502.

Temino et al., 2005, "Entrapment of the alcohol dehydrogenase from *Lactobacillus kefir* in polyvinyl alcohol for the synthesis of chiral hydrophobic alcohols in organic solvents," Enzyme Microb. Technol., 36(1):3-9.

Weckbecker et al., 2006, "Cloning, expression, and characterization of an (R)-specific alcohol dehydrogenase from *Lactobacillus kefir*," Biocatal. Biotransform., 24(5):380-389.

Wolberg et al., 2000, "Highly Regio- and Enantioselective Reduction of 3,5-Dioxocarboxylates," Angew Chem. Int. Ed. Engl., 39(23):4306-4308.

Wolberg, 2001, "Enzymatic Reduction of Hydrophobic beta, delta-Diketo Esters," Synthesis, 937-942.

Xie et al., 2006, "Asymmetric Reduction of o-Chloroacetophenone with *Candida* pseudotropicalis 104," Biotechnol. Prog. 22:1301-1304.

Zhao et al., 1999, "Molecular evolution by staggered extension process (StEP) in vitro recombination," Nature Biotech., 16:258.

Zhu et al., 2005, "Evaluation of substituent effects on activity and enantioselectivity in the enzymatic reduction of aryl ketones," Tetrahedron Asymm., 16:1541-1546.

Disclosed Anonymously, "Preperation of 1-(4-fluorophenyl)-3(R)-[3-(4-fluorophenyl)-3(S)-hydroxypropyl]-4(S)-(4-hydroxyphenyl)-2-azetidinone," from IP.com, Prior Art Database, IP.com No. IPCOM000206875D [May 12, 2011].

BIOCATALYSTS FOR EZETIMIBE SYNTHESIS

CROSS REFERENCE TO RELATED APPLICATIONS

The present application is a national stage application filed under 35 USC §371 and claims priority of the international application PCT/US2011/035194, filed May 4, 2011, and U.S. provisional patent application 61/331,245, filed May 4, 2010, each of which is hereby incorporated by reference herein.

1. TECHNICAL FIELD

The present disclosure relates to biocatalysts and methods of using the biocatalysts.

2. REFERENCE TO SEQUENCE LISTING, TABLE OR COMPUTER PROGRAM

The Sequence Listing is concurrently submitted herewith the specification as an ASCII formatted text file via EFS-Web with a file name of CX2-037USP1_ST25.txt with a creation date of May 3, 2010, and a size of 281 kilobytes. The Sequence Listing filed via EFS-Web is part of the specification and is hereby incorporated in its entirety by reference herein.

3. BACKGROUND

The present disclosure relates to improved biocatalysts and improved biocatalytic processes for the preparation of the active pharmaceutical ingredient, (1-(4-fluorophenyl)-3(R)-[3-(4-fluorophenyl)-3(S)-hydroxypropyl]-4(S)-(4-hydroxyphenyl)-2-azetidinone) (shown below as compound (1)) and derivatives and analogs thereof.

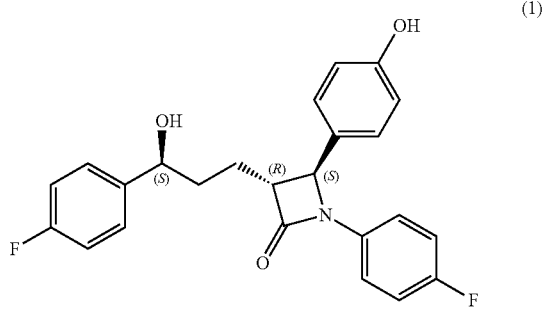

(1)

Compound (1) is commonly known as Ezetimibe and is the active ingredient in ZETIA®, manufactured by Merck/Schering-Plough Pharmaceuticals. Ezetimibe has been approved by the United States Food and Drug Administration for use in patients with high cholesterol to reduce LDL cholesterol and total cholesterol (see e.g., U.S. Pat. No. 6,207,822). Ezetimibe lowers high levels of blood cholesterol by selectively inhibiting the intestinal absorption of cholesterol and related phytosterols. Ezetimibe is commercially available in combination with simvastatin in the VYTORIN™ formulation from MSP Pharmaceuticals, Inc.

Numerous compounds that are analogs of Ezetimibe and being developed as possible therapeutics for lowering cholesterol are also known in the art (see e.g., PCT publications WO2006/17257A2, WO 2008/085300A1, and WO2008/039829A2).

Synthetic processes for the production of Ezetimibe and Ezetimibe derivatives have been previously disclosed. A variety of publications have disclosed chemical synthesis using a late reduction scheme that delays the reduction of the alcohol to the carbonyl to the last step of the reaction: U.S. Pat. No. 5,886,171, U.S. Pat. No. 5,738,321, WO 2005/0066120, WO 2007/030721, WO 2007/120824, WO 2007/119106, WO 2007/072088, WO 2007/030721, and WO 2007/120824.

U.S. Pat. No. 6,133,001 and WO 2000/060107 disclose using certain microorganisms (e.g., *Rhodococcus fascians* ATCC No. 202210 or *Geotrichum candidum* ATCC No. 74487) to carry out the stereoselective reduction of 1-(4-fluorophenyl)-3(R)-[3-oxo-3-(4-fluorophenyl)propyl)]-4(S)-(4-hydroxyphenyl)-2-azetidinone to 1-(4-fluorophenyl)-3(R)-[3(S)-hydroxy-3-(4-fluorophenyl)-propyl)]-4(S)-(4-hydroxyphenyl)-2-azetidinone. This is a microbial process, however, carried out under whole cell fermentation conditions.

WO 2008/151324A1 discloses using certain commercially available ketoreductase biocatalysts to prepare Ezetimibe and protected Ezetimibe analogs from the corresponding precursor ketone compounds. The biocatalysts and processes disclosed therein, however, use low substrate loadings (25 g/L or less), a GDH/glucose cofactor regeneration system, and result in low percentage conversion of substrate to the Ezetimibe product (~65% yield).

US20100062499A1 discloses engineered ketoreductase enzymes, and methods of using the engineered ketoreductase enzymes to convert the diketone compound, 5-((4S)-2-oxo-4-phenyl(1,3-oxazolidin-3-yl))-1-(4-fluorophenyl)pentane-1,-5-dione, to the chiral alcohol, (4S)-3-[(5S)-5-(4-fluorophenyl)-5-hydroxypentanoyl]-4-phenyl-1,3-oxazolid-in-2-one. This chiral alcohol made biocatalytically is an early stage intermediate that can be used in a process for making Ezetimibe.

It is desirable to have improved biocatalysts and a biocatalytic process having increased efficiency for use in a late stage biocatalytic reduction scheme for preparing Ezetimibe in high diastereomeric excess (>98% d.e.). Particularly desirable would be engineered biocatalysts capable of increased activity in large scale processes having high substrate loadings (e.g., >50 g/L), high percent conversion (e.g., >90% in 24 h), without the need for an additional cofactor regenerating enzyme, and capable of yielding Ezetimibe as product in high purity and diastereomeric excess.

4. SUMMARY

The present disclosure provides non-naturally occurring polypeptides having ketoreductase activity, polynucleotides encoding the polypeptides, methods of the making the polypeptides, and methods of using the polypeptides for the biocatalytic conversion of the keto-phenol substrate, 1-(4-fluorophenyl)-3(R)-[3-(4-fluorophenyl)-3-oxopropyl]-4(S)-(4-hydroxyphenyl)-2-azetidinone (compound (2) below) to the chiral (S)-alcohol product, 1-(4-fluorophenyl)-3(R)-[3-(4-fluorophenyl)-3(S)-hydroxypropyl]-4(S)-(4-hydroxyphenyl)-2-azetidinone (i.e., compound (1) commonly referred to as Ezetimibe) as shown in Scheme 1.

Scheme 1

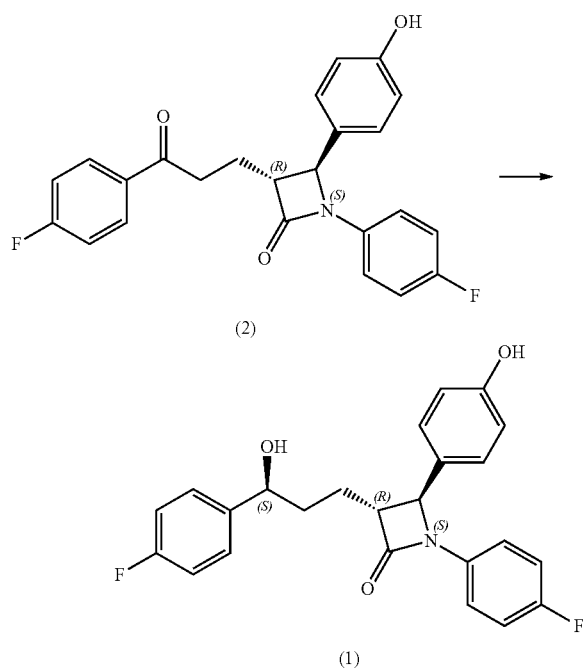

While naturally occurring ketoreductase polypeptides do not efficiently convert compound (2) to compound (1), the non-naturally occurring, engineered, ketoreductase polypeptides of the present disclosure are capable of carrying out this conversion with improved properties including, high diastereomeric excess (e.g., at least about 99% d.e.), increased activity (e.g., at least about 10-fold increased activity relative to the reference polypeptide SEQ ID NO:2), high percent conversion (e.g., at least about 90% conversion in 24 h), in the presence of high substrate loadings (e.g., at least about 50 g/L compound (2)), and without any cofactor regenerating enzyme other than the engineered ketoreductase polypeptide.

The non-naturally occurring polypeptides of the present disclosure capable of converting compound (2) to compound (1) with at least 2-fold, at least 10-fold, at least 25-fold, at least 40-fold, or at least 60-fold increased activity relative to the activity of the reference polypeptide of SEQ ID NO: 2, are synthetic variants of the naturally occurring ketoreductase of *Lactobacillus kefir*, and comprise amino acid sequences that have one or more residue differences as compared to the reference sequence of the synthetic variant ketoreductase polypeptide of SEQ ID NO:2. The residue differences occur at residue positions that affect functional properties of the enzyme including activity (e.g., percent conversion of substrate to product), stereoselectivity, substrate and/or product binding (e.g., resistance to substrate and/or product inhibition), thermostability, solvent stability, expression, or various combinations thereof. Accordingly, in some embodiments, the polypeptides of the disclosure can have one or more residue differences as compared to SEQ ID NO:2 at the following residue positions: X21, X25, X40, X64, X93, X94, X95, X96, X99, X108, X117, X127, X147, X148, X150, X152, X153, X155, X190, X195, X196, X201, X202, X203, X204, X205, X206, X207, X211, X221, X223, and X226 Amino acid residues that can be present at these positions are described in detail in the descriptions herein.

In some embodiments, the present disclosure provides a non-naturally occurring polypeptide of capable of converting compound (2) to compound (1) comprising an amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, and further comprises a set of amino acid residue differences as compared to SEQ ID NO:2 of any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168. In some embodiments, in addition to the set of amino acid residue differences of any one of the non-naturally occurring polypeptides of SEQ ID NO: 4 through SEQ ID NO: 168, the sequence of the non-naturally occurring polypeptide can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the SEQ ID NO: 2. In some embodiments, the residue differences can comprise conservative substitutions and non-conservative substitutions as compared to SEQ ID NO: 2.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2 and at least the following features: residue at position corresponding to X40 is R; residue at position corresponding to X153 is I, or L; residue at position corresponding to X190 is A or P; residue at position corresponding to X196 is T; residue at position corresponding to X199 is F, or W; and residue at position corresponding to X206 is I. In some embodiments, the amino acid sequence further comprises at least one feature or group of features selected from: (a) residue at position X93 is A and residue at position X94 is T; (b) residue at position X93 is A and residue at position X94 is S; (c) residue at position X93 is A and residue at position X94 is S; (d) residue at position X93 is I and residue at position X94 is S; (e) residue at position X203 is G; (f) residue at position X202 is G and residue at position X203 is G; or (f) residue at position X201 is A, residue at position X202 is G, and residue at position X203 is G.

In some embodiments, any of the non-naturally occurring polypeptides of the present disclosure capable of converting compound (2) to compound (1) with at least 2-fold, at least 10-fold, at least 25-fold, at least 40-fold, or at least 60-fold increased activity relative to the activity of the polypeptide of SEQ ID NO: 2 and an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, can further one or more features selected from: residue at position corresponding to X21 is R or F; residue at position corresponding to X25 is R, T, or N; residue at position corresponding to X40 is R; residue at position corresponding to X64 is V; residue at position corresponding to X93 is A; residue at position corresponding to X94 is T, S, or P; residue at position corresponding to X95 is V, or M; residue at position corresponding to X96 is V, G, A, N, S, P, or T; residue at position corresponding to X99 is L; residue at position corresponding to X108 is H; residue at position corresponding to X117 is A, or G; residue at position corresponding to X127 is K, or Q; residue at position corresponding to X147 is M, or I; residue at position corresponding to X148 is I; residue at position corresponding to X150 is H, or A; residue at position corresponding to X152 is N, or F; residue at position corresponding to X153 is I, or L; residue at position corresponding to X155 is C; residue at position corresponding to X190 is A; residue at position corresponding to X195 is M; residue at position corresponding to X196 is T, A, S, C, or N; residue at position corresponding to X199 is F, or W; residue at position corresponding to X201 is I, L, or A; residue at position corresponding to X202 is L, N, V, or G; residue at position corresponding to X203 is G; residue at position corresponding to X204 is V, or A; residue at position corresponding to X205 is V; residue at position corresponding to X206 is I; residue at position corresponding to X207 is T, C, I, or N; residue at position corresponding to X211 is K; residue at position corresponding to X221 is D; residue at position corresponding to X223 is I; residue at position corresponding to X226 is V.

In some embodiments, the non-naturally occurring polypeptides of the present disclosure can comprise a sequence having various combinations of the residue differences as compared to SEQ ID NO:2 disclosed herein at residue positions affecting enzymatic activity, thermostability, solvent stability, and cofactor binding.

In some embodiments, the non-naturally occurring polypeptides of the present disclosure can comprise a sequence having one or more amino acid residue differences as compared to SEQ ID NO: 2 at residue positions affecting activity for conversion of compound (2) to compound (1), are selected from the following position: X21; X25; X64; X93; X94; X95; X96; X99; X108; X117; X127; X147; X148; X150; X152; X153; X155; X163; X190; X195; X196; X199; X201; X202; X203; X204; X205; X206; X207; X211; X221; X223; and X226. In some embodiments, specific amino acid differences at residue positions resulting in increased activity for conversion of compound (2) to compound (1) relative to the reference polypeptide of SEQ ID NO: 2 can be selected from the following substitutions: L21FR; D25NRT; A64V; I93AT; A94PST; L95MV; Q96ANGPSTV; V99L; R108DHK; S117AG; R127KQ; L147IM; V148I; D150H; M152NF; V153IL; A155C; V163I; C190A; L195M; V196ACNST; D199FW; G201AIL; A202GLNV; E203G; E204AV; M205V; M206I; S207TCIN; R211K; N221D; V223I; and I226V.

In some embodiments, the non-naturally occurring polypeptides of the present disclosure can comprise an amino acid sequence having one or more residue differences as compared to SEQ ID NO: 2 at residue positions affecting thermostability, which positions include the following: X21; X93; X94; X117; X127; X147; X195; and X199. In some embodiments, specific amino acid differences at residue positions resulting in increased thermostability relative to the reference polypeptide of SEQ ID NO: 2 can be selected from the following substitutions: L21F; A93T; S94A; S117GA; R127K; L147I; L195M; and D199W.

In some embodiments, the non-naturally occurring polypeptides of the present disclosure can comprise an amino acid sequence having residue differences as compared to SEQ ID NO: 2 at residue positions affecting solvent stability, which positions include X25; X147; and X221. In some embodiments, specific amino acid differences at residue positions resulting in increased solvent stability relative to the reference polypeptide of SEQ ID NO: 2 can be selected from the following substitutions: D25R; L147M; and N221D.

In some embodiments, the non-naturally occurring polypeptides of the present disclosure can comprise an amino acid sequence having residue differences as compared to SEQ ID NO: 2 at residue positions affecting cofactor binding, which positions include X40. In some embodiments, specific amino acid differences at residue positions affecting cofactor binding can be selected from the following substitutions: H40R.

In addition to the residue position specified above, various other residue differences relative to SEQ ID NO:2 can be present at other residue positions in the ketoreductase polypeptides disclosed herein. These can be conservative or non-conservative differences, including conservative substitutions and non-conservative substitutions. Guidance on the choice of amino acid residues at the specified positions is provided in the detailed description.

In some embodiments, the present disclosure provides polynucleotides encoding the non-naturally occurring polypeptides capable of converting compound (2) to compound (1), as well as expression vectors comprising the polynucleotides, and host cells capable of expressing the polynucleotides encoding the non-naturally occurring polypeptides. Accordingly, in some embodiments, the present disclosure also provides methods of manufacturing the non-naturally occurring polypeptides capable of converting compound (2) to compound (1), wherein the methods comprise culturing a host cell capable of expressing a polynucleotide encoding the non-naturally occurring polypeptide and isolating the polypeptide from the host cell.

In some embodiments, any of the non-naturally occurring polypeptides of the present disclosure can be used in improved processes for carrying out the conversion of compound (2) to compound (1) due to their improved enzymatic properties including, high diastereomeric excess (e.g., at least about 99% d.e.), increased activity (e.g., at least about 10-fold increased activity relative to SEQ ID NO:2), high percent conversion (e.g., at least about 90% conversion in 24 h), in the presence of high substrate loadings (e.g., at least about 50 g/L compound (2)), and without any cofactor regenerating enzyme other than the non-naturally occurring ketoreductase polypeptide. Accordingly, in some embodiments, the present disclosure provides methods using the non-naturally occurring polypeptides for preparing compound (1) in diastereomeric excess, wherein the methods comprise: contacting compound (2) with an non-naturally occurring or engineered polypeptide of the present disclosure (e.g., as described in Table 2 and elsewhere herein) in the presence of NADPH or NADH cofactor under suitable reaction conditions. Suitable reactions conditions for the conversion of compound (2) to compound (1) using the engineered polypeptides of the present disclosure are described in greater detail below, including but not limited to ranges of pH, temperature, buffer, solvent system, substrate loading, polypeptide loading, cofactor loading, atmosphere, and reaction time.

In some embodiments, the improved enzymatic activity of the engineered polypeptides in the conversion of compound (2) to compound (1) provides for methods wherein a higher percentage conversion can be achieved with a lower concentration of polypeptide. The use of lower concentration of the engineered polypeptide in a method comprising a conversion of compound (2) to compound (1) also reduces the amount of residual protein that may need to be removed in subsequent steps for purification of compound (1). Accordingly, in some embodiments, the methods for preparing compound (1) of the present disclosure can be carried out wherein the suitable reaction conditions can comprise e.g., a compound (2) substrate loading of at least about 20 g/L, about 40 g/L, about 50 g/L, about 75 g/L, about 100 g/L, about 200 g/L, about 250 g/L, about 300 g/L, or about 400 g/L; and/or a non-naturally occurring polypeptide concentration of about 0.1-3.0 g/L, about 0.5-2.75 g/L, about 1.0-2.5 g/L, about 1.5-2.5 g/L, about 3 g/L, about 2 g/L, about 1.5 g/L, about 1.0 g/L, about 0.75 g/L, or even lower concentration.

In some embodiments, the present disclosure also provides methods for preparing compound (1) or an analog of compound (1), wherein the methods comprise contacting compound (2) or an analog of compound (2) with a non-naturally occurring or engineered polypeptide in the presence of NADPH or NADH cofactor under suitable reaction conditions and further comprises chemical steps of product work-up, extraction, isolation, purification, and/or crystallization of compound (1), each of which can be carried out under a range of conditions disclosed herein.

In some embodiments, the methods for preparing compound (1) using a non-naturally occurring polypeptide of the present disclosure further comprise a cofactor recycling system capable of converting NADP$^+$ to NADPH, or NAD$^+$ to NADH. The cofactor recycling system can comprise a dehydrogenase enzyme (e.g., glucose dehydrogenase, glucose-phosphate dehydrogenase, formate dehydrogenase, or a ketoreductase/alcohol dehydrogenase) and a corresponding substrate (e.g., glucose, glucose-6-phosphate, formate, or secondary alcohol). In some embodiments, the co-factor recycling system comprises a ketoreductase polypeptide and a secondary alcohol, preferably isopropanol. In some embodiments of the methods of the present disclosure, the non-naturally occurring polypeptide capable of converting compound (2) to compound (1) is also capable of converting a secondary alcohol (e.g., isopropanol) to its corresponding secondary ketone (e.g., acetone), and the method of preparing compound (1) further comprises a co-factor recycling system comprising the non-naturally occurring polypeptide and a secondary alcohol.

In some embodiments, an analog of compound (1) can be prepared in diastereomeric excess from an analog of compound (2) using the above described methods. In some embodiments, the analog of compound (1) prepared using the methods comprises a compound of Formula Ia:

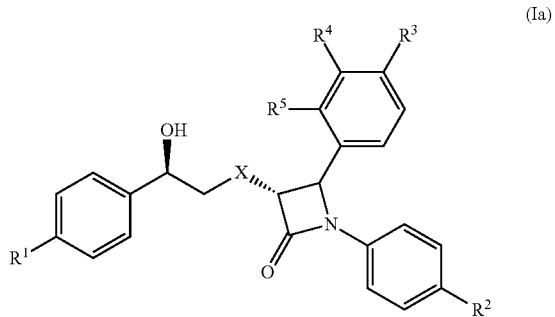

wherein,
X is C or S;
R$^1$ is selected from —H, —F, —Cl, —Br, or —I;
R$^2$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;
R$^3$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;
R$^4$ is selected from —H, —F, —Cl, —Br, —I, —CN, —OH (optionally protected with a hydroxyl protecting group); and
R$^5$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle.

Accordingly, in some embodiments the present disclosure provides a method of preparing a compound of Formula Ia in diastereomeric excess comprising: contacting a compound of Formula IIa

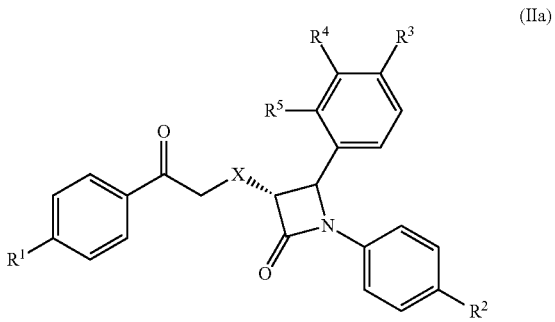

wherein, X, R$^1$, R$^2$, R$^3$, R$^4$, and R$^5$, are defined as above for Formula Ia, with an engineered polypeptide of the present disclosure (e.g., as described in Table 2 and elsewhere herein) in the presence of NADPH or NADH cofactor under suitable reaction conditions.

5. DETAILED DESCRIPTION

The present disclosure provides highly stereoselective and efficient biocatalysts capable of mediating the conversion of 1-(4-fluorophenyl)-3(R)-[3-(4-fluorophenyl)-3-oxopropyl]-4(S)-(4-hydroxyphenyl)-2-azetidinone to 1-(4-fluorophenyl)-3(R)-[3-(4-fluorophenyl)-3(S)-hydroxypropyl]-4(S)-(4-hydroxyphenyl)-2-azetidinone in diastereomeric excess. The biocatalysts described herein have been designed by changing the amino acid sequence of a naturally occurring ketoreductase to form polypeptides with the desired enzymatic properties, e.g., enzyme activity, stereoselectivity, by product formation, thermostability, and expression. The detailed description that follow describes the polypeptides and processes for carrying out the conversion of 1-(4-fluorophenyl)-3(R)-[3-(4-fluorophenyl)-3-oxopropyl]-4(S)-(4-hydroxyphenyl)-2-azetidinone to 1-(4-fluorophenyl)-3(R)-[3-(4-fluorophenyl)-3(S)-hydroxypropyl]-4(S)-(4-hydroxyphenyl)-2-azetidinone in diastereomeric excess.

For the descriptions herein and the appended claims, the singular forms "a", "an" and "the" include plural referents unless the context clearly indicates otherwise. Thus, for example, reference to "a polypeptide" includes more than one polypeptide, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure.

5.2 Definitions

The technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Non-naturally occurring" or "engineered" or "recombinant" when used in the present disclosure with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M.

Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as stereoselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate (e.g., compound (2), 1-(4-fluorophenyl)-3(R)-[3-(4-fluorophenyl)-3-oxopropyl]-4(S)-(4-hydroxyphenyl)-2-azetidinone) to its corresponding product (e.g., compound (1), 1-(4-fluorophenyl)-3(R)-[3-(4-fluorophenyl)-3(S)-hydroxypropyl]-4(S)-(4-hydroxyphenyl)-2-azetidinone) with at least about 85% stereoisomeric excess.

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include Thr (T), Ser (S), His (H), Glu (E), Asn (N), Gln (O), Asp (D), Lys (K) and Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include Glu (E) and Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include Arg (R) and Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include Pro (P), Ile (I), Phe (F), Val (V), Leu (L), Trp (W), Met (M), Ala (A) and Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include Phe (F), Tyr (Y) and Trp (W). Although owing to the its heteroaromatic ring side chain His (H) is classified as an aromatic residue, it may also be classified as a basic residue owing to pKa of its heteroaromatic nitrogen atom.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include Gly (G), Leu (L), Val (V), Ile (I), Met (M) and Ala (A).

"Aliphatic Amino Acid or Residue" refers to a hydrophobic amino acid or residue having an aliphatic hydrocarbon side chain. Genetically encoded aliphatic amino acids include Ala (A), Val (V), Leu (L) and Ile (I).

The amino acid Cys (C) is unique in that it can form disulfide bridges with other Cys (C) amino acids or other sulfanyl- or sulfhydryl-containing amino acids. The ability of Cys (and other amino acids with —SH containing side chains) to exist in a polypeptide in either the reduced free —SH or oxidized disulfide-bridged form affects whether it contributes net hydrophobic or hydrophilic character to the polypeptide. While Cys exhibits a hydrophobicity of 0.29 according to the normalized consensus scale of Eisenberg (Eisenberg et al., 1984, supra), it is to be understood that for purposes of the present disclosure, Cys is classified into its own unique group.

The amino acid Pro (P) has a conformationally constrained nature. Although it has hydrophobic properties, as used herein, Pro (P) or other similar residues is classified as a "conformationally constrained."

"Hydroxyl-containing Amino Acid or Residue" refers to an amino acid or residue containing a hydroxyl (—OH) moiety. Genetically-encoded hydroxyl-containing amino acids include Ser (S) and Thr (T). While L-Tyr (Y) contains a hydroxyl moiety, it is classified herein as an aromatic amino acid or residue.

"Amino acid difference" or "residue difference" refers to a change in the residue at a specified position of a polypeptide sequence when compared to a reference sequence. For example, a residue difference at position X3, where the reference sequence has a glutamine, refers to a change of the residue at position X3 to any residue other than glutamine. As disclosed herein, an enzyme can include one or more residue differences relative to a reference sequence, where multiple residue differences typically are indicated by a list of the specified positions where changes are made relative to the reference sequence. The residue differences can be non-conservative changes or conservative changes. In some embodiments, the residue differences can be conservative substitutions, non-conservative substitutions, or a combination of non-conservative and conservative substitutions. For the descriptions of the non-naturally occurring polypeptides herein, the amino acid residue position in the reference sequence is determined in the ketoreductase polypeptide beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The polypeptide sequence position at which a particular amino acid or amino acid change ("residue difference") is present is sometimes described herein as "Xn", or "position n", where n refers to the residue position with respect to the reference sequence. Where applicable, a specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence, and Y is the single letter identifier of the residue substitution in the engineered sequence.

"Conservative amino acid substitutions" refer to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1.

TABLE 1

| Residue | Possible Conservative Substitutions |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can typically have about 80%, 90%, 95%, 98%, and 99% of the full-length ketoreductase polypeptide, for example the polypeptide of SEQ ID NO:2.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present disclosure can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 95% or more, and about 98% or more of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

The terms "glucose dehydrogenase" and "GDH" are used interchangeably herein to refer to an $NAD^+$ or $NADP^+$-dependent enzyme that catalyzes the conversion of D-glucose and $NAD^+$ or $NADP^+$ to gluconic acid and NADH or NADPH, respectively.

The term "secondary alcohol dehydrogenase" is used herein to refer to an $NAD^+$ or $NADP^+$-dependent enzyme that catalyzes the conversion of a secondary alcohol (e.g., isopropanol) and $NAD^+$ or $NADP^+$ to a ketone and NADH or NADPH, respectively.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl- groups preferably having from 2 to 6 carbon atoms in the alkenyl moiety and from 6 to 10 carbon atoms inclusively in the aryl moiety.

"Arylalkynyl" refers to aryl-alkynyl- groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups, such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl- groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl- groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl- groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl- groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl- groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. such heterocyclic groups can have a single ring (e.g., piperidinyl or tetrahydrofuryl) or multiple condensed rings (e.g., indolinyl, dihydrobenzofuran or quinuclidinyl). preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

The term "suitable reaction conditions" refers to those conditions in the biocatalytic reaction solution (e.g., ranges of enzyme loading, substrate loading, cofactor loading, T, pH, buffers, co-solvents, etc.) under which a non-naturally occurring ketoreductase polypeptide of the present disclosure is capable of converting compound (2) to compound (1) (or compound of Formula IIa to compound of Formula Ia). Exemplary "suitable reaction conditions" are provided in the present disclosure and illustrated by the Examples.

5.3 Non-Naturally Occurring or Engineered Ketoreductase Polypeptides

Enzymes belonging to the ketoreductase (KRED) or carbonyl reductase class (EC1.1.1.184) are useful for the synthesis of optically active alcohols from the corresponding prostereoisomeric ketone substrates and by stereospecific reduction of corresponding racemic aldehyde and ketone substrates. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD and NADP serve as electron acceptors. It is frequently observed that KREDs and other alcohol dehydrogenases accept either the phosphorylated or the non-phosphorylated co-factor (in its oxidized and reduced state).

KREDs are being used increasingly in place of chemical procedures for the conversion of different keto and aldehyde compounds to chiral alcohol products. These biocatalytic conversions can employ whole cells expressing the ketoreductase for biocatalytic ketone reductions, or purified enzymes, particularly in those instances where presence of multiple ketoreductases in whole cells would adversely affect the enantiomeric purity and yield of the desired product. For in vitro applications, a co-factor (NADH or NADPH) regenerating enzyme such as glucose dehydrogenase (GDH), formate dehydrogenase etc. is used in conjunction with the ketoreductase.

Examples illustrating the use of naturally occurring or engineered KREDs in biocatalytic processes to generate useful chemical compounds include asymmetric reduction of 4-chloroacetoacetate esters (Zhou, *J. Am. Chem. Soc.* 1983 105:5925-5926; Santaniello, *J. Chem. Res.* (S) 1984:132-133; U.S. Pat. No. 5,559,030; U.S. Pat. No. 5,700,670 and U.S. Pat. No. 5,891,685), reduction of dioxocarboxylic acids (e.g., U.S. Pat. No. 6,399,339), reduction of tert-butyl (S)-chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

KREDs can be found in a wide range of bacteria and yeasts (for reviews: Kraus and Waldman, Enzyme catalysis in organic synthesis Vols. 1&2. VCH Weinheim 1995; Faber, K., Biotransformations in organic chemistry, 4th Ed. Springer, Berlin Heidelberg N.Y. 2000; Hummel and Kula *Eur. J. Biochem.* 1989 184:1-13). Several KRED gene and enzyme sequences have been reported, including: *Candida magnoliae* (Genbank Acc. No. JC7338; GI: 11360538); *Candida parapsilosis* (Genbank Acc. No. BAA24528.1; GI: 2815409), *Sporobolomyces salmonicolor* (Genbank Acc. No. AF160799; GI: 6539734); *Lactobacillus kefir* (Genbank Acc. No. AAP94029.1; GI: 33112056); *Lactobacillus brevis* (Genbank Acc. No. 1NXQ_A; GI: 30749782); and *Thermoanaerobium brockii* (Genbank Acc. No. P14941; GI: 1771790).

These naturally occurring ketoreductase polypeptides do not efficiently convert compound (2) to compound (1). The non-naturally occurring, engineered, ketoreductase polypeptides of the present disclosure, however, are capable of carrying out this conversion with improved properties including, high diastereomeric excess (e.g., at least about 99% d.e.), increased activity (e.g., at least about 10-fold increased activity relative to the reference polypeptide SEQ ID NO:2), high percent conversion (e.g., at least about 90% conversion in 24 h), in the presence of high substrate loadings (e.g., at least about 50 g/L compound (2)), and without any cofactor regenerating enzyme other than the engineered ketoreductase polypeptide.

The non-naturally occurring polypeptides of the present disclosure are synthetic variants of the naturally occurring ketoreductase of *Lactobacillus kefir*, and comprise amino acid sequences that have one or more residue differences as compared to the reference sequence of the synthetic variant ketoreductase polypeptide of SEQ ID NO:2. The residue differences occur at residue positions that affect enzyme activity, stereoselectivity, thermostability, expression, or various combinations thereof. The residue differences provide structural changes that allow the engineered polypeptides to convert the ketophenol substrate, 1-(4-fluorophenyl)-3(R)-[3-(4-fluorophenyl)-3-oxopropyl]-4(S)-(4-hydroxyphenyl)-2-azetidinone (compound (2); MW 407.41) to the chiral alcohol product, 1-(4-fluorophenyl)-3(R)-[3-(4-fluorophenyl)-3(S)-hydroxypropyl]-4(S)-(4-hydroxyphenyl)-2-azetidinone (compound (1); MW 409.43) (as illustrated in Scheme 1) with at least 2-fold, at least 10-fold, at least 25-fold, at least 40-fold, or at least 60-fold increased activity relative to the activity of the reference polypeptide of SEQ ID NO: 2. Further these engineered polypeptides are capable of highly stereoselective conversion of compound (2) to compound (1) in at least about 97%, about 98%, or at least about 99% diastereomeric excess. Further, in some embodiments these non-naturally occurring polypeptides are capable of catalyzing the conversion of compound (2) to compound (1) using added cofactor (NADPH or NADH), or in presence of a co-factor recycling system, for example an appropriate dehydrogenase (e.g., glucose dehydrogenase, formate dehydrogenase or ketoreductase/alcohol dehydrogenase) and a suitable dehydrogenase substrate, such as glucose, glucose-6-phosphate, formate, or a secondary alcohol, e.g., isopropanol. In some embodiments, the non-naturally occurring ketoreductase polypeptides can function not only to convert compound (2) to compound (1), but also function as the secondary alcohol dehydrogenase of a cofactor recycling system and thereby recycle the cofactor in the presence of a secondary alcohol. Thus, the engineered biocatalysts present disclosure are capable of providing highly efficient biocatalytic processes for preparing Ezetimibe as substantially enantiomerically pure preparations.

Structure and function information for exemplary non-naturally occurring (or engineered) ketoreductase polypeptides of the present disclosure are shown below in Table 2. The odd numbered sequence identifiers (i.e., SEQ ID NOs) refer to the nucleotide sequence encoding the amino acid sequence provided by the even numbered SEQ ID NOs, and the sequences are provided in the electronic sequence listing file accompanying this disclosure, which is hereby incorporated by reference herein. The amino acid residue differences are based on comparison to the reference sequence of SEQ ID NO: 2, which is an engineered ketoreductase having the following 19 residue differences relative to the amino acid sequence of the naturally occurring wild-type ketoreductase of *Lactobacillus kefir* (Genbank acc. No. AAP94029.1; GI: 33112056): D3N, G7S, L17Q, V95L, S96Q, G117S, Q127R, E145S, F147L, T152M, L153V, L176V, Y190C, D198K, L199D, E200P, K211R, I223V, and A241S. The activity of each engineered polypeptide relative to the reference polypeptide of SEQ ID NO: 2 was determined as conversion of substrate of compound (2) to product of compound (1) over a 24 h period at room temperature in a 96-well plate format assay of cell lysates containing the engineered polypeptides. General assay protocol and reaction conditions were as follows (with exceptions noted in Table 2): 60 μL of a 13.33 g/L solution of the compound (2) in toluene:IPA:acetone (v/v/v ratio of 5:9:1) added to each well of a Costar™ deep-well 96-well plate; subsequently, 120 μL of a 0.8 g/L solution of NADP in 100 mM TEA buffer, pH 7.0 containing 1 mM MgSO$_4$ added to each well; finally, 20 μL of a freshly prepared suspension of lysed cells (i.e., cells expressing the variant polypeptide) in lysis buffer were added to make the total volume in each well 200 μL. Final conditions in each well (except as noted below): [compound (2)]=4 g/L, [NADP]=0.5 g/L, Solvent=toluene:IPA:acetone:buffer (relative % volumes of 10:18:2:70). The plate was then heat sealed and shaken for 24 h at RT (or 37° C.) before 0.8 mL of acetonitrile was added to each well to quench the reaction. The levels of activity (i.e., "+" "++" "+++" etc.) are defined as follows: "+" indicates at least equal to but less than 2 times the activity of SEQ ID NO: 2; "++" indicates at least 2 times but less than 10 times the activity of SEQ ID NO: 2; "+++" indicates at least 10 times but less than 25 times the activity of SEQ ID NO: 2; "++++" indicates at least 25 times but less than 40 times the activity of SEQ ID NO: 2; "+++++" indicates at least 40 times but less than 60 times the activity of SEQ ID NO: 2; "++++++" indicates at least 60 times the activity of SEQ ID NO: 2.

TABLE 2

| SEQ ID NO (nt/aa) | Residue differences (relative to SEQ ID NO: 2) | Activity (relative to SEQ ID NO: 2) |
|---|---|---|
| 3/4 | H40R; V153I; C190A; E204V; | ++ |
| 5/6 | H40R; I93A; A94T; V153I; C190A; V196T; D199F; M206I; | ++ |
| 7/8 | H40R; | + |
| 9/10 | H40R; V148I; | + |
| 11/12 | H40R; V196A; | + |
| 13/14 | H40R; S207T; | ++ |
| 15/16 | H40R; Q96V; | + |
| 17/18 | H40R; V196S; | + |
| 19/20 | H40R; V196C; | ++ |
| 21/22 | H40R; V196N; | ++ |
| 23/24 | H40R; A202L; | ++ |
| 25/26 | H40R; A202N; | + |
| 27/28 | H40R; A202V; | ++ |
| 29/30 | H40R; I93A; A94P; V153I; C190A; V196T; D199F; M206I; | ++ |
| 31/32 | H40R; Q96G; V153I; C190A; V196T; D199F; M206I; | ++ |
| 33/34 | H40R; Q96A; V153I; C190A; V196T; D199F; M206I; | ++ |
| 35/36 | H40R; I93A; A94T; V153I; C190A; V196T; D199F; E203G; M206I; | ++ |
| 37/38 | H40R; I93A; A94T; Q96V; V153I; C190A; V196T; D199F; M206I; | + |
| 39/40 | H40R; I93A; A94T; V153I; C190A; L195M; V196T; D199F; M206I; | ++ |
| 41/42 | H40R; I93A; A94T; V153I; C190A; V196T; D199F; M206I; S207C; | ++ |
| 43/44 | H40R; I93A; A94T; V153I; C190A; V196T; D199F; M206I; S207I; | ++ |
| 45/46 | H40R; I93A; A94T; V153I; C190A; V196T; D199F; M206I; S207N; | ++ |
| 47/48 | L21R; D25R; H40R; I93A; A94T; S117K; R127K; L147M; V153I; C190A; V196T; D199F; E203G; M206I; N221D; | +++[1] |
| 49/50 | L21F; D25R; H40R; I93A; A94T; S117G; L147M; V153I; C190A; V196T; D199F; E203G; M206I; N221D; | +++[1] |
| 51/52 | H40R; I93A; A94S; Q96N; V153L; C190A; V196T; D199F; A202G; E203G; M206I; | +++[1] |
| 53/54 | D25T; H40R; I93A; A94T; R108H; V153I; C190A; V196T; D199F; E203G; M206I; | +++[1] |
| 55/56 | H40R; I93A; A94T; D150H; V153I; C190A; V196T; D199F; E203G; M206I; | +++[1] |
| 57/58 | H40R; I93A; A94T; V153I; C190P; V196T; D199F; E203G; M206I; | +++[1] |
| 59/60 | H40R; I93A; A94T; V153I; C190A; V196T; D199F; E203G; E204A; M206I; | +++[1] |
| 61/62 | H40R; I93A; A94T; V153I; C190A; V196T; D199F; E203G; E204V; M206I; | +++[1] |
| 63/64 | H40R; I93A; A94T; V153I; C190A; V196T; D199F; E203G; M205V; M206I; | +++[1] |
| 65/66 | H40R; I93A; A94T; M152N; V153I; C190A; V196T; D199F; E203G; M206I; | +++[1] |
| 67/68 | H40R; I93A; A94T; M152F; V153I; C190A; V196T; D199F; E203G; M206I; | +++[1] |
| 69/70 | H40R; I93A; A94T; Q96A; V153I; C190A; V196T; D199F; E203G; M206I; S207T; | +++[1] |
| 71/72 | D25N; H40R; I93A; A94T; V153I; C190A; V196T; D199F; E203G; M206I; | +++[1] |
| 73/74 | D25T; H40R; I93A; A94T; V153I; C190A; V196T; D199F; E203G; M206I; | +++[1] |
| 75/76 | H40R; I93A; A94T; V153I; C190A; L195M; V196T; D199F; E203G; M206I; S207C; | +++[1] |

TABLE 2-continued

| SEQ ID NO (nt/aa) | Residue differences (relative to SEQ ID NO: 2) | Activity (relative to SEQ ID NO: 2) |
|---|---|---|
| 77/78 | H40R; I93A; A94S; Q96S; V153L; C190A; V196T; D199F; A202G; E203G; M206I; | +++[1] |
| 79/80 | H40R; I93A; A94S; Q96P; V153L; C190A; V196T; D199F; A202G; E203G; M206I; | +++[1] |
| 81/82 | H40R; I93A; A94S; Q96A; V153L; C190A; V196T; D199F; A202G; E203G; M206I; | ++++[1] |
| 83/84 | H40R; I93A; A94S; Q96T; V153L; C190A; V196T; D199F; A202G; E203G; M206I; | +++[1] |
| 85/86 | H40R; I93A; A94S; Q96N; V153L; C190A; V196T; D199F; A202G; E203G; M206I; R211K; | +++[1] |
| 87/88 | H40R; I93A; A94S; Q96N; V153L; A155C; C190A; V196T; D199F; A202G; E203G; M206I; | +++[1] |
| 89/90 | H40R; I93A; A94S; Q96N; V153L; C190A; V196T; D199F; G201I; A202G; E203G; M206I; | +++[1] |
| 91/92 | H40R; I93A; A94S; Q96N; V153L; C190A; V196T; D199F; G201L; A202G; E203G; M206I; | +++[1] |
| 93/94 | H40R; I93A; A94S; Q96N; V153L; C190A; V196T; D199F; G201A; A202G; E203G; M206I; | +++[1] |
| 95/96 | H40R; I93A; A94S; L95V; Q96N; R127Q; V153L; C190A; V196T; D199F; A202G; E203G; M206I; R211K; | +++[1] |
| 97/98 | H40R; A94S; L95M; Q96N; L147M; V153L; C190A; V196T; D199F; G201I; A202G; E203G; M206I; | +++[1] |
| 99/100 | H40R; A94S; Q96P; V153L; C190A; V196T; D199F; G201A; A202G; E203G; M206I; R211K; | ++++[2] |
| 101/102 | L21F; D25R; H40R; I93A; A94S; Q96P; R108K; S117G; L147M; V153L; C190A; V196T; D199F; A202G; E203G; M206I; N221D; | ++++[2] |
| 103/104 | L21R; D25R; H40R; I93A; A94S; Q96P; R108K; S117G; L147M; V153L; C190A; V196T; D199F; A202G; E203G; M206I; N221D; | ++++[2] |
| 105/106 | L21F; D25R; H40R; I93A; A94S; Q96P; R108K; R127K; L147M; V153L; C190A; V196T; D199F; A202G; E203G; M206I; N221D; | +++++[2] |
| 107/108 | L21R; D25R; H40R; I93A; A94S; Q96P; R108K; S117G; L147M; V153L; C190A; V196T; D199F; A202G; E203G; M206I; | ++++[2] |
| 109/110 | L21F; D25R; H40R; I93A; A94S; Q96P; R108K; S117G; L147M; V153L; V163I; C190A; V196T; D199F; A202G; E203G; M206I; N221D; | ++++[2] |
| 111/112 | L21R; H40R; I93A; A94S; Q96P; S117G; L147M; V153L; C190A; V196T; D199F; A202G; E203G; M206I; N221D; | ++++[2] |
| 113/114 | L21R; H40R; I93A; A94S; Q96P; S117G; R127K; L147M; V153L; C190A; V196T; D199F; A202G; E203G; M206I; N221D; | ++++[2] |
| 115/116 | H40R; I93A; A94S; Q96P; S117G; L147M; V153L; C190A; V196T; D199F; A202G; E203G; M206I; N221D; | ++++[2] |
| 117/118 | D25R; H40R; I93A; A94S; Q96P; R108D; S117G; R127K; L147M; V153L; C190A; V196T; D199F; A202G; E203G; M206I; N221D; | ++++[2] |
| 119/120 | H40R; I93A; A94S; Q96P; S117G; L147M; V153L; C190A; V196T; D199F; A202G; E203G; M206I; | ++++[2] |
| 121/122 | H40R; I93A; A94S; Q96P; R108K; S117G; R127K; L147M; V153L; C190A; V196T; D199F; A202G; E203G; M206I; N221D; | ++++[2] |
| 123/124 | L21R; D25R; H40R; I93A; A94S; Q96P; S117G; R127K; V153L; C190A; V196T; D199F; A202G; E203G; M206I; N221D; | ++++[2] |
| 125/126 | D25R; H40R; I93A; A94S; Q96P; S117G; R127K; V153L; C190A; V196T; D199F; A202G; E203G; M206I; | ++++[2] |
| 127/128 | D25R; H40R; I93A; A94S; Q96P; R108K; S117G; R127K; L147M; V153L; C190A; V196T; D199F; A202G; E203G; M206I; N221D; | +++++[2] |
| 129/130 | D25R; H40R; I93A; A94S; Q96P; L147M; V153L; C190A; V196T; D199F; A202G; E203G; M206I; N221D; | ++++[2] |
| 131/132 | L21R; D25R; H40R; I93A; A94S; Q96P; S117G; L147M; V153L; C190A; V196T; D199F; A202G; E203G; M206I; N221D; | ++++[2] |
| 133/134 | H40R; I93T; A94S; Q96P; V153L; C190A; V196T; D199F; A202G; E203G; M206I; | ++++[2] |
| 135/136 | H40R; I93A; Q96P; V153L; C190A; V196T; D199F; A202G; E203G; M206I; | ++++[2] |
| 137/138 | H40R; I93A; A94S; Q96P; V153L; C190A; V196T; D199F; A202G; E203G; M205V; M206I; | ++++[2] |
| 139/140 | H40R; A94S; Q96P; S117A; V153L; C190A; V196T; D199F; G201A; A202G; E203G; M206I; R211K; | +++++[3] |
| 141/142 | H40R; A94S; Q96P; S117G; V153L; C190A; V196T; D199F; G201A; A202G; E203G; M206I; R211K; | ++++[3] |
| 143/144 | H40R; A94S; Q96P; V153L; C190A; V196T; D199W; G201A; A202G; E203G; M206I; R211K; | +++++[3] |
| 145/146 | H40R; A94S; Q96P; L147M; V153L; C190A; V196T; D199F; G201A; A202G; E203G; M206I; R211K; | ++++[3] |
| 147/148 | H40R; A64V; A94S; Q96P; V153L; C190A; V196T; D199F; G201A; A202G; E203G; M206I; R211K; | ++++[3] |
| 149/150 | H40R; A94S; Q96P; V153L; C190A; V196T; D199F; G201A; A202G; E203G; M206I; R211K; V223I; | ++++[3] |

TABLE 2-continued

| SEQ ID NO (nt/aa) | Residue differences (relative to SEQ ID NO: 2) | Activity (relative to SEQ ID NO: 2) |
|---|---|---|
| 151/152 | H40R; A94S; Q96P; V153L; C190A; L195M; V196T; D199F; G201A; A202G; E203G; M206I; R211K; | ++++[3] |
| 153/154 | H40R; A94S; Q96P; L147I; V153L; C190A; V196T; D199F; G201A; A202G; E203G; M206I; R211K; | ++++[3] |
| 155/156 | H40R; A94S; Q96P; V99L; R108H; L147I; V153L; C190A; V196T; D199F; G201A; A202G; E203G; M205V; M206I; R211K; I226V; | +++++[3] |
| 157/158 | H40R; A94S; Q96P; V99L; R108H; L147I; V153L; C190A; V196T; D199F; G201A; A202G; E203G; M206I; R211K; I226V; | +++++[3] |
| 159/160 | H40R; A94S; Q96P; V99L; L147I; V153L; C190A; V196T; D199F; G201A; A202G; E203G; M205V; M206I; R211K; | +++++[3] |
| 161/162 | H40R; A94S; Q96P; V99L; R108H; S117G; L147I; V153L; C190A; V196T; D199F; G201A; A202G; E203G; M206I; R211K; I226V; | +++++[3] |
| 163/164 | H40R; A94S; Q96P; V99L; R108H; L147I; V153L; C190A; V196T; D199F; G201A; A202G; E203G; M205V; M206I; R211K; | +++++[3] |
| 165/166 | H40R; A94S; Q96P; V99L; L147I; V153L; C190A; V196T; D199F; G201A; A202G; E203G; M205V; M206I; R211K; I226V; | ++++[3] |
| 167/168 | H40R; A64V; A94S; Q96P; V99L; R108H; S117G; L147I; V153L; C190A; V196T; D199W; G201A; A202G; E203G; M206I; R211K; I226V; | ++++++[4] |

[1] Modified final assay conditions: [compound (2)] = 4 g/L, [NADP] = 0.5 g/L, Solvent = toluene:IPA:acetone:buffer (100 mM TEA buffer, pH 7.0 containing 1 mM MgSO$_4$) in relative % volumes of 30:18:2:50; plate shaken for 2 h at RT.
[2] Modified final assay conditions: [compound (2)] = 50 g/L, [NADP] = 0.1 g/L, Solvent = toluene:IPA:acetone:buffer (100 mM TEA buffer, pH 7.0 containing 1 mM MgSO$_4$) in relative % volumes of 30:18:2:50; plate shaken for 24 h at 30° C.
[3] Modified final assay conditions: [compound (2)] = 4 g/L, [NADP] = 0.1 g/L, Solvent = (IPA + acetone):buffer (100 mM TEA buffer, pH 7.0 containing 1 mM MgSO$_4$) in relative % volumes of 70:30; plate shaken for 24 h at RT.
[4] Modified final assay conditions: [compound (2)] = 80 g/L, [NADP] = 0.1 g/L, Solvent = (IPA + acetone):buffer (100 mM TEA buffer, pH 7.0 containing 1 mM MgSO$_4$) in relative % volumes of 65:35; plate shaken for 24 h at RT.

In some embodiments, the non-naturally occurring polypeptides of the present disclosure which are capable of converting compound (2) to compound (1) comprising an amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168. As shown above in Table 2, each of these polypeptides comprises one or more amino acid residue differences as compared to SEQ ID NO: 2, and has at least 2-fold, at least 10-fold, at least 25-fold, at least 40-fold, or at least 60-fold increased activity relative to the activity of the reference polypeptide of SEQ ID NO: 2. Specific amino acid differences are shown in Table 2 and include one or more residue differences as compared to SEQ ID NO:2 at the following residue positions: X21, X25, X40, X64, X93, X94, X95, X96, X99, X108, X117, X127, X147, X148, X150, X152, X153, X155, X190, X195, X196, X201, X202, X203, X204, X205, X206, X207, X211, X221, X223, and X226.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, and further comprises a set of amino acid residue differences as compared to SEQ ID NO:2 of any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168. In some embodiments, in addition to the set of amino acid residue differences of any one of the non-naturally occurring polypeptides of SEQ ID NO: 4 through SEQ ID NO: 168, the sequence of the non-naturally occurring polypeptide can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the SEQ ID NO: 2. In some embodiments, the residue differences can comprise conservative substitutions and non-conservative substitutions as compared to SEQ ID NO: 2.

The present disclosure also contemplates a non-naturally occurring polypeptide capable of converting compound (2) to compound (1) with improved properties relative to the activity of the polypeptide of SEQ ID NO: 2, wherein the non-naturally occurring polypeptide comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, and further comprises a set of amino acid residue differences as compared to SEQ ID NO:2, wherein the amino acid differences are based on locations or regions in the structure of reference polypeptide (e.g., SEQ ID NO: 2) and/or the associated function properties. Accordingly, referring to Table 3, a non-naturally occurring or engineered ketoreductase polypeptide of the present disclosure can include an amino acid substitution at a particular residue at a location in the structure of the reference polypeptide as identified in Table 3. Exemplary substitutions at each of the relevant locations include those identified in Table 2.

TABLE 3

Structural locations useful for engineered ketoreductase polypeptides

| Position | Structural location | Associated functional properties |
|---|---|---|
| X21 | Surface | Thermostability |
| X25 | Surface | Solvent stability |
| X40 | NADPH-Binding Site | Tight binding of NADPH to enzyme |
| X64 | NADPH-Binding Site | Interacts with NADPH Adenine ring |
| X93 | Second sphere active site | Thermostability |
| X94 | Second sphere active site | Thermostability |
| X95 | Second sphere active site | Activity |
| X96 | Second sphere active site | Activity |
| X99 | Dimer-tetramer interface | Thermostability/Solvent stability |
| X108 | Dimer-tetramer interface | Thermostability/Solvent stability |
| X117 | Core | Thermostability/Solvent stability |
| X127 | Second sphere active site | Thermostability/Solvent stability |
| X147 | Dimer-tetramer interface | Thermostability/Solvent stability |
| X148 | Dimer-tetramer interface | Thermostability/Solvent stability |
| X150 | Active site | Activity |
| X152 | Second sphere active site | Activity |
| X153 | Second sphere active site | Activity |
| X155 | Position interacting with 95 | Activity |
| X190 | Active site | Activity |
| X195 | Second sphere active site | Thermostability |
| X196 | Active site | Activity |
| X201 | Active site | Activity |
| X202 | Flexible loop | Activity |
| X203 | Flexible loop | Activity |
| X204 | Flexible loop | Activity |
| X205 | Flexible loop | Activity |
| X206 | Flexible loop | Activity |
| X207 | Flexible loop | Activity |
| X211 | Second sphere active site | Activity |
| X221 | Surface | Thermostability/Solvent stability |
| X223 | Core | Thermostability/Solvent stability |
| X226 | Dimer-tetramer interface | Thermostability/Solvent stability |

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2 and at least the following features: residue at position corresponding to X40 is R; residue at position corresponding to X153 is I, or L; residue at position corresponding to X190 is A or P; residue at position corresponding to X196 is T; residue at position corresponding to X199 is F, or W; and residue at position corresponding to X206 is I. In some embodiments, the amino acid sequence further comprises at least one feature or group of features selected from: (a) residue at position X93 is A and residue at position X94 is T; (b) residue at position X93 is A and residue at position X94 is S; (c) residue at position X93 is A and residue at position X94 is S; (d) residue at position X93 is I and residue at position X94 is S; (e) residue at position X203 is G; (f) residue at position X202 is G and residue at position X203 is G; or (f) residue at position X201 is A, residue at position X202 is G, and residue at position X203 is G.

In some embodiments, any of the non-naturally occurring polypeptides of the present disclosure capable of converting compound (2) to compound (1) with at least 2-fold, at least 10-fold, at least 25-fold, at least 40-fold, or at least 60-fold increased activity relative to the activity of the polypeptide of SEQ ID NO: 2 and an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, can further one or more features selected from: residue at position corresponding to X21 is R or F; residue at position corresponding to X25 is R, T, or N; residue at position corresponding to X40 is R; residue at position corresponding to X64 is V; residue at position corresponding to X93 is A; residue at position corresponding to X94 is T, S, or P; residue at position corresponding to X95 is V, or M; residue at position corresponding to X96 is V, G, A, N, S, P, or T; residue at position corresponding to X99 is L; residue at position corresponding to X108 is H; residue at position corresponding to X117 is A, or G; residue at position corresponding to X127 is K, or Q; residue at position corresponding to X147 is M, or I; residue at position corresponding to X148 is I; residue at position corresponding to X150 is H, or A; residue at position corresponding to X152 is N, or F; residue at position corresponding to X153 is I, or L; residue at position corresponding to X155 is C; residue at position corresponding to X190 is A; residue at position corresponding to X195 is M; residue at position corresponding to X196 is T, A, S, C, or N; residue at position corresponding to X199 is F, or W; residue at position corresponding to X201 is I, L, or A; residue at position corresponding to X202 is L, N, V, or G; residue at position corresponding to X203 is G; residue at position corresponding to X204 is V, or A; residue at position corresponding to X205 is V; residue at position corresponding to X206 is I; residue at position corresponding to X207 is T, C, I, or N; residue at position corresponding to X211 is K; residue at position corresponding to X221 is D; residue at position corresponding to X223 is I; residue at position corresponding to X226 is V.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, and at least the following features: residue at position corresponding to X40 is R; residue at position corresponding to X153 is I, or L; residue at position corresponding to X190 is A or P; residue at position corresponding to X196 is T; residue at position corresponding to X199 is F, or W; and residue at position corresponding to X206 is I, wherein the amino acid sequence further comprises at least one of the following sets of features (a) through (h):

(a) residue at position corresponding to X40 is R; residue at position corresponding to X93 is A; residue at position corresponding to X94 is T; residue at position corresponding to X153 is I; residue at position corresponding to X190 is A; residue at position corresponding to X196 is T; residue at position corresponding to X199 is F; residue at position corresponding to X203 is G; and residue at position corresponding to X206 is I; or (b) residue at position corresponding to X40 is R; residue at position corresponding to X93 is A; residue at position corresponding to X94 is S; residue at position corresponding to X96 is N; residue at position corresponding to X153 is L; residue at position corresponding to X190 is A; residue at position corresponding to X196 is T; residue at position corresponding to X199 is F; residue at position corresponding to X202 is G; residue at position corresponding to X203 is G; and residue at position corresponding to X206 is I; or (c) residue at position corresponding to X40 is R; residue at position corresponding to X93 is A; residue at position corresponding to X94 is S; residue at position corresponding to X96 is A, P, or N; residue at position corresponding to X153 is L; residue at position corresponding to X190 is A; residue at position corresponding to X196 is T; residue at position corresponding to X199 is F; residue at position corresponding to X202 is G; residue at position corresponding to X203 is G; and residue at position corresponding to X206 is I; and, optionally further comprises: residue at position corresponding to X96 is N; and residue at position corresponding to X201 is I, or L; or (d) residue at position corresponding to X40 is R; residue at position corresponding to X93 is A; residue at position corresponding to X96 is P; residue at position corresponding to X153 is L; residue at position corresponding to X190 is A; residue at position corresponding to X196 is T; residue at position corresponding to X199 is F; residue at position corresponding to X202 is G; residue at position corresponding to X203 is G; and residue at position corresponding to X206 is I; and optionally further comprises: residue at position corresponding to X21 is F; residue at position corresponding to X25 is R; residue at position corresponding to X94 is S; residue at position corresponding to X96 is P; residue at position corresponding to X108 is K; residue at position corresponding to X127 is K; residue at position corresponding to X147 is M; residue at position corresponding to X153 is L; residue at position corresponding to X205 is V; residue at position corresponding to X211 is K; and residue at position corresponding to X221 is D; or (e) residue at position corresponding to X21 is F; residue at position corresponding to X25 is R; residue at position corresponding to X40 is R; residue at position corresponding to X93 is A; residue at position corresponding to X94 is S; residue at position corresponding to X96 is P; residue at position corresponding to X108 is K; residue at position corresponding to X127 is K; residue at position corresponding to X147 is M; residue at position corresponding to X153 is L; residue at position corresponding to X190 is A; residue at position corresponding to X196 is T; residue at position corresponding to X199 is F; residue at position corresponding to X202 is G; residue at position corresponding to X203 is G; residue at position corresponding to X206 is I; and residue at position corresponding to X221 is D; or (f) residue at position corresponding to X40 is R; residue at position corresponding to X93 is I; residue at position corresponding to X94 is S; residue at position corresponding to X96 is P; residue at position corresponding to X153 is L; residue at position corresponding to X190 is A; residue at position corresponding to X196 is T; residue at position corresponding to X199 is F, or W; residue at position corresponding to X201 is A; residue at position corresponding to X202 is G; residue at position corresponding to X203 is G; residue at position corresponding to X206 is I; and residue at position corresponding to X211 is K; and optionally further comprises: residue at position corresponding to X64 is V; residue at position corresponding to X99 is L; residue at position corresponding to X108 is H; residue at position corresponding to X117 is A, or G; residue at position corresponding to X147 is I, or M; residue at position corresponding to X195 is M; residue at position corresponding to X205 is V; residue at position corresponding to X223 is I; and residue at position corresponding to X226 is V; or (g) residue at position corresponding to X40 is R; residue at position corresponding to X93 is I; residue at position corresponding to X94 is S; residue at position corresponding to X96 is P; residue at position corresponding to X99 is L; residue at position corresponding to X108 is H; residue at position corresponding to X117 is G; residue at position corresponding to X147 is I; residue at position corresponding to X153 is L; residue at position corresponding to X190 is A; residue at position corresponding to X196 is T; residue at position corresponding to X199 is F; residue at position corresponding to X201 is A; residue at position corresponding to X202 is G; residue at position corresponding to X203 is G; residue at position corresponding to X206 is I; residue at position corresponding to X211 is K; and residue at position corresponding to X226 is V; or (h) residue at position corresponding to X40 is R; residue at position corresponding to X64 is V; residue at position corresponding to X93 is I; residue at position corresponding to X94 is S; residue at position corresponding to X96 is P; residue at position corresponding to X99 is L; residue at position corresponding to X108 is H; residue at position corresponding to X117 is G; residue at position corresponding to X147 is I; residue at position corresponding to X153 is L; residue at position corresponding to X190 is A; residue at position corresponding to X196 is T; residue at position corresponding to X199 is W; residue at position corresponding to X201 is A; residue at position corresponding to X202 is G; residue at position corresponding to X203 is G; residue at position corresponding to X206 is I; residue at position corresponding to X211 is K; and residue at position corresponding to X226 is V.

In some embodiments, the non-naturally occurring polypeptides of the present disclosure can comprise a sequence having one or more amino acid residue differences as compared to SEQ ID NO: 2 at residue positions affecting activity for conversion of compound (2) to compound (1), which positions include the following: X21; X25; X64; X93; X94; X95; X96; X99; X108; X117; X127; X147; X148; X150; X152; X153; X155; X163; X190; X195; X196; X199; X201; X202; X203; X204; X205; X206; X207; X211; X221; X223; and X226. In some embodiments, the specific amino acid differences resulting in increased activity for conversion of compound (2) to compound (1) relative to the reference polypeptide of SEQ ID NO: 2 can be selected from the following: residue at position corresponding to X21 is F or R; residue at position corresponding to X25 is N, R, or T; residue at position corresponding to X64 is V; residue at position corresponding to X93 is A or T; residue at position corresponding to X94 is P, S, or T; residue at position corresponding to X95 is M or V; residue at position corresponding to X96 is A, N, G, P, S, T, or V; residue at position corresponding to X99 is L; residue at position corresponding to X108 is D, H, or K; residue at position corresponding to X117 is A or G; residue at position corresponding to X127 is K or Q; residue at position corresponding to X147 is I or M; residue at position corresponding to X148 is I; residue at position corresponding to X150 is H; residue at position corresponding to X152 is N or F; residue at position corresponding to X153 is I or L; residue at position corresponding to X155 is C; residue at position corresponding to X163 is I; residue at position corresponding to X190 is A; residue at position corresponding to X195 is M; residue at position corresponding to X196 is A, C, N, S, or T; residue at position corresponding to X199 is F or W; residue at position corresponding to X201 is A, I, or L; residue at position corresponding to X202 is G, L, N, or V; residue at position corresponding to X203 is G; residue at position corresponding to X204 is A or V; residue at position corresponding to X205 is V; residue at position corresponding to X206 is I; residue at position corresponding to X207 is C, I, N, or T; residue at position corresponding to X211 is K; residue at position corresponding to X221 is D; residue at position corresponding to X223 is I; and residue at position corresponding to X226 is V.

In some embodiments, the non-naturally occurring polypeptides capable of converting compound (2) to compound (1) can have increased thermostability as compared to the polypeptide of SEQ ID NO: 2 (or another reference polypeptide, e.g., SEQ ID NO: 80 or 100). Thermostability can be determined by preincubating the polypeptide at a defined temperature and time, e.g., 4° C.-46° C. for 18-24 hours, followed by measuring the % residual activity using a defined assay. Exemplary preincubation conditions include preincubation at 30° C. for 18 h, or 40° C. for 24 h. Accordingly, in some embodiments, the non-naturally occurring polypeptides of the present disclosure can comprise an amino acid sequence having one or more residue differences as compared to SEQ ID NO: 2 at residue positions affecting thermostability, which positions include the following: X21; X93; X94; X117; X127; X147; X195; and X199. In some embodiments, specific amino acid differences resulting in increased thermostability relative to the reference polypeptide of SEQ ID NO: 2 can be selected from the following substitutions: residue at position corresponding to X21 is F; residue at position corresponding to X93 is T; residue at position corresponding to X94 is A; residue at position corresponding to X117 is G or A; residue at position corresponding to X127 is K; residue at position corresponding to X147 is I; residue at position corresponding to X195 is M; and residue at position corresponding to X199 is W.

In some embodiments, the present disclosure provides non-naturally occurring polypeptides capable of converting compound (2) to compound (1) and having at least 1.5-fold, 2.5-fold, 5-fold, 7.5-fold or more increased thermostability following 18 h preincubation at 40° C. as compared to the polypeptide of SEQ ID NO: 80 or SEQ ID NO: 100, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 80 or SEQ ID NO: 100, and at least one of the following substitutions: residue at position corresponding to X21 is F; residue at position corresponding to X93 is T; residue at position corresponding to X94 is A; residue at position corresponding to X117 is G or A; residue at position corresponding to X127 is K; residue at position corresponding to X147 is I; residue at position corresponding to X195 is M; and residue at position corresponding to X199 is W.

In some embodiments, the present disclosure provides non-naturally occurring polypeptides capable of converting compound (2) to compound (1) and having at least 1.5-fold, 2.5-fold, 5-fold, 7.5-fold or more increased thermostability following 18 h preincubation at 40° C. as compared to the polypeptide of SEQ ID NO: 80 or SEQ ID NO: 100, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 80 or SEQ ID NO: 100, and the set of amino acid residue differences of any one of the non-naturally occurring polypeptides of SEQ ID NOs: 134, 136, 140, 142, 144, 152, 154, 156, 158, 160, 162, 164, or 166.

In some embodiments, the non-naturally occurring polypeptides of the present disclosure can comprise an amino acid sequence having residue differences as compared to SEQ ID NO: 2 at residue positions affecting solvent stability, which positions include the following: X25; X147; and X221. In some embodiments, specific amino acid differences resulting in increased solvent stability relative to the reference polypeptide of SEQ ID NO: 2 (e.g., increased activity relative to SEQ ID NO: 2 in up to 65% isopropanol) can be selected from the following substitutions: residue at position corresponding to X25 is R; residue at position corresponding to X147 is M; and residue at position corresponding to X221 is D.

In some embodiments, the non-naturally occurring polypeptides of the present disclosure can comprise an amino acid sequence having residue differences as compared to SEQ ID NO: 2 at residue positions affecting cofactor binding, which positions include X40. In some embodiments, specific amino acid differences affecting cofactor binding can be selected from the following: residue at position corresponding to X40 is R.

As will be apparent to the skilled artisan, various combinations of residue differences as compared to SEQ ID NO:2 at residue positions affecting enzymatic activity, thermostability, solvent stability, and cofactor binding can be made to form the polypeptides of the present disclosure.

In addition to the residue positions specified above, any of the non-naturally occurring ketoreductase polypeptides disclosed herein can further comprise other residue differences relative to SEQ ID NO:2 at other residue positions. Residue differences at these other residue positions provide for additional variations in the amino acid sequence without adversely affecting the ability of the polypeptide to carry out the conversion of compound (2) to compound (1). In some embodiments, the polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, and 40 residue differences at other residue positions. The residue difference at these other positions can include conservative changes or non-conservative changes. In some embodiments, the residue differences can comprise conservative substitutions and non-conservative substitutions as compared to the wild-type ketoreductase of SEQ ID NO: 2.

Amino acid residue differences at other positions relative to SEQ ID NO: 2 or the wild-type *L. kefir* ketoreductase sequence (Genbank acc. No. AAP94029.1; GI: 33112056) and the affect of these differences on enzyme function are provide by e.g., engineered ketoreductase polypeptides in the following patent publications, each of which is hereby incorporated by reference herein: US 20080318295A1; US 20090093031A1; US 20090155863A1; US 20090162909A1; US 20090191605A1; US 20100055751A1; WO/2010/025238A2; WO/2010/025287A2; and US 20100062499A1. Accordingly, in some embodiments, one or more of the amino acid differences provided in the engineered ketoreductase polypeptides of these publications could also be introduced into a non-naturally occurring polypeptide of the present disclosure.

In some embodiments, the present disclosure provides a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, with the proviso that the amino acid sequence of any one or more of the ketoreductase polypeptides disclosed in any one or more of the following patent publications are excluded: US 20080318295A1; US 20090093031A1; US 20090155863A1; US 20090162909A1; US 20090191605A1; US 20100055751A1; WO/2010/025238A2; WO/2010/025287A2; US 20100062499A1; and WO 2008/151324A1.

In some embodiments, the polypeptides can comprise deletions of the engineered ketoreductase polypeptides described herein. Thus, for each and every embodiment of the polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids of the polypeptides, as long as the functional activity of the polypeptide with respect to the conversion of compound (2) to compound (1) is present. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35, or 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

In some embodiments, the polypeptides can comprise fragments of the engineered polypeptides described herein. In some embodiments, the fragments can have about 80%, 90%, 95%, 98%, and 99% of the full-length polypeptide, e.g., the polypeptide of SEQ ID NO:2, as long as the functional activity of the polypeptide with respect to the conversion of compound (2) to compound (1) is present.

In some embodiments, the polypeptides of the disclosure can be in the form of fusion polypeptides in which the engineered polypeptides are fused to other polypeptides, such as, by way of example and not limitation, antibody tags (e.g., myc epitope), purifications sequences (e.g., His tags for binding to metals), and cell localization signals (e.g., secretion signals). Thus, the engineered polypeptides described herein can be used with or without fusions to other polypeptides.

As will be understood by the skilled artisan, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (PH); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys(nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr(O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the polypeptides can be provided on a substrate. In some embodiments, the polypeptides can be provided in the form of an array in which the polypeptides are arranged in positionally distinct locations. The array can be used to test a variety of aryl alkyl sulfides for conversion by the polypeptides. "Substrate," "support," "solid support," "solid carrier," or "resin" in the context of arrays refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

In certain embodiments, the kits of the present disclosure include arrays comprising a plurality of different engineered ketoreductase polypeptides at different addressable position, wherein the different polypeptides are different variants of a reference sequence each having at least one different improved enzyme property. Such arrays comprising a plurality of engineered polypeptides and methods of their use are described in, e.g., WO2009/008908A2.

5.4 Ketoreductase Polynucleotides, Expression Vectors, and Host Cells

In another aspect, the present disclosure provides polynucleotides encoding the non-naturally occurring or engineered polypeptides described herein. These polynucleotides may be operatively linked to one or more heterologous regulatory sequences that control gene expression to create a recombinant polynucleotide capable of expressing the ketoreductase polypeptide. Expression constructs containing a heterologous polynucleotide encoding the engineered ketoreductase polypeptide can be introduced into appropriate host cells to express the corresponding polypeptide.

Because of the knowledge of the codons corresponding to the various amino acids, availability of a protein sequence provides a description of all the polynucleotides capable of encoding the subject. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

Since not all codons need to be replaced to optimize the codon usage of the ketoreductases (e.g., because the natural sequence can have preferred codons and because use of preferred codons may not be required for all amino acid residues), codon optimized polynucleotides encoding the ketoreductase polypeptides may contain preferred codons at about 40%, 50%, 60%, 70%, 80%, or greater than 90% of codon positions of the full length coding region.

In some embodiments, the polynucleotide encodes a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the polynucleotide encodes a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168, with the proviso that the amino acid sequence comprises any one of the set of residue differences as compared to SEQ ID NO: 2 contained in any one of the polypeptide sequences of SEQ ID NO:4 to SEQ ID NO:168 listed in Table 2.

In some embodiments, the polynucleotides encoding the polypeptides are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, and 167.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167, or a complement thereof, where the highly stringently hybridizing polynucleotides encode a non-naturally occurring polypeptide capable of converting compound (2) to compound (1) with at least 2-fold, at least 10-fold, at least 25-fold, at least 40-fold, or at least 60-fold increased activity relative to the activity of the polypeptide of SEQ ID NO: 2.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase polypeptides described herein. In some embodiments, the reference polynucleotide is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, and 167.

An isolated polynucleotide encoding a non-naturally occurring polypeptide of the disclosure may be manipulated in a variety of ways to provide for expression of the polypeptide. In some embodiments, the polynucleotides encoding the polypeptides can be provided as expression vectors where one or more control sequences is present to regulate the expression of the polynucleotides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoters, leader sequence, polyadenylation sequence, propeptide sequence, signal peptide sequence, and transcription terminator. Suitable promoters can be selected based on the host cells used. Exemplary bacterial promoters include *E. coli* lac operon, *E. coli* trp operon, bacteriophage 1, *Streptomyces coelicolor* agarase gene (dagA), *Bacillus subtilis* levansucrase gene (sacB), *Bacillus licheniformis* alpha-amylase gene (amyL), beta-lactamase gene, and tac promoter; exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease, and mutant, truncated, and hybrid promoters thereof, and exemplary yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase.

In some embodiments, the control sequence may also be a signal peptide coding region that codes for an amino acid sequence linked to the amino terminus of a polypeptide and directs the encoded polypeptide into the cell's secretory pathway. The signal sequence typically depends on the type of host cells being used to express the polypeptide. Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Exemplary signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

Other control sequences, such as leader sequence, polyadenylation sequence, and transcription terminator sequences can use those available in the art (see Sambrook, supra, and Current Protocols in Molecular Biology, supra).

In another aspect, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The expression vector preferably contains one or more selectable markers, which permit easy selection of transformed cells. A selectable marker is a gene the product of which provides for biocide or viral resistance, resistance to heavy metals, prototrophy to auxotrophs, resistance to chemical agents (e.g., antibiotics) and the like.

In another aspect, the present disclosure provides a host cell comprising a polynucleotide encoding an engineered ketoreductase polypeptide of the present disclosure, the polynucleotide being operatively linked to one or more control sequences for expression of the ketoreductase polypeptide in the host cell. Host cells for use in expressing the ketoreductase polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells; insect cells such as *Drosophila* S2 and *Spodoptera* Sf9 cells; animal cells such as CHO, COS, BHK, 293, and Bowes melanoma cells; and plant cells. Exemplary host cells are *Escherichia coli* BL21 and W3110.

Appropriate culture mediums and growth conditions for the above-described host cells are well known in the art. Polynucleotides for expression of the ketoreductase may be introduced into host cells by various methods known in the art (e.g., electroporation, biolistic particle bombardment, liposome mediated transfection, calcium chloride transfection, and protoplast fusion).

In the embodiments herein, the non-naturally occurring or engineered ketoreductase polypeptides and nucleotides encoding such polypeptides can be prepared using methods commonly used by those skilled in the art. As noted above, the naturally-occurring amino acid sequence and corresponding polynucleotide encoding the ketoreductase enzyme of *Lactobacillus kefir*. In some embodiments, the parent polynucleotide sequence is codon optimized to enhance expression of the ketoreductase in a specified host cell.

The engineered ketoreductase polypeptides can be obtained by subjecting the polynucleotide encoding the naturally occurring ketoreductase to mutagenesis and/or directed evolution methods (see e.g., Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; U.S. Pat. Nos. 6,537,746, 6,117,679, 6,376,246, and 6,586,182; and U.S. Pat. Publ. Nos. 20080220990A1 and 20090312196A1; each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, Methods Mol. Biol. 57:369-74; Smith, 1985, Ann. Rev. Genet. 19:423-462; Botstein et al., 1985, Science 229:1193-1201; Carter, 1986, "Site-directed mutagenesis," Biochem. J. 237:1-7; Kramer et al., 1984, Cel1138:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; and Stemmer, 1994, Nature 370:389-391. All publications are incorporated herein by reference.

In some embodiments, the clones obtained following mutagenesis treatment are screened for non-naturally occurring ketoreductases having a desired enzyme property. Measuring ketoreductase enzyme activity from the expression libraries can be performed using the standard techniques, such as separation of the product (e.g., by HPLC) and detection of the product by measuring UV absorbance of the separated substrate and products and/or by detection using tandem mass spectroscopy (e.g., MS/MS). Clones containing a polynucleotide encoding the desired engineered polypeptides are then isolated, sequenced to identify the nucleotide sequence changes (if any), and used to express the enzyme in a host cell. Exemplary assays are provided below in Example 3.

Where the sequence of the polypeptide is known, the polynucleotides encoding the enzyme can be prepared by standard solid-phase methods, according to known synthetic methods, e.g., the classical phosphoramidite method described by Beaucage et al., 1981, Tet Lett 22:1859-69, or the method described by Matthes et al., 1984, EMBO J. 3:801-05. In some embodiments, fragments of up to about 100 bases can be individually synthesized, then joined (e.g., by enzymatic or chemical litigation methods, or polymerase mediated methods) to form any desired continuous sequence.

In some embodiments, the present disclosure also provides methods for preparing or manufacturing the non-naturally occurring polypeptides capable of converting compound (2) to compound (1), wherein the methods comprise: (a) culturing a host cell capable of expressing a polynucleotide encoding the non-naturally occurring polypeptide and (b) isolating the polypeptide from the host cell. The non-naturally occurring polypeptides can be expressed in appropriate cells (as described above), and isolated (or recovered) from the host cells and/or the culture medium using any one or more of the well known techniques used for protein purification, including, among others, lysozyme treatment, sonication, filtration, salting-out, ultra-centrifugation, and chromatography. Chromatographic techniques for isolation of the ketoreductase polypeptide include, among others, reverse phase chromatography high performance liquid chromatography, ion exchange chromatography, gel electrophoresis, and affinity chromatography.

In some embodiments, the non-naturally occurring polypeptide of the disclosure can be prepared and used in various isolated forms including but not limited to crude extracts (e.g., cell-free lysates), powders (e.g., shake-flask powders), lyophilizates, and substantially pure preparations (e.g., DSP powders), as further illustrated in the Examples below.

In some embodiments, the non-naturally occurring polypeptide of the disclosure can be prepared and used in purified form. Generally, conditions for purifying a particular enzyme will depend, in part, on factors such as net charge, hydrophobicity, hydrophilicity, molecular weight, molecular shape, etc., and will be apparent to those having skill in the art. To facilitate purification, it is contemplated that in some embodiments the engineered ketoreductase polypeptides of the present disclosure can be expressed as fusion proteins with purification tags, such as His-tags having affinity for metals, or antibody tags for binding to antibodies, e.g., myc epitope tag.

5.5 Methods of Use

The engineered ketoreductase polypeptides described herein can be used in processes comprising the conversion of compound (2) to compound (1) as shown in Scheme 1, for example in process for manufacturing compound (1), which is used as the active pharmaceutical ingredient, Ezetimibe. Furthermore, the biocatalytic abilities of the non-naturally occurring ketoreductase polypeptides disclosure are not limited to the conversion of compound (2) to compound (1). Additionally, the engineered ketoreductase polypeptides described herein can be used for the conversion of analogs of compound (2) to the corresponding chiral alcohol analogs of compound (1) in diastereomeric excess.

In some embodiments, the disclosure provides methods for preparing compound (1) or an analog of compound (1) in diastereomeric excess comprising: contacting compound (2) or an analog of compound (2) with an engineered polypeptide of the present disclosure (e.g., as described in Table 2 and elsewhere herein) in the presence of NADPH or NADH cofactor under suitable reaction conditions. Suitable reactions conditions for the conversion of compound (2) to compound (1), or the conversion of an analog of compound (2) to the corresponding analog of compound (1), using the engineered polypeptides of the present disclosure are described in greater detail below and some exemplary suitable reaction conditions also are provided in the Examples.

The engineered polypeptides of the present disclosure of improved enzymatic properties for the conversion of compound (2) to compound (1) relative to the naturally occurring ketoreductase polypeptide of SEQ ID NO: 2, including increased conversion rates, increased stereoselectivity (resulting in compound (1) in greater diastereomeric excesses), increased solvent stability, and increased thermal stability. Accordingly, it is contemplated that any of the engineered polypeptides disclosed herein may be used in improved methods that comprise the conversion of compound (2) to compound (1). For example, in some embodiments, the methods of the present disclosure can be carried out wherein the engineered polypeptide is selected from an amino acid sequence having at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identity to SEQ ID NO: 2, which further comprises the combination of residue differences compared to SEQ ID NO: 2 of any one of engineered polypeptides disclosed in Table 2 (e.g., even-numbered SEQ ID NOs: 4-168). In some embodiments, the any one or more of the polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168 may be used in the methods disclosed herein.

The present disclosure also contemplates ranges of suitable reaction conditions that can be used in the methods, including but not limited to ranges of pH, temperature, buffer, solvent system, substrate loading, polypeptide loading, cofactor loading, atmosphere, and reaction time. The present disclosure also contemplates that the methods comprising the biocatalytic conversion compound (2) to compound (1) using an engineered polypeptide of the disclosure can further comprise chemical steps of compound (1) product work-up, extraction, isolation, purification, and/or crystallization, each of which can be carried out under a range of conditions.

In some embodiments, the methods for preparing compound (1) of the present disclosure can be carried out wherein the reaction conditions comprise compound (2) substrate loading of at least about 20 g/L, about 40 g/L, about 50 g/L, about 75 g/L, about 100 g/L, about 200 g/L, about 250 g/L, about 300 g/L, about 400 g/L, or even greater. In certain embodiments, methods for preparing compound (1) of the present disclosure can be carried out wherein the reaction conditions comprise compound (2) substrate loading of about 50-100 g/L, about 50-200 g/L, about 50-300 g/L, about 50-400 g/L, about 100 g/L, about 200 g/L, about 300 g/L or about 400 g/L. The values for substrate loadings provided herein are based on the molecular weight of compound (2), however it also contemplated that the equivalent molar amounts of various hydrates and salts of compound (2) also can be used in the methods.

The improved enzymatic activity of the engineered polypeptides of the present disclosure in the conversion of compound (2) to compound (1) provides for methods wherein higher percentage conversion can be achieved with lower concentrations of the engineered polypeptide. The use of lower concentration of the engineered polypeptide in a method comprising a conversion of compound (2) to compound (1) also reduces the amount of residual protein that may need to be removed in subsequent steps for purification of compound (1). In some embodiments, the methods for preparing compound (1) of the present disclosure can be carried out wherein the reaction conditions comprise an engineered polypeptide concentration of about 0.1-3.0 g/L, about 0.5-2.75 g/L, about 1.0-2.5 g/L, about 1.5-2.5 g/L, about 3 g/L, about 2 g/L, about 1.5 g/L, about 1.0 g/L, about 0.75 g/L, or even lower concentration.

In certain embodiments, the temperature of the suitable reaction conditions can be chosen to maximize the reaction rate at higher temperatures while maintaining the activity of the enzyme for sufficient duration for efficient conversion of the substrate to the product. Where higher temperatures are used, polypeptides with increased thermostability can be selected to carry out the process.

The engineered polypeptides of the present disclosure have increased thermal stability relative to the naturally occurring ketoreductase polypeptide of SEQ ID NO: 2. This allows the engineered polypeptides to be used in methods for converting compound (2) to compound (1) at higher temperatures which can result in increased conversion rates and improved substrate solubility characteristics for the reaction, although substrate or product degradation at higher temperatures can contribute to decreased process yields. In certain embodiments, the method can be carried out wherein the reaction conditions comprise a temperature of about 20° C. to about 40° C., about 23° C. to about 37° C., about 25° C. to about 35° C., about 26° C. to about 32° C., or about 28° C. to about 30° C. In certain embodiments, the temperature during the enzymatic reaction can be maintained at ambient (e.g., 25° C.), 27° C., 30° C., 32° C., 35° C., 37° C., 40° C.; or in some embodiments adjusted over a temperature profile during the course of the reaction.

In certain embodiments, the methods for preparing compound (1) of the present disclosure the pH of the reaction mixture may be maintained at a desired pH or within a desired pH range by the addition of an acid or a base during the course of the reaction. In certain embodiments, the pH of the reaction mixture may change or be changed during the course of the reaction. Thus, it is contemplated that in some embodiments the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

In certain embodiments, the methods for preparing compound (1) of the present disclosure can be carried out wherein the reaction conditions comprise a pH of about 6.0 to about 7.5, a pH of about 6.25 to about 7.25, a pH of about 6.5 to about 7.25, a pH of about 6.6 to about 7.25, a pH of about 6.6 to about 7.0, a pH of about 6.75 to about 7.25, or a pH of about 6.75. Below pH 6.5 the rate of the biocatalytic conversion of compound (2) to compound (1) slows down and consequently a longer overall reaction time (e.g., >24 h) may be needed to achieve a high level of conversion (e.g., >97%). Also, NADP+ cofactor is less stable below pH 6.25. Above pH 7.25 the degradation of the compound (2) and compound (1) increases, which may result in decreased overall yield and purity of compound (1) made according to the method.

The methods for preparing compound (1) of the present disclosure are generally carried out in a solvent. Suitable solvents include water, aqueous buffer solutions, organic solvents, and/or co-solvent systems, which generally comprise aqueous solvents and organic solvents.

In certain embodiments, the methods for preparing compound (1) of the present disclosure can be carried out wherein the reaction conditions comprise a solution comprising an aqueous buffer solution, an organic solvent, or a co-solvent system. In some embodiments, the buffer solution is selected from TEA (e.g., about 0.025 M to about 0.25 M TEA) and potassium phosphate (e.g., about 0.025 M to about 0.25 M phosphate). In certain embodiments, the co-solvent system comprises about 30% (v/v) to about 70% (v/v) of an aqueous buffer solution (e.g., about 0.1 M TEA) and about 70% to about 30% of an organic solvent solution (e.g., IPA and/or toluene). In some embodiments, the reaction conditions comprise water as a suitable solvent with no buffer present.

The engineered polypeptides of the present disclosure have increased stability to organic solvent relative to the naturally occurring ketoreductase polypeptide of SEQ ID NO: 2. This allows the engineered polypeptides to be used in methods for converting compound (2) to compound (1) in co-solvent systems with higher concentrations of organic solvent which can result in improved product solubility characteristics and increased percent conversion (e.g., 97% or greater conversion of compound (2), at 100 g/L concentration, to compound (1) in 24 h).

In another embodiment, the co-solvent system comprises an aqueous buffer solution and IPA, wherein the IPA concentration is about 25-75% (v/v), about 35-75% (v/v), about 45-75% (v/v), about 55-75% (v/v), about 60-70% (v/v), about 62-68% (v/v), at least about 25% (v/v), at least about 35% (v/v), at least about 45% (v/v), at least about 55% (v/v), at least about 65% (v/v), about 60% (v/v), about 65% (v/v), or about 70% (v/v). In certain embodiments, the reaction conditions comprise a co-solvent system of 0.1 M TEA buffer and about 60% (v/v) to about 70% (v/v) IPA. In certain embodiments, the reaction conditions comprise a co-solvent system of about 35% (v/v) 0.1 M TEA buffer and about 65% (v/v) IPA.

In some embodiments, the co-solvent system comprises an aqueous buffer solution, IPA, and another organic solvent, such as toluene. In some embodiments, the co-solvent system comprises about 45-55% (v/v) of an aqueous buffer solution, about 25-35% (v/v) IPA, and about 25-35% (v/v) toluene. In certain embodiments, the co-solvent system comprises about 50% (v/v) of an aqueous buffer solution (e.g., 0.1 M TEA), about 20% (v/v) IPA, and about 30% (v/v) toluene.

In certain embodiments, the methods comprising the conversion of compound (2) to compound (1) can be carried out wherein the reaction conditions comprise an inert atmosphere (e.g., $N_2$, Ar, etc.).

In some embodiments, the methods for preparing compound (1) of the present disclosure can be carried out using a combination of any of the mixture and reaction conditions disclosed above or elsewhere herein, e.g., in the Examples. Accordingly, in some embodiments, the methods of the present disclosure can be carried out wherein the reaction conditions comprise: (1) substrate loading of about 50-200 g/L compound (2); (2) engineered polypeptide concentration of about 1.5-2.5 g/L; (3) NADPH cofactor concentration of about 0.1-0.2 g/L; (4) a co-solvent solution of an aqueous buffer and about 60-70% (v/v) IPA; (5) about pH 6.25-7.5; and (6) temperature of about 25-35° C.

In some embodiments, the methods for preparing compound (1) of the present disclosure can be carried out wherein the reaction conditions comprise: (1) substrate loading of about 100 g/L compound (2); (2) engineered polypeptide concentration of about 2.0 g/L; (3) NADPH cofactor concentration of about 0.1 g/L; (4) a co-solvent solution of an aqueous buffer of 0.1M TEA and about 65% (v/v) IPA; (5) about pH 6.75; and (6) temperature of about 30° C.

In some embodiments, the methods for preparing compound (1) of the present disclosure can be carried out wherein the reaction conditions comprise: (1) substrate loading of about 50-150 g/L of compound (2); (2) engineered polypeptide concentration of about 2.5-3.5 g/L; (3) NADPH cofactor concentration of about 0.1-0.2 g/L; (4) a co-solvent solution of an aqueous buffer and about 15-25% (v/v) IPA and 25-35% (v/v) toluene; (5) about a pH of 6.6-7.0; and (6) a temperature of about 28-30° C.

In some embodiments, the methods for preparing compound (1) of the present disclosure can be carried out wherein the reaction conditions comprise: (1) substrate loading of about 100 g/L of compound (2); (2) engineered polypeptide concentration of about 3.0 g/L; (3) NADPH cofactor concentration of about 0.1 g/L; (4) a co-solvent solution of an aqueous buffer of 0.1 M TEA and about 20% (v/v) IPA and 30% (v/v) toluene; (5) about a pH of 6.6-7.0; and (6) a temperature of about 28-30° C.

Generally, in the methods disclosed herein, the biocatalytic reaction with a polypeptide under suitable reaction conditions is allowed to proceed until essentially complete, or near complete, conversion of compound (2) to compound (1) is obtained. This conversion of substrate to product can be monitored using known methods by detecting substrate and/or product. Suitable methods include gas chromatography, HPLC, and the like, and are described in the Examples.

In some embodiments, the methods for preparing compound (1) of the present disclosure result in at least about 90% conversion of compound (2) at 100 g/L loading to compound (1) in 24 h, when carried out under reaction conditions of: engineered polypeptide concentration of about 1.0-3.0 g/L; NADPH cofactor concentration of about 0.1 g/L; a co-solvent system of at least 65% (v/v) IPA; and a temperature of 30° C. In some embodiments, the methods of the present disclosure when carried out under these reaction conditions (e.g., 100 g/L compound (2) loading) result in at least about 91%, 92%, 93%, 94%, 95%, 96%, 97%, 98%, 99% or greater conversion of compound (2) to compound (1) in 24 h.

In some embodiments, the methods for preparing compound (1) of the present disclosure when carried out with 100 g/L compound (2) loading result in an diastereomeric excess of compound (1) of at least 97%, 98, 99%, 99.1%, 99.2%, 99.3%, 99.4%, 99.5%, 99.6%, 99.7%, 99.8%, or 99.9% in 24 h.

In carrying out the conversion of compound (2) to compound (1) using the engineered polypeptides in the methods of the present disclosure, it is necessary for an electron donor to be present. Generally, a cofactor is used is used as the electron donor in the reduction reaction. The cofactor operates in combination with the polypeptides of the disclosure in the process. Suitable cofactors include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. Accordingly, in certain embodiments, the methods of the present disclosure are carried out wherein an electron donor is present selected from NADPH cofactor or NADH cofactor. In certain embodiments, the method can be carried out wherein the reaction conditions comprise an NADH or NADPH cofactor concentration of about 0.03-0.5 g/L, about 0.05-0.3 g/L, about 0.1-0.2 g/L, about 0.5 g/L, about 0.1 g/L, or about 0.2 g/L.

The reduced NAD(P)H form can be optionally regenerated from the oxidized $NAD(P)^+$ form using a cofactor regeneration system. In some embodiments of the process, a cofactor recycling system is used to regenerate cofactor NADPH/NADH form $NADP^+/NAD^+$ produced in the reaction.

In some embodiments of the process, an optional cofactor recycling system can be used to regenerate cofactor NADPH/NADH form NADP+/NAD+ produced in the reaction. A cofactor regeneration system refers to a set of reactants that participate in a reaction that reduces the oxidized form of the cofactor (e.g., $NADP^+$ to NADPH). Cofactors oxidized by the polypeptide reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either $NADP^+/NADPH$ or $NAD^+/NADH$ as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

In some embodiments, the cofactor recycling system can comprise glucose dehydrogenase (GDH), which is a $NAD^+$ or $NADP^+$-dependent enzyme that catalyzes the conversion of D-glucose and $NAD^+$ or $NADP^+$ to gluconic acid and NADH or NADPH, respectively. Glucose dehydrogenases suitable for use in the practice of the processes described herein include both naturally occurring glucose dehydrogenases, as well as non-naturally occurring glucose dehydrogenases. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring glucose dehydrogenases generated using, for example, mutagenesis, directed evolution, and the like and are provided in PCT publication WO 2005/018579, and US publication Nos. 2005/0095619 and 2005/0153417. All of these sequences are incorporated herein by reference.

In some embodiments, the co-factor regenerating system can comprise a formate dehydrogenase, which is a $NAD^+$ or $NADP^+$-dependent enzyme that catalyzes the conversion of formate and $NAD^+$ or $NADP^+$ to carbon dioxide and NADH or NADPH, respectively. Formate dehydrogenases that are suitable for use as cofactor regenerating systems in the ketoreductase reactions described herein include naturally occurring and non-naturally occurring formate dehydrogenases. Suitable formate dehydrogenases are described in PCT publication WO 2005/018579. Formate may be provided in the form of a salt, typically an alkali or ammonium salt (for example, $HCO_2Na$, $KHCO_2NH_4$, and the like), in the form of formic acid, typically aqueous formic acid, or mixtures thereof. A base or buffer may be used to provide the desired pH.

In some embodiments, the co-factor regenerating system can comprise a secondary alcohol dehydrogenase, which is an $NAD^+$ or $NADP^+$-dependent enzyme that catalyzes the conversion of a secondary alcohol and $NAD^+$ or $NADP^+$ to a ketone and NADH or NADPH, respectively. Secondary alcohol dehydrogenases suitable for use as cofactor regenerating systems in the processes described herein include naturally occurring and non-naturally occurring ketoreductases. Naturally occurring secondary alcohol dehydrogenases include known alcohol dehydrogenases from, *Thermoanerobium brockii*, *Rhodococcus erythropolis*, *Lactobacillus kefir*, and *Lactobacillus brevis*, and non-naturally occurring secondary alcohol dehydrogenases include engineered alcohol dehydrogenases derived therefrom. In some embodiments, non-naturally occurring ketoreductases engineered for thermo- and solvent stability can be used. Such ketoreductases are described in the present application and the patent publications US 20080318295A1; US 20090093031A1; US 20090155863A1; US 20090162909A1; US 20090191605A1; US 20100055751A1; WO/2010/025238A2; WO/2010/025287A2; and US 20100062499A1; each of which are incorporated by reference herein.

The engineered ketoreductase polypeptides of the present disclosure have improved enzymatic activity for the conversion of IPA to acetone relative to the naturally occurring ketoreductase polypeptide of SEQ ID NO: 2. Accordingly, in carrying out the conversion of compound (2) to compound (1) using the engineered polypeptides in the methods of the present disclosure, the NADPH or NADH cofactor present can be recycled by the engineered polypeptide using IPA as reductant.

In certain embodiments, the methods comprising the conversion of compound (2) to compound (1) disclosed herein can be carried out without adding NADPH or NADH cofactor during the reaction and without any other enzyme systems present (e.g., glucose dehydrogenase, or formate dehydrogenase).

In certain embodiments, the methods comprising the use of an engineered polypeptide of the present disclosure for the conversion of compound (2) to compound (1) can be carried out wherein no cofactor recycling enzyme is present other than the engineered polypeptide. For example, the methods comprising of the present disclosure can be carried out wherein the reaction conditions comprise an IPA concentration is about 55-75% (v/v), an NADPH or NADH cofactor loading of about 0.03-0.5 g/L, and wherein no cofactor recycling enzyme is present other than the engineered polypeptide.

Suitable secondary alcohols useful in cofactor regenerating systems include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment, the secondary alcohol is isopropanol. Suitable aryl-alkyl carbinols include unsubstituted and substituted 1-arylethanols.

In some embodiments where the cofactor recycling system produces a volatile product, such as acetone from isopropanol, the volatile product can be removed by sparging the reaction solution with a non-reactive gas or by applying a vacuum to lower the reaction pressure and removing the volatile present in the gas phase. A non-reactive gas is any gas that does not react with the reaction components. Various non-reactive gases include nitrogen and noble gases (e.g., inert gases). In some embodiments, the non-reactive gas is nitrogen gas. For example, acetone formed by oxidation of isopropanol can be removed by sparging with nitrogen gas or applying a vacuum to the reaction solution and removing the acetone from the gas phase by an acetone trap, such as a condenser or other cold trap.

In the embodiments herein, the polypeptides carrying out the conversion of compound (2) to compound (1) and any additional enzymes of the optional cofactor regeneration system, may be added to the reaction mixture in the form of the purified enzymes, whole cells transformed with gene(s) encoding the enzymes, and/or cell extracts and/or lysates of such cells. The gene(s) encoding the polypeptides disclosed herein and the optional cofactor regeneration enzymes can be transformed into host cells separately or together into the same host cell. Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

Generally, the order of addition of reactants (e.g., substrate, cofactor, polypeptide) is not critical to the methods of the present disclosure. The reactants may be added together at the same time to a solvent (e.g., monophasic solvent, biphasic aqueous co-solvent system, and the like), or alternatively, some of the reactants may be added separately, and some together at different time points.

In some embodiments any of the above describe methods for the conversion of compound (2) to compound (1) can be carried out wherein the method comprises contacting an analog of compound (2) with an engineered polypeptide of the present disclosure (e.g., as described in Table 2 and elsewhere herein) in the presence of NADPH or NADH cofactor under suitable reaction conditions, thereby resulting in the preparation of the chiral alcohol of the corresponding analog of compound (1) in diastereomeric excess. Suitable reactions conditions for the conversion of analogs of compound (2) to the chiral alcohol of the corresponding analogs of compound (1) can be the same as used for compound (2) or determined by the ordinary artisan based on the known properties of the analog compounds and routine experimentation.

In some embodiments, the analogs of compound (1) prepared using the above described methods include the analogs of compound (1) comprising the compound of Formula Ia shown below.

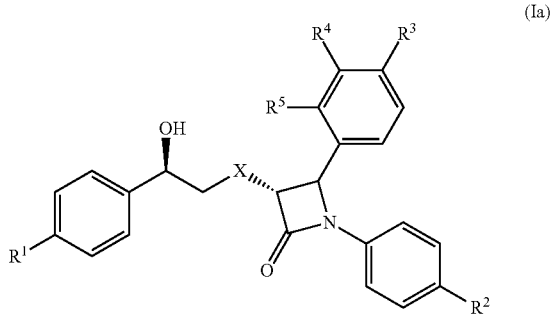

(Ia)

wherein,

X is selected from C or S;

$R^1$ is selected from —H, —F, —Cl, —Br, or —I;

$R^2$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;

$R^3$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;

$R^4$ is selected from —H, —F, —Cl, —Br, —I, —CN, —OH (optionally protected with a hydroxyl protecting group); and $R^5$ is selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle.

Examples of hydroxyl protecting groups and nitrogen protecting groups that may be the R group of compounds of Formula IIa undergoing the biocatalytic methods of the present disclosure can be found in P. G. M. Wuts and T. W. Greene, "Greene's Protective Groups in Organic Synthesis-Fourth Edition," John Wiley and Sons, New York, N.Y., 2007, Chapter 7 ("Greene").

Accordingly, in some embodiments the present disclosure provides a method of preparing a compound of Formula Ia comprising: contacting a compound of Formula IIa

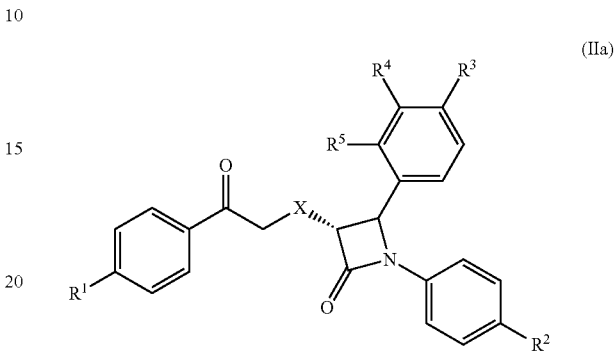

(IIa)

wherein,

X, $R^1$, $R^2$, $R^3$, $R^4$, and $R^5$, are defined as above for Formula Ia, with an engineered polypeptide of the present disclosure (e.g., as described in Table 2 and elsewhere herein) in the presence of NADPH or NADH cofactor under suitable reaction conditions.

In some embodiments, the present disclosure provides a method of preparing a compound of Formula Ia in which $R^2$ and $R^3$ are each independently selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: —(C$_1$-C$_6$)alkyl, —(C$_1$-C$_6$)alkoxy, —(C$_1$-C$_6$)alkenyl, —(C$_1$-C$_6$)alkenoxy, —(C$_1$-C$_6$)alkynyl, —(C$_1$-C$_6$)alkynoxy, —(C$_1$-C$_6$)cycloalkyl, or a heterocycle, having from 1 to 4 carbon atoms and 1 to 2 hetero atoms.

In some embodiments, the present disclosure provides a method of preparing a compound of Formula Ia in which $R^2$ and $R^3$ are each independently selected from —H, —F, —Cl, —Br, —I, —CN, —OH (optionally protected with a hydroxyl protecting group), —CH$_2$NH$_2$ (optionally protected with a nitrogen protecting group), and any one of the following optionally substituted groups: —(C$_1$-C$_4$)alkyl, —(C$_1$-C$_4$)alkoxy, —(C$_1$-C$_4$)alkenyl, —(C$_1$-C$_4$)alkenoxy, —(C$_1$-C$_4$)alkynyl, —(C$_1$-C$_4$)alkynoxy, —(C$_1$-C$_4$)cycloalkyl, or a heterocycle, having from 1 to 3 carbon atoms and 1 to 2 hetero atoms.

In some embodiments, the present disclosure provides a method of preparing a compound of Formula Ia in which X is C, $R^2$ and $R^3$ are each independently selected from —H, —F, —Cl, —Br, —I, —CN, —OH (optionally protected with a hydroxyl protecting group), and —CH$_2$NH$_2$ (optionally protected with a nitrogen protecting group).

In some embodiments, the present disclosure provides a method of preparing a compound of Formula Ia in which X is C, $R^2$ and $R^3$ are each independently selected from the following optionally substituted groups: —(C$_1$-C$_4$)alkyl, —(C$_1$-C$_4$)alkoxy, —(C$_1$-C$_4$)alkenyl, —(C$_1$-C$_4$)alkenoxy, —(C$_1$-C$_4$)alkynyl, and —(C$_1$-C$_4$)alkynoxy. In some embodiments, $R^2$ and $R^3$ are optionally substituted with one or more —OH groups.

In some embodiments, the present disclosure provides a method of preparing a compound of Formula Ia in which X is C, any one or more of $R^2$, $R^3$, or $R^5$ is an —OH or an —OH group protected with a hydroxyl protecting group. In some embodiments of the methods, the hydroxyl protecting group of $R^2$, $R^3$, and/or $R^5$ is selected from selected from the group consisting of benzyl, acetyl, benzoyl, tert-butyloxycarbonyl, silyl, tert-butyldiphenylsilyl, trimethylsilyl, para-methoxybenzyl, benzylidine, dimethylacetal, and methoxy methyl. In some embodiments, the silyl group is —Si—$(R^a)(R^b)(R^c)$ and $R^a$, $R^b$, and $R^c$ are each independently selected from the group consisting of $C_1$-$C_6$ alkyl, phenyl, acetyl, and benzyl groups.

In some embodiments, the present disclosure provides a method of preparing a compound of Formula Ia in which $R^1$ is —F, $R^2$ is —F, $R^4$ is —H, and/or $R^5$ is —H.

In some embodiments, the analogs of compound (1) prepared using the above described methods include the anti-hypercholesterolemic compounds described in PCT publication WO 2008/085300A1 based on compounds of Formula Ib,

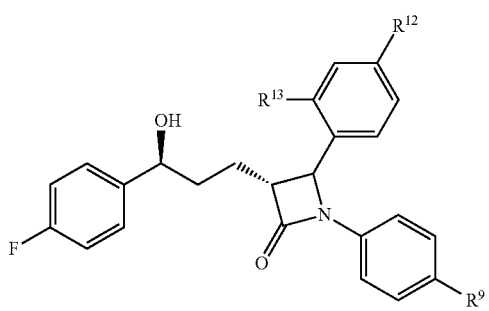

(Ib)

wherein,
$R^9$ is selected from the group consisting of chloro, fluoro, —C≡C—($C_1$-$C_6$)alkyl-$NR^{10}R^{11}$, —$(CH_2)_x$CH═CH—($C_1$-$C_6$)alkyl-$NR^{10}R^{11}$, ($C_1$-$C_8$)alkyl-$NR^{10}R^{11}$, —C≡C—($C_1$-$C_4$)alkyl-CH—$(CH_2$—$NR^{10}R^{11})_2$, —($C_1$-$C_6$)alkyl-CH—$(CH_2$—$NR^{10}R^{11})_2$, —C≡C—($C_1$-$C_6$)alkyl-$R^{11a}$, —$(CH_2)_x$CH═CH—($C_1$-$C_6$)alkyl-$R^{11a}$, —($C_1$-$C_8$)alkyl-$R^{11a}$, —C≡C—($C_1$-$C_6$)alkyl, —$(CH_2)_x$CH═CH—($C_1$-$C_6$) alkyl, —($C_1$-$C_8$)alkyl, —($C_1$-$C_{15}$)alkynyl mono- or poly-substituted with —OH and optionally substituted with $R^{14}$, —($C_1$-$C_{15}$)alkenyl mono- or poly-substituted with —OH and optionally substituted with $R^{14}$, —($C_1$-$C_{15}$)alkyl mono- or poly-substituted with —OH and optionally substituted with $R^{14}$ and x is an integer selected from 0, 1 and 2;

$R^{10}$ is independently selected at each occurrence from the group consisting of —H and —($C_1$-$C_3$)alkyl;

$R^{11}$ is independently selected at each occurrence from the group consisting of —H, —($C_1$-$C_3$)alkyl, —C(O)—($C_1$-$C_3$) alkyl, —C(O)—$NR^{10}R^{10}$, —$SO_2$—($C_1$-$C_3$)alkyl and —$SO_2$-phenyl;

$R^{11a}$ is selected from the group consisting of —C(O)—$NR^{10}R^{10}$, —$SO_2$—($C_1$-$C_3$)alkyl and —$SO_2$-phenyl;

$R^{12}$ is selected from the group consisting of —($C_2$-$C_{15}$) alkynyl mono- or poly-substituted with —OH and optionally substituted with $R^{14}$, —($C_2$-$C_{15}$)alkenyl mono- or poly-substituted with —OH and optionally substituted with $R^{14}$, —($C_2$-$C_{15}$)alkyl mono- or poly-substituted with —OH and optionally substituted with $R^{14}$;

$R^{13}$ is selected from the group consisting of —H and —OH; and $R^{14}$ is a sugar residue optionally substituted with —COOH, —COO—($C_1$-$C_3$)alkyl and —($C_1$-$C_3$)alkyl-OH; provided that when $R^9$ is selected from the group consisting of —C≡C—$(CH_2)_{1-6}$—$NR^{10}R^{11}$, —CH═CH—$(CH_2)_{1-6}$—$NR^{10}R^{11}$ and —$(CH_2)_{1-8}$—$NR^{10}R^{11}$, then $R^{12}$ is not selected from the group consisting of —($C_1$-$C_{15}$)alkyl mono- or poly-substituted with —OH, —CH═CH—($C_1$-$C_3$)alkyl mono- or poly-substituted with —OH, —C≡C—($C_1$-$C_3$)alkyl mono- or poly-substituted with —OH, and —$(CH_2)_{0-1}$—C(═$CH_2$)—$CH_2$OH.

Accordingly, in some embodiments the present disclosure provides a method of preparing a compound of Formula Ib comprising: contacting a compound of Formula IIb,

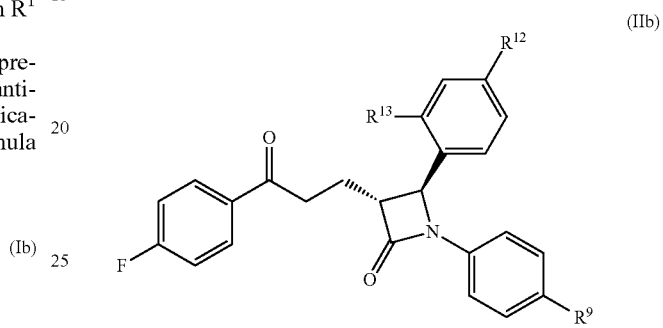

(IIb)

wherein,
$R^9$, $R^{10}$, $R^{11}$, $R^{11a}$, $R^{12}$, $R^{13}$, and $R^{14}$ are defined as above for Formula Ib, with an engineered polypeptide of the present disclosure (e.g., as described in Table 2 and elsewhere herein) in the presence of NADPH or NADH cofactor under suitable reaction conditions.

In some embodiments, the analogs of compound (1) prepared using the above described methods include the anti-hypercholesterolemic compounds described in published Japan patent application 2010-83880, including the compound (1c) and other related analog compounds having substituted pyridines or other heteroaryl at $R^9$ of compound of Formula (Ib):

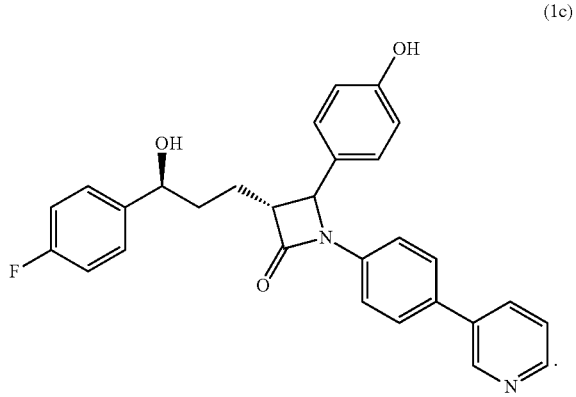 [SMILES: O=C1[C@H](CC[C@H](O)c2ccc(F)cc2)C(c2ccc(O)cc2)N1c1ccc(-c2cccnc2)cc1]

(1c)

In some embodiments, the analogs of compound (1) prepared using the above described methods include the anti-hypercholesterolemic compounds described in PCT publication WO2010/056788, including the compound (1d) and other related analog compounds having substituted alkyl chains at $R^9$ and $R^{12}$ positions of the compound of Formula (Ib):

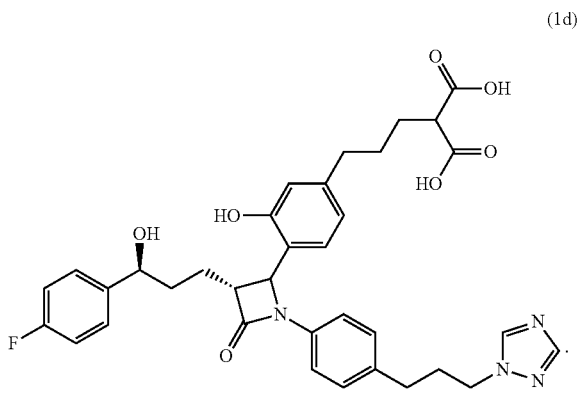 [SMILES: O=C(O)C(CCCc1ccc(C2[C@@H](CC[C@H](O)c3ccc(F)cc3)C(=O)N2c2ccc(CCCn3cncn3)cc2)c(O)c1)C(=O)O]

(1d)

In some embodiments, the analogs of compound (1) prepared using the above described methods include the antihypercholesterolemic compounds described in US published patent application US2010/160282A1 and PCT Publication WO2010/100255.

In some embodiments, the analogs of compound (1) prepared using the above described methods include the antihypercholesterolemic compounds described in US published patent application US2010/152156A1, including the compound of Formula (Ie) and other related analog compounds having a sulfur atom at position X of the compound of Formula (Ia):

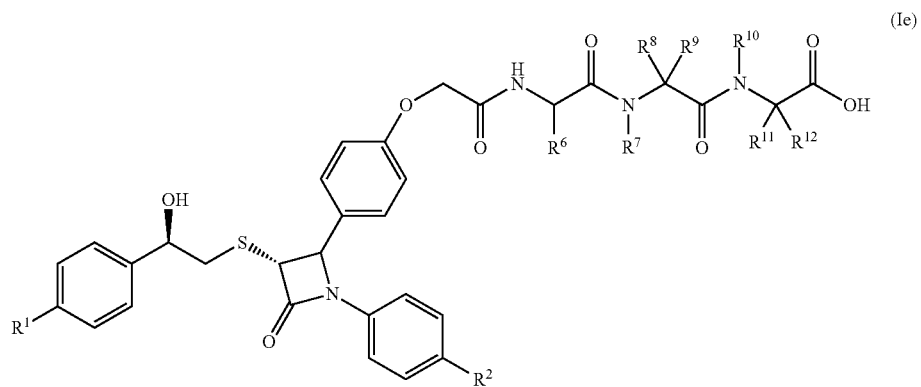

(Ie)

wherein:

$R^1$ is hydrogen, alkyl, halo, $C_{1-6}$ alkoxy or $C_{1-6}$ alkylS—;

$R^2$ is hydrogen, $C_{1-6}$ alkyl, halo or $C_{1-6}$ alkoxy;

$R^6$ is hydrogen, $C_{1-6}$ alkyl, $C_{3-6}$ cycloalkyl or aryl;

$R^8$, $R^9$, $R^{11}$ and $R^{12}$ are independently hydrogen, a branched or unbranched $C_{1-6}$ alkyl, $C_{3-6}$ cycloalkyl or aryl; wherein said $C_{1-6}$ alkyl may be optionally substituted by one or more hydroxy, amino, guanidino, cyano, carbamoyl, carboxy, $C_{1-6}$alkoxy, aryl $C_{1-6}$alkoxy, $(C_{1-4}$alkyl$)_3$Si, N—$(C_{1-6}$ alkyl)amino, N,N—$(C_{1-6}$alkyl)-2-amino, $C_{1-6}$alkylS(O)$_a$, $C_{3-6}$cycloalkyl, aryl or aryl$C_{1-6}$ alkyl-S(O)$_a$, wherein a is 0-2; and wherein any aryl group may be optionally substituted by one or two substituents selected from halo, hydroxy, $C_{1-6}$alkyl, $C_{1-6}$alkoxy, or cyano;

$R^7$ and $R^{10}$ is hydrogen, $C_{1-6}$ alkyl, or aryl$C_{1-6}$ alkyl;

and, wherein $R^8$ and $R^9$ may form a ring with 2-7 carbon atoms and wherein $R^7$ and $R^8$ may form a ring with 3-6 carbon atoms; or a pharmaceutically acceptable salt, solvate, solvate of such a salt or a prodrug thereof.

6. EXAMPLES

Various features and embodiments of the disclosure are illustrated in the following representative examples, which are intended to be illustrative, and not limiting.

Example 1

Wild-Type Ketoreductase Gene Acquisition and Construction of Expression Vectors

The wild-type ketoreductase gene from *L. kefir* (SEQ ID NO: 1) was designed for expression in *E. coli* using standard codon optimization. (Codon-optimization software is reviewed in e.g., "OPTIMIZER: a web server for optimizing the codon usage of DNA sequences," Puigbò et al., Nucleic Acids Res. 2007 July; 35(Web Server issue): W126-31. Epub 2007 Apr. 16.) Genes were synthesized using oligonucleotides composed of 42 nucleotides and cloned into expression vector pCK110900 (vector depicted as FIG. 3 in US Patent Application Publication 20060195947, which is hereby incorporated by reference herein) under the control of a lac promoter. The expression vector also contained the P15a origin of replication and the chloramphenicol resistance gene. Resulting plasmids were transformed into *E. coli* W3110 (fhu-) using standard methods. Polynucleotides encoding the engineered ketoreductase polypeptides were also cloned into vector pCK110900 for expression in *E. coli* W3110.

The engineered ketoreductase polypeptide of SEQ ID NO: 2 which was derived previously based on directed evolution of a codon-optimized gene encoding the wild-type ketoreductase of *Lactobacillus kefir* (Genbank acc. No. AAP94029.1; GI: 33112056). SEQ ID NO: 2 has 19 amino acid residue differences relative to the WT ketoreductase (D3N, G7S, L17Q, V95L, S96Q, G117S, Q127R, E145S, F147L, T152M, L153V, L176V, Y190C, D198K, L199D, E200P, K211R, I223V, and A241S). The polypeptide of SEQ ID NO: 2 was found to be able to convert compound (2) to compound (1) in >99% ee and with greater than 50% conversion rate in 20 h while converting IPA to acetone to recycle the NADP+ cofactor in 20% IPA (i.e., without a secondary enzyme for cofactor recycling) under initial screening conditions (4 g/L compound (2) substrate; 0.5 g/L NADP, 100 mM TEA, pH 7.0, 1 mM MgSO$_4$, 25° C.). The polypeptide SEQ ID NO: 2 was used as the starting backbone for subsequent rounds of evolution. Multiple rounds of directed evolution of the gene encoding SEQ ID NO: 2 (i.e., SEQ ID NO: 1) were carried out. Each round used the gene encoding the most improved engineered polypeptide from each round as the parent "backbone" sequence for the subsequent round of evolution. The resulting engineered ketoreductase polypeptide sequences and specific mutations and relative activities are listed in Table 2.

Example 2

Production of Engineered Ketoreductase Polypeptides

The engineered ketoreductase polypeptides of the disclosure were produced in *E. coli* W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic process disclosed herein.

Fermentation for Shake Flask Powders:

A single microbial colony of *E. coli* containing a plasmid encoding an engineered ketoreductase of interest is inoculated into 50 mL Luria Bertani broth containing 30 μg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM $MgSO_4$) containing 30 μg/ml chloramphenicol, in a 1 liter flask to an optical density at 600 nm (OD600) of 0.2 and allowed to grow at 30° C. Expression of the ketoreductase gene is induced by addition of isopropyl-β-D-thiogalactoside ("IPTG") to a final concentration of 1 mM when the OD600 of the culture is 0.6 to 0.8 and incubation is then continued overnight (at least 16 hours). Cells are harvested by centrifugation (5000 rpm, 15 min, 4° C.) and the supernatant discarded.

Production of Ketoreductase Shake-Flask Powders:

The cell pellet is resuspended with an equal volume of cold (4° C.) 100 mM triethanolamine (chloride) buffer, pH 7.0 (optionally including 2 mM $MgSO_4$), and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude ketoreductase polypeptide. Alternatively, the cell pellet (before or after washing) can be stored at 4° C. or −80° C.

Fermentation for Production Downstream Process (DSP) Powders:

Larger-scale (~100-120 g) fermentation of the engineered ketoreductases for production of DSP powders can be carried out as a short batch followed by a fed batch process according to standard bioprocess methods. Briefly, ketoreductase expression is induced by addition of IPTG to a final concentration of 1 mM. Following fermentation, the cells are harvested and resuspended in 100 mM Triethanolamine-$H_2SO_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3

Activity Assay of Engineered Ketoreductase Polypeptides

High-Throughput Growth & Expression: Picked and Grown Using Standard KRED Protocol for W3110 with Direct Induction:

(1) Master growth=single colonies picked from agar Q-trays by Q-bot and grown overnight in LB media containing 1% glucose and 30 μg/mL CAM, 30° C., 200 rpm, 85% humidity. (2) Subculture=20 μL of overnight growth transferred to a deep well plate containing 380 μL 2×YT growth media containing 30 μg/mL CAM, 1 mM IPTG, 1 mM $MgSO_4$, and incubated for ~18 h at 30° C., 200 rpm, 85% humidity. (3) Cell culture centrifuged at 4000 rpm, 4° C. for 10 min., and used media discarded. Cell pellets resuspended in between 200-400 μL lysis buffer (100 mM TEA buffer, pH7.0, containing 1 mM $MgSO_4$, 400 μg/mL PMBS and 500 μg/mL Lysozyme.

High Throughput Screening Procedure:

60-140 μL of a 5.7-100 g/L solution of the substrate in either a mixture of toluene:IPA:acetone (v/v/v ratio of 5:9:1-15:9:1) or IPA:acetone (v/v ratio of 49:1) was added to each well of a Costar™ deep-well 96-well plate. Subsequently, 40-120 μL of a 0.25-1.25 g/L solution of NADP in 100 mM TEA buffer, pH 7.0 containing 1 mM $MgSO_4$ was also added. Finally, 20 μL of a freshly prepared suspension of lysed cells in lysis buffer (either concentrated or diluted up to 20-fold in 100 mM TEA buffer pH 7.0 containing 1 mM $MgSO_4$) was added to make the total volume in each well 200 μL ([substrate]=4-80 g/L, [NADP]=0.1-0.5 g/L, Solvent=either toluene:IPA:acetone:buffer (relative % volumes of 10:18:2:70 or 30:18:2:50) or IPA:acetone:buffer (relative % volumes of 65:35 or 70:30). The plate was then heat sealed and shaken for 2 or 24 h at RT, 30° C., or 37° C. before 0.8 mL of acetonitrile was added to each well to quench the reaction.

The specific conditions of the High Throughput Screening procedure can be varied in order to identify variant polypeptides having amino acid differences providing different improved properties relative to the selected reference polypeptide. Typically, the stringency of screening conditions are increased through the course of the directed evolution of the variant polypeptides. Conditions that can be varied include substrate concentration, cofactor concentration, solvent conditions, temperature, and total reaction time. Exemplary modifications of the screening conditions are noted in Table 2.

Analytical Method Used for Activity Assay:

The plate containing the reactions quenched with acetonitrile were heat sealed, and shaken for 5 minutes, prior to being centrifuged at 4,000 rpm for 10 min. 200 μL of the supernatant was then transferred to a Costar™ round bottom 96-well plate and heat sealed prior to HPLC analysis. HPLC was performed using a C-18 Symmetry 100×4.6 mm, 5 μm column, with isocratic elution of a 66% MeCN:34% $H_2O$ solvent mixture at a flow of 2.5 mL/min. Both substrate and product were detected by UV absorbance at 254 nm.

Example 4

Biocatalytic Process I for Preparation of Compound (1) (Ezetimibe) from Substrate Compound (2)

This example illustrates a first biocatalytic process using an engineered ketoreductase polypeptide of the disclosure to prepare Ezetimibe (compound (1)) on a 10 g scale. The biocatalytic reaction is carried out in an aqueous co-solvent system of TEA buffer (100 mM, pH 7), 30% toluene, 20% IPA, and a substrate loading is 100 g/L. The engineered ketoreductase (polypeptide of SEQ ID NO: 80 at 3 g/L loading) uses the cofactor NADPH (0.1 g/L loading) as a reducing agent, which is oxidized to $NADP^+$ during the reaction. The engineered ketoreductase also acts as the secondary alcohol dehydrogenase in an in-situ "recycling system" to regenerate the reduced form of the cofactor through the oxidation of the IPA co-solvent to acetone. The product in the biocatalytic reaction is extracted into THF and solvent swap with toluene provides the desired crude product of compound (1), which is then further crystallized from THF/toluene.

Preparation of Compound (2) Substrate:

Compound (2) for use as substrate in the biocatalytic reaction can be prepared by oxidation of samples of the Ezetimibe API (compound (1)) according to the following procedure. An oven dried 2-neck 500 mL RB flask equipped with a thermocouple, a magnetic stir bar, and a nitrogen gas inlet was charged with the white powder of compound (1) (32.06 g, 78.3 mmol) and N-methyl morpholine oxide (NMO) (18.3 g, 156.6 mmol). 300 mL of anhydrous dichloromethane was added, affording a clear yellow solution. Oven dried activated 4 Å molecular sieves (35 g) was added, and the solution was cooled to 8° C. (internal temperature) using an ice/NaCl bath. Tetrapropylammonium perruthenate (TPAP) (2.75 g, 7.83 mmol) was added in one portion to the flask. The internal temperature rose to 15.4° C. then slowly dropped to 8° C. The ice bath was removed, and the reaction mixture was allowed to stir at 25° C. for 2.5 h. The dark brown solution was filtered through a 4" bed of Celite and rinsed with dichloromethane (1.5 L) and diethyl ether (500 mL). The filtrate was monitored by TLC to ensure all ketone product had been eluted. The sample was concentrated under reduced pressure and purified by column chromatography with 25% EtOAc in heptane yielding compound (2) as an off-white solid, 21.01 g (68% Th), 100% pure at $UV_{254}$. HPLC analysis of a compound (2) sample in acetonitrile (~1-5 mg/mL) can be run on an Eclipse XDB-C18 column under the following conditions: T=35° C.; mobile phase A=water+0.1% TFA; mobile phase B=acetonitrile+0.1% TFA; run time=10 min; 0-4.5 min=25% to 90% B; 4.5-5.25 min=90% B; 5.25-6 min=90%-25% B; post-time=1 min at 25% B. UV detection at 214 and 254 nm. Compound (2) retention time=5.85 min.

Biocatalytic Reaction Procedure:

A 250 mL round bottomed flask was equipped with overhead stirrer and internal thermometer. The reactor was charged sequentially with 300 mg DSP powder of engineered ketoreductase polypeptide of SEQ ID NO: 80, 50.0 mL 100 mM TEA buffer (pH 7), 10.0 mg $NADP^+$ dissolved in buffer, 10.0 g of compound (2) dissolved in 30 mL toluene, and 20 mL IPA. The resulting slurry reaction was heated to 30° C. (internal temperature), stirring at ~500 rpm. The final temperature was reached within 15 min. The reaction was run at a starting pH of 7 and the pH remained constant throughout the reaction time. The reaction course was followed periodically by taking samples out of the reaction mixture, quenching, and analyzing as described in HPLC Method 1. At 24 h, the reaction solution was a white suspension and the Method 1 in-process analysis indicated 82% conversion. At 48 h, in-process analysis indicated 94% conversion, and the reaction was cooled to 25° C.

Crude Product Work-Up Procedure:

THF (60 mL) was charged to the reaction mixture at room temperature and agitated at 250 rpm for 15 minutes. Phases were allowed to separate and the aqueous layer removed. The THF phase was collected separately. The purity of the product in the THF phase was determined to 94.6% according to HPLC (Method 1). Toluene (60 mL) was added, and the resulting solution was concentrated to approximately 60 mL on rotary evaporator at 40° C. and incrementally reducing the pressure to 70 Torr. Toluene (60 mL) was added again, and the resulting hazy solution was concentrated to approx 90 mL on rotary evaporator at 40° C. and incrementally reducing the pressure to 70 Torr. At this stage product precipitated as white solid and GC analysis of the organic (THF) layer indicated that ≤2.0% THF remained. The precipitated product was recovered by filtration and the residue was washed with 1×15 mL of toluene and dried under vacuum (approx 20 mm Hg) for 24 hours. This provided: 8.75 g (90% yield) chiral alcohol of compound (1) as a white solid; chemical purity of 97.2% (AUC, HPLC Method 1).

Crystallization Procedure:

To a suspension of 8.0 g crude compound (1) in toluene (80 mL) at 82° C. (internal), THF (10 mL) was added slowly while stirring. The slurry became clear solution at the end of the addition. The solution was allowed to cool to room temperature (25° C.) over a period of 12 hours while stirring magnetically (100 RPM). The resulting white precipitate was filtered under reduced pressure. The white residue was washed once with cold toluene (10 mL) and dried under vacuum (~20 mm Hg) for 24 hours. This provided: 6.3 g (68% yield) of compound (1) in a single crop as a white solid; chemical purity=99.9% (AUC, HPLC Method 1); chiral purity>99.9% d.e. (Method 2).

Analytical Methods Using in the Process of Example 4:

Samples were analyzed for percent conversion and/or diastereomeric purity using HPLC according to Method 1 or Method 2 as described below. HPLC samples were prepared as follows: 10 µL are taken from the reaction suspension via pipette, dissolved in 1 mL of acetonitrile, and injected neat into the HPLC according the Method 1 or Method 2 parameters.

HPLC Method 1 parameters for monitoring biocatalytic reaction progress are shown in Table 4.

TABLE 4

| Method 1 HPLC parameters | |
| --- | --- |
| Instrument | Agilent HPLC 1200 series |
| Column | Symmetry C18 4.6 × 100 mm |
| Mobile Phase | 70% Acetonitrile + 0.1% TFA, |
| | 30% Water + 0.1% TFA isocratic |
| Flow Rate | 1.0 ml/min |
| Detection Wavelength | 280.0 nm |
| Detector Temperature | 45° C. |
| Injection Volume | 10 µl |
| Run time | 4.0 min |
| Retention times | Product [Compound (1)]: 2.03 min |
| | Substrate [Compound (2)]: 2.60 min |
| | Toluene: 3.67 min |
| Response factor (Substrate/Product) | 1.4 |

Method 2 HPLC parameters for determining diastereomeric purity of biocatalytic reaction product are shown in Table 5.

TABLE 5

| Method 2 HPLC parameters | |
| --- | --- |
| Instrument | Agilent HPLC 1200 series |
| Column | Chiralpak AD-H 4.6 × 250 mm (5 um) |
| Mobile Phase | 80% Heptane/20% EtOH (0-18 min, isocratic) |
| | 50% Heptane/50% EtOH (18.5-33 min, isocratic) |

TABLE 5-continued

Method 2 HPLC parameters

| | |
|---|---|
| Flow Rate | 1.0 ml/min |
| Detection Wavelength | 230.0 nm |
| Detector Temperature | 20° C. |
| Injection Volume | 10 μl |
| Run time | 45.0 min |
| Retention times | Substrate [Compound (2)]: 31.56 min |
| | Product [Compound (1)]: 16.44 min |
| | (R, R, S) diastereomer: 15.05 min |

Example 5

Process II for Preparation of Ezetimibe from Compound (2)

This example illustrates a second biocatalytic process using an engineered ketoreductase polypeptide of the disclosure to prepare Ezetimibe (Compound (1)) on a 20 g scale.

Biocatalytic Reaction Procedure:

A 500 mL jacketed reactor was charged sequentially with the following: 20 g compound (2) (assayed at 88% w/w purity) as solid, 130 mL IPA, 55 mL TEA buffer, 2.0 mL of TEA buffer solution containing 20 mg $NADP^+$, 13.0 mL of TEA buffer solution containing 400 mg of the engineered KRED of SEQ ID NO: 168. The resulting reaction mixture was stirred at 30° C. (internal) at ~250 rpm. The pH of the reaction mixture ranges between 6.30-6.40 at 30° C., with an initial buffer pH of 6.75 at RT. The reaction course was followed periodically by taking samples from the reaction mixture, quenching, and analyzing as described in Method 3. Percent conversion at 4 h, 18 h, and 19 h, was 72.0%, 98.2%, and 98.4%, respectively. After in-process analysis (Method 3) indicated maximum possible conversion (at 98.4% conversion) the reaction mixture was taken for the subsequent workup and isolation procedure.

Product Work-Up and Isolation:

Acetone formed during the reaction was distilled under vacuum (40 torr) at 30° C. To the thick slurry, water (200 mL) was added and the distillation continued at a slightly elevated temperature (40 torr, 40° C.) until about 25% IPA remained relative to the start of distillation. The slurry with the crude product was drained from the reactor. The reactor was washed with another 200 mL of water and drained into the same container from above. The crude product was collected by filtration through a sintered funnel and washed with 50 mL water. The wet cake was dried for 15 h under vacuum (5 torr) at 25° C. Upon drying, 16.0 g of crude product was obtained 99.0% chemical purity (AUC, HPLC, 99.8% d.e.). Yield of crude product is 90% with respect to the effective loading of keto phenol substrate (17.6 g). The crude product was further purified by recrystallization as described below.

Recrystallization:

A suspension of crude product (10.0 g) in IPA (30.0 mL) was heated to 60° C. (internal) to allow maximum dissolution of product. The hot solution from above was passed through a celite (5.0 g) bed in a sintered funnel. Upon complete filtration, the celite bed was washed with pre-heated IPA (30.0 mL, ~60° C.). Distillation to dryness of the combined filtrates from above showed >9.0 g of product. The white solid was stirred in 30.0 mL IPA and heated to 60° C. (internal) to obtain a clear solution. Water (40.0 mL) was added drop wise to the above solution at 60° C. and the resultant solution was allowed to cool to 25° C. The crystallized product was filtered through a sintered funnel and dried under vacuum (5 torr, 25° C.) for 15 h. This provided: 8.8 g of chiral alcohol product of compound (1) in a single crop as a white solid; 99.5% chemical purity (AUC, HPLC, 99.9% d.e.). Essentially the only detectable impurity was the keto phenol substrate, measuring 0.38% (AUC, HPLC).

Analytical Methods Used in the Process of Example 5:

An HPLC method for determination of % conversion (Method 3); and a chiral HPLC method for determination of diastereomeric purity (Method 4).

Method 3 Sample Preparation for HPLC:

0.3 mL of reaction mixture was sampled from the stirred reaction suspension via pipette. The appearance of the sample should be as finely dispersed as the reaction mixture itself. The sample was fully dissolved in 25 mL of methanol or acetonitrile. Injection is neat into the HPLC.

The HPLC parameters used for determination of percent conversion according to Method 3 are shown in Table 6.

TABLE 6

| | |
|---|---|
| Instrument | Varian 920-LC series |
| Column | Alltima C18, 53 × 7 mm, 3 μm with guard column (P/N: 50605) |
| Mobile Phase | 60% Acetonitrile, 40% Water (Isocratic) |
| Flow Rate | 1.3 mL/min |
| Detection Wavelength | 254.0 nm |
| Column Temperature | Ambient |
| Injection Volume | 10 μL |
| Run time | 5.0 min |
| Retention times | Product Compound (1): 2.67 min |
| | Keto phenol Substrate Compound (2): 3.92 min |
| Response Factor (Substrate/Product) | 1.46 |

Method 4 HPLC Sample Preparation of In-Process Sample:

10 μL of reaction mixture is sampled from the stirred reaction suspension via micropipette and added to 1 mL of absolute ethanol in an HPLC glass vial ready for analysis.

Method 4 HPLC Sample Preparation of Final Product Sample:

1 mL of absolute ethanol is added directly to 1 mg of sample in an HPLC glass vial. Ensure full dissolution before submitting to HPLC for analysis.

The HPLC parameters used for determination of percent diastereomeric purity of product according to Method 4 are shown in Table 7.

TABLE 7

| | | | |
|---|---|---|---|
| Instrument | Agilent HPLC 1200 series (Normal Phase HPLC) | | |
| Column | Chiralpak AD-H, 250 × 4.6 mm, 5 μm | | |
| Mobile Phase | A: Heptane, B: Ethanol absolute (Gradient) | | |
| | Time (min) | % A | % B | Flow Rate (mL/min) |
| | 0.0 | 80 | 20 | 1.20 |
| | 15.5 | 80 | 20 | 1.20 |
| | 28.0 | 50 | 50 | 1.00 |
| | 31.0 | 50 | 50 | 1.00 |
| | 35.0 | 80 | 20 | 1.20 |
| | 40.0 | 80 | 20 | 1.20 |
| Detection Wavelength | 230.0 nm | | |
| Column Temperature | 35° C. | | |
| Injection Volume | 5 μL | | |
| Run time | 40.0 min | | |
| Retention times | Product [Compound (1)]: 12.75 min (R, R, S) diastereomer: 11.99 min | | |

While various specific embodiments have been illustrated and described, it will be appreciated that various changes can be made without departing from the spirit and scope of the invention(s).

What is claimed is:

1. A method for preparing compound of Formula (Ia) in diastereomeric excess

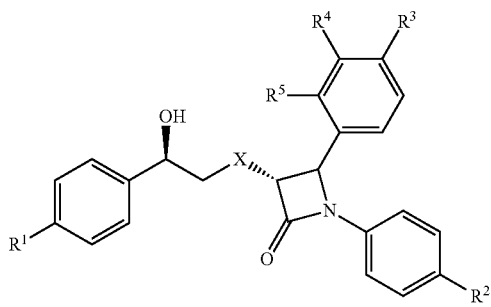

wherein,

X is C or S;

R¹ is selected from —H, —F, —Cl, —Br, or —I;

R² is selected from —H, —F, —Cl, —Br, —I, —CN, —OH (optionally protected with a hydroxyl protecting group), —CH₂NH₂ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;

R³ is selected from —H, —F, —Cl, —Br, —I, —CN, —OH (optionally protected with a hydroxyl protecting group), —CH₂NH₂ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;

R⁴ is selected from —H, —F, —Cl, —Br, —I, —CN, —OH (optionally protected with a hydroxyl protecting group); and R⁵ is selected from —H, —F, —Cl, —Br, —I, —CN, —OH (optionally protected with a hydroxyl protecting group), —CH₂NH₂ (optionally protected with a nitrogen protecting group), and any one of the following optionally substituted groups: alkyl, alkoxy, alkenyl, alkenoxy, alkynyl, alkynoxy, cycloalkyl, aryl, heteroaryl, or heterocycle;

said method comprising:

contacting a compound of Formula (IIa), wherein, X, R¹, R², R³, R⁴, and R⁵ are as defined above,

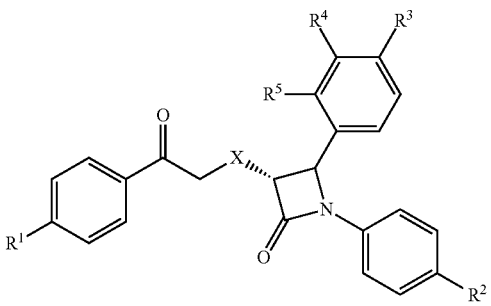

with a non-naturally occurring ketoreductase polypeptide in the presence of cofactor NADPH or NADH under suitable reaction conditions, wherein the polypeptide comprises an amino acid sequence having at least 80% sequence identity to SEQ ID NO:2 and the following amino acid residues: R at position X40; I or L at position X153; A, or P at position X190; A, C, N, S, or T at position X196; F or W at position X199; and I at position X206.

2. The method claim 1 in which R² and R³ are each independently selected from —H, —F, —Cl, —Br, —I, —CN, —OH (optionally protected with a hydroxyl protecting group), —CH₂NH₂ (optionally protected with a nitrogen protecting group), and any one of the following optionally substituted groups: —(C₁-C₆)alkyl, —(C₁-C₆)alkoxy, —(C₁-C₆)alkenyl, —(C₁-C₆)alkenoxy, —(C₁-C₆)alkynyl, —(C₁-C₆)alkynoxy, —(C₁-C₆)cycloalkyl, or a heterocycle, having from 1 to 4 carbon atoms and 1 to 2 hetero atoms.

3. The method claim 1 in which any one or more of R², R³, or R⁵ is an —OH or an —OH group protected with a hydroxyl protecting group.

4. The method of claim 1 in which R¹ is —F, R⁴ is —H, and R⁵ is —H.

5. The method of claim 1, wherein the compound of Formula (Ia) is compound (1)

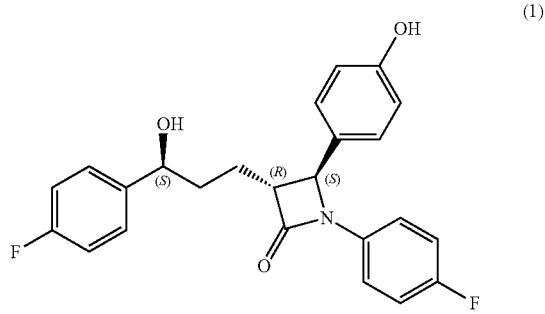

and the compound of Formula (IIa) is compound (2)

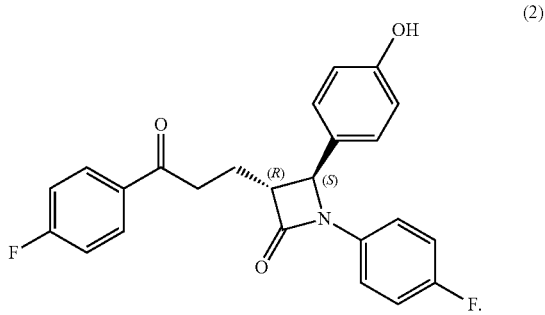

6. The method of claim 5 in which the suitable reaction conditions comprise a compound (2) loading of at least 100 g/L and an engineered polypeptide concentration of about 0.1-3.0 g/L.

7. The method of claim 5 in which the suitable reaction conditions comprise a co-solvent system comprising an aqueous buffer solution and IPA, wherein the IPA concentration is about 55-75% (v/v).

8. The method of claim 5 in which the method further comprises converting NADP⁺ to NADPH with a cofactor recycling system, wherein the cofactor recycling system comprises an NADPH or NADH cofactor loading of about 0.03-0.5 g/L, IPA at a concentration of about 55-75% (v/v), and the non-naturally occurring ketoreductase polypeptide.

9. The method of claim 5 in which the suitable reaction conditions comprise:
   (1) substrate loading of about 50-200 g/L compound (2);
   (2) polypeptide concentration of about 1.5-2.5 g/L;
   (3) NADPH cofactor concentration of about 0.1-0.2 g/L;
   (4) a co-solvent solution of an aqueous buffer and about 60-70% (v/v) IPA;
   (5) about pH 6.6-7.0; and
   (6) temperature of about 28-30° C.

10. The method of claim 5 in which the suitable reaction conditions comprise a substrate loading of about 100 g/L compound (2) and wherein the method results in at least about 91%, 92%, 93%, 94%, 95%, 96%, 97%, 98%, 99% or greater conversion of compound (2) to compound (1) in 24 h.

* * * * *

```
                          SEQUENCE LISTING

<160> NUMBER OF SEQ ID NOS: 168

<210> SEQ ID NO 1
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 1
atgaccaacc gtctgaagag caaagtagcc atcgtaaccg gcgggaccca gggtatcggt      60
ttggcaatcg ccgataaatt tgtagaggag ggtgcgaaaa tagttattac cggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg gcgcaaactg ttgtccgtta atctggatag tgttttttc      360 ggcacccgtc tgggcattcg ccgcatgaag aataaaggct gggcgctag catcatcaat     420 atgagcagta tcagtgggct ggtaggcgat ccgatggtgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc cgctggtcga taaagatcca     600
ggtgctgagg aaatgatgtc acagcgtacg agaacccta tgggccacat tggcgaaccg      660
aatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 2
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 2

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
```

145                 150                 155                 160
Gly Ala Val Arg Ile Met Ser Lys Ser Ala Leu Asp Cys Ala Val
                          165                 170                 175
Lys Asp Tyr Asp Val Arg Val Asn Thr Val His Pro Gly Cys Ile Lys
                          180                 185                 190
Thr Pro Leu Val Asp Lys Asp Pro Gly Ala Glu Glu Met Met Ser Gln
                          195                 200                 205
Arg Thr Arg Thr Pro Met Gly His Ile Gly Glu Pro Asn Asp Val Ala
                          210                 215                 220
Trp Ile Cys Val Tyr Leu Ala Ser Asp Glu Ser Lys Phe Ala Thr Gly
225                       230                 235                 240
Ser Glu Phe Val Val Asp Gly Gly Tyr Thr Ala Gln
                          245                 250

<210> SEQ ID NO 3
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 3
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg cgcaaactg ttgtccgtta atctggatag tgttttttc     360
ggcacccgtc tgggcattcg ccgcatgaag aataaaggct ggggcgctag catcatcaat     420
atgagcagta tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctggtcga taaagatcca     600
ggtgctgagg taatgatgtc acagcgtacg agaacccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 4
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 4

Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
                20                  25                  30
Lys Val Val Ile Thr Gly Arg Arg Ala Asp Val Gly Glu Lys Ala Ala
            35                  40                  45
Lys Ser Ile Gly Gly Thr Asp Val Ile Arg Phe Val Gln His Asp Ala
        50                  55                  60
Ser Asp Glu Ala Gly Trp Thr Lys Leu Phe Asp Thr Thr Glu Glu Ala

```
                65                   70                  75                  80
        Phe Gly Pro Val Thr Val Val Asn Asn Ala Gly Ile Ala Leu Gln
                            85                   90                  95

Lys Ser Val Glu Asp Thr Thr Glu Glu Trp Arg Lys Leu Leu Ser
                           100                  105                 110

Val Asn Leu Asp Ser Val Phe Phe Gly Thr Arg Leu Gly Ile Arg Arg
                           115                  120                 125

Met Lys Asn Lys Gly Leu Gly Ala Ser Ile Ile Asn Met Ser Ser Ile
                   130                  135                 140

Ser Gly Leu Val Gly Asp Pro Met Ile Gly Ala Tyr Asn Ala Ser Lys
        145                  150                  155                 160

Gly Ala Val Arg Ile Met Ser Lys Ser Ala Ala Leu Asp Cys Ala Val
                            165                  170                 175

Lys Asp Tyr Asp Val Arg Val Asn Thr Val His Pro Gly Ala Ile Lys
                            180                  185                 190

Thr Pro Leu Val Asp Lys Asp Pro Gly Ala Glu Val Met Met Ser Gln
                            195                  200                 205

Arg Thr Arg Thr Pro Met Gly His Ile Gly Glu Pro Asn Asp Val Ala
                    210                  215                 220

Trp Ile Cys Val Tyr Leu Ala Ser Asp Glu Ser Lys Phe Ala Thr Gly
        225                  230                  235                 240

Ser Glu Phe Val Val Asp Gly Gly Tyr Thr Ala Gln
                            245                  250

<210> SEQ ID NO 5
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 5
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg gcgcaaactg ttgtccgtta atctggatag tgttttttc      360 ggcacccgtc tgggcattcg ccgcatgaag aataaaggct gggcgctag catcatcaat     420 atgagcagta tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgagg aaatgatgtc tcagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                            759

<210> SEQ ID NO 6
<211> LENGTH: 252
<212> TYPE: PRT
<213> ORGANISM: Artificial Sequence
<220> FEATURE:
<223> OTHER INFORMATION: Variant of L. kefir ketoreductase
```

```
<400> SEQUENCE: 6

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 7
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 7
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg gcgcaaactg ttgtccgtta atctggatag tgttttttc      360 ggcacccgtc tgggcattcg ccgcatgaag aataaaggct gggcgctag catcatcaat     420 atgagcagta tcagtgggct ggtaggcgat ccgatggtgg gggcatacaa tgcttccaag     480
ggggcggtac gtatcatgtc gaaaagcgca gcgctggatt gcagtgaa ggactacgat       540 gtgcgtgtca acacagtaca tccgggctgt atcaagaccc cgctggtcga taaagatcca     600
```

```
ggtgctgagg aaatgatgtc acagcgtacg agaaccccta tgggccacat tggcgaaccg      660
aatgacgtgg catggatctg tgtgtacctg gcatctgacg aatcgaaatt tgcgacgggt      720
agcgaatttg tggtcgacgg cgggtatacc gcacagtga                            759
```

```
<210> SEQ ID NO 8
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 8
```

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 9
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 9
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
```

```
gcagatgtag gtgaaaaggc cgccaaatca atcggcggta ctgatgttat tcgctttgtc      180
cagcacgatg catccgatga agcaggctgg acgaaactgt tcgacaccac cgaggaggca      240
ttcggcccgg ttacgaccgt cgtgaacaat gcagggattg cactgcagaa aagcgttgaa      300
gacactacca cggaggaatg gcgcaaactg ttgtccgtta atctggatag tgttttttc      360 ggcacccgtc tgggcattcg ccgcatgaag aataaaggct gggcgctag catcatcaat      420 atgagcagta tcagtgggct gataggcgat ccgatggtgg gggcatacaa tgcttccaag      480
ggggcggtac gtatcatgtc gaaaagcgca gcgctggatt gcgcagtgaa ggactacgat      540
gtgcgtgtca acacagtaca tccgggctgt atcaagaccc cgctggtcga taaagatcca      600
ggtgctgagg aaatgatgtc acagcgtacg agaaccccta tgggccacat tggcgaaccg      660
aatgacgtgg catggatctg tgtgtacctg gcatctgacg aatcgaaatt tgcgacgggt      720
agcgaatttg tggtcgacgg cgggtatacc gcacagtga                            759
```

<210> SEQ ID NO 10
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 10

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Ile Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 11
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 11

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg gcgcaaactg ttgtccgtta atctggatag tgttttttttc     360 ggcacccgtc tgggcattcg ccgcatgaag aataaaggct gggcgctag catcatcaat     420 atgagcagta tcagtgggct ggtaggcgat ccgatggtgg gggcatacaa tgcttccaag     480 gggcggtac gtatcatgtc gaaaagcgca gcgctggatt gcgcagtgaa ggactacgat     540
gtgcgtgtca acacagtaca tccgggctgt atcaagaccc cgctggccga taaagatcca     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 12
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 12

```
Met Thr Asn Arg Leu Lys Ser Lys Val Ala Ile Val Thr Gly Gly Thr
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175
```

```
Lys Asp Tyr Asp Val Arg Val Asn Thr Val His Pro Gly Cys Ile Lys
            180                 185                 190

Thr Pro Leu Ala Asp Lys Asp Pro Gly Ala Glu Glu Met Met Ser Gln
        195                 200                 205

Arg Thr Arg Thr Pro Met Gly His Ile Gly Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 13
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 13
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggattgc actgcagaa aagcgttgaa      300
gacactacca cggaggaatg cgcaaactg ttgtccgtta atctggatag tgttttttc       360
ggcacccgtc tgggcattcg ccgcatgaag aataaaggct gggcgctag catcatcaat      420
atgagcagta tcagtgggct ggtaggcgat ccgatggtgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc cgctggtcga taaagatcca     600
ggtgctgagg aaatgatgac acagcgtacg agaacccta tgggccacat tggcgaaccg      660
aatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 14
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 14

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95
```

-continued

```
Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Ala Glu Glu Met Met Thr Gln
            195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 15
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 15
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cactggttaa aagcgttgaa   300
gacactacca cggaggaatg cgcaaaactg ttgtccgtta atctggatag tgttttttc    360
ggcacccgtc tgggcattcg ccgcatgaag aataaaggct gggcgctag catcatcaat    420
atgagcagta tcagtgggct ggtaggcgat ccgatggtgg gggcatacaa tgcttccaag   480
ggggcggtac gtatcatgtc gaaaagcgca gcgctggatt gcgcagtgaa ggactacgat   540
gtgcgtgtca acacagtaca tccgggctgt atcaagaccc cgctggtcga taagatcca   600
ggtgctgagg aaatgatgtc acagcgtacg agaaccccta tgggccacat ggcgaaccg   660
aatgacgtgg catggatctg tgtgtacctg gcatctgacg aatcgaaatt tgcgacgggt   720
agcgaatttg tggtcgacgg cgggtatacc gcacagtga                          759
```

```
<210> SEQ ID NO 16
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 16

Met Thr Asn Arg Leu Lys Ser Lys Val Ala Ile Val Thr Gly Gly Thr
1               5                   10                  15
```

```
Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Ala
65                  70                  75                  80

Phe Gly Pro Val Thr Thr Val Asn Asn Ala Gly Ile Ala Leu Val
                85                  90                  95

Lys Ser Val Glu Asp Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 17
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 17
atgaccaacc gtctgaagag caaagtagcc atcgtaaccg cgggaccca gggtatcggt      60
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggattg cactgcagaa aagcgttgaa    300
gacactacca cggaggaatg gcgcaaactg ttgtccgtta atctggatag tgttttttc    360
ggcacccgtc tgggcattcg ccgcatgaag aataaaggct gggcgctag catcatcaat    420
atgagcagta tcagtgggct ggtaggcgat ccgatggtgg gggcatacaa tgcttccaag    480
ggggcggtac gtatcatgtc gaaaagcgca gcgctggatt gcgcagtgaa ggactacgat    540
gtgcgtgtca acacagtaca tccgggctgt atcaagaccc cgctgtctga taaagatcca    600
ggtgctgagg aaatgatgtc acagcgtacg agaaccccta tggccacat tggcgaaccg    660
aatgacgtgg catggatctg tgtgtacctg gcatctgacg aatcgaaatt tgcgacgggt    720
```
agcgaatttg tggtcgacgg cgggtatacc gcacagtga                                759

```
<210> SEQ ID NO 18
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 18
```

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Ser Asp Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

```
<210> SEQ ID NO 19
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 19
```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240

```
ttcggcccgg ttacgaccgt cgtgaacaat gcagggattg cactgcagaa aagcgttgaa    300
gacactacca cggaggaatg gcgcaaactg ttgtccgtta atctggatag tgttttttc     360 ggcacccgtc tgggcattcg ccgcatgaag aataaaggct gggcgctag catcatcaat    420 atgagcagta tcagtgggct ggtaggcgat ccgatggtgg gggcatacaa tgcttccaag    480
ggggcggtac gtatcatgtc gaaaagcgca gcgctggatt gcgcagtgaa ggactacgat    540
gtgcgtgtca acacagtaca tccgggctgt atcaagaccc cgctgtgtga taaagatcca    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                           759
```

<210> SEQ ID NO 20
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 20

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Cys Asp Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 21
<211> LENGTH: 759

<212> TYPE: DNA
<213> ORGANISM: Artificial Sequence
<220> FEATURE:
<223> OTHER INFORMATION: Variant of L. kefir ketoreductase

<400> SEQUENCE: 21

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg gcgcaaactg ttgtccgtta atctggatag tgttttttc      360
ggcacccgtc tgggcattcg ccgcatgaag aataaaggct gggcgctag catcatcaat      420
atgagcagta tcagtgggct ggtaggcgat ccgatggtgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc cgctgaatga taaagatcca     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 22
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 22

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190
```

```
Thr Pro Leu Asn Asp Lys Asp Pro Gly Ala Glu Glu Met Met Ser Gln
            195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 23
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 23

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat cgctttgtc    180
cagcacgatg catccgatga agcaggctgg acgaaactgt tcgacaccac cgaggaggca   240
ttcggcccgg ttacgaccgt cgtgaacaat gcagggattg cactgcagaa aagcgttgaa   300
gacactacca cggaggaatg gcgcaaactg ttgtccgtta atctggatag tgttttttc    360
ggcacccgtc tgggcattcg ccgcatgaag aataaaggct gggcgctag catcatcaat    420
atgagcagta tcagtgggct ggtaggcgat ccgatggtgg gggcatacaa tgcttccaag   480
ggggcggtac gtatcatgtc gaaaagcgca gcgctggatt gcgcagtgaa ggactacgat   540
gtgcgtgtca acacagtaca tccgggctgt atcaagaccc cgctggtcga taaagatcca   600
ggtttggagg aaatgatgtc acagcgtacg agaaccccta tgggccacat tggcgaaccg   660
aatgacgtgg catggatctg tgtgtacctg gcatctgacg aatcgaaatt tgcgacgggt   720
agcgaatttg tggtcgacgg cgggtatacc gcacagtga                         759
```

<210> SEQ ID NO 24
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 24

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110
```

```
Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Leu Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 25
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 25

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgcagaa aagcgttgaa     300
gacactacca cggaggaatg cgcaaactgt tgtccgtta atctggatag tgttttttc      360
ggcacccgtc tgggcattcg ccgcatgaag aataaaggct gggcgctag catcatcaat     420
atgagcagta tcagtgggct ggtaggcgat ccgatggtgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc cgctggtcga taaagatcca     600
ggtaatgagg aaatgatgtc acagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 26
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 26

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30
```

Lys Val Val Ile Thr Gly Arg Arg Ala Asp Val Gly Glu Lys Ala Ala
          35                  40                  45

Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
 65                  70                  75                  80

Phe Gly Pro Val Thr Thr Val Asn Asn Ala Gly Ile Ala Leu Gln
                 85                  90                  95

Lys Ser Val Glu Asp Thr Thr Glu Glu Trp Arg Lys Leu Leu Ser
             100                 105                 110

Val Asn Leu Asp Ser Val Phe Phe Gly Thr Arg Leu Gly Ile Arg Arg
             115                 120                 125

Met Lys Asn Lys Gly Leu Gly Ala Ser Ile Ile Asn Met Ser Ser Ile
         130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                 165                 170                 175

Lys Asp Tyr Asp Val Arg Val Asn Thr Val His Pro Gly Cys Ile Lys
             180                 185                 190

Thr Pro Leu Val Asp Lys Asp Pro Gly Asn Glu Glu Met Met Ser Gln
         195                 200                 205

Arg Thr Arg Thr Pro Met Gly His Ile Gly Glu Pro Asn Asp Val Ala
         210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                 245                 250

<210> SEQ ID NO 27
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 27

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggattg cactgcagaa aagcgttgaa     300
gacactacca cggaggaatg gcgcaaactg ttgtccgtta atctggatag tgttttttc     360 ggcacccgtc tgggcattcg ccgcatgaag aataaaggct gggcgctag catcatcaat     420 atgagcagta tcagtgggct ggtaggcgat ccgatggtgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc cgctggtcga taaagatcca     600
ggtgttgagg aaatgatgtc acagcgtacg agaacccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                             759
```

-continued

<210> SEQ ID NO 28
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 28

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Val Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Pro Gly Val Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 29
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 29

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggccc ctctgcagaa aagcgttgaa      300
gacactacca cggaggaatg gcgcaaactg ttgtccgtta atctggatag tgttttttc      360
```

```
ggcacccgtc tgggcattcg ccgcatgaag aataaaggct tgggcgctag catcatcaat    420
atgagcagta tcagtgggct ggtaggcgat ccgatgatcg gggcatacaa tgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtgctgagg aaatgatctc acagcgtacg agaaccccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                         759
```

<210> SEQ ID NO 30
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 30

```
Met Thr Asn Arg Leu Lys Ser Lys Val Ala Ile Val Thr Gly Gly Thr
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Pro Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 31
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 31

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cactgggcaa aagcgttgaa     300
gacactacca cggaggaatg gcgcaaactg ttgtccgtta atctggatag tgttttttc      360
ggcacccgtc tgggcattcg ccgcatgaag aataaaggct tgggcgctag catcatcaat     420
atgagcagta tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgagg aaatgatctc acagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga               759
```

<210> SEQ ID NO 32
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 32

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gly
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
```

```
                   210                 215                 220
Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 33
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 33
atgaccaacc gtctgaagag caaagtagcc atcgtaaccg gcgggaccca gggtatcggt     60
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggattg cactggctaa agcgttgaa     300 gacactacca cggaggaatg gcgcaaactg ttgtccgtta atctggatag tgttttttc    360 ggcacccgtc tgggcattcg ccgcatgaag aataaaggct tgggcgctag catcatcaat    420
atgagcagta tcagtgggct ggtaggcgat ccgatgatcg ggcatacaa tgcttccaag    480 ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtgctgagg aaatgatctc acagcgtacg agaaacccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                          759

<210> SEQ ID NO 34
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 34

Met Thr Asn Arg Leu Lys Ser Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Ala
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
```

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 35
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 35
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcaggggcca ctctgcagaa aagcgttgaa   300
gacactacca cggaggaatg cgcaaactgt tgtccgtta atctggatag tgttttttc    360 ggcacccgtc tgggcattcg ccgcatgaag aataaaggct gggcgctag catcatcaat   420 atgagctcga tcagtgggct ggtaggcgat ccgatgatcg gggcatacaa tgcttccaag   480
ggggcggtac gtatcatgtc gaaaagcgca gcgctggatt gcgcagtgaa ggactacgat   540
gtgcgtgtca acacagtaca tccgggcgct atcaagaccc cgctgactga taaatttcca   600
ggtgctgggg aaatgatctc acagcgtacg agaaccccta tgggccacat tggcgaaccg   660
aatgacgtgg catggatctg tgtgtacctg gcatctgacg aatcgaaatt tgcgacgggt   720
agcgaatttg tggtcgacgg cgggtatacc gcacagtga                          759

<210> SEQ ID NO 36
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 36

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala

```
                     50                  55                  60
Ser Asp Glu Ala Gly Trp Thr Lys Leu Phe Asp Thr Thr Glu Glu Ala
 65                  70                  75                  80

Phe Gly Pro Val Thr Val Val Asn Asn Ala Gly Ala Thr Leu Gln
                 85                  90                  95

Lys Ser Val Glu Asp Thr Thr Thr Glu Glu Trp Arg Lys Leu Leu Ser
                100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
        130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 37
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 37
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat cgctttgtc   180 cagcacgatg catccgatga agcaggctgg acgaaactgt tcgacaccac cgaggaggca   240
ttcggcccgg ttacgaccgt cgtgaacaat gcagggccga ctctggtgaa aagcgttgaa   300
gacactacca cggaggaatg gcgcaaactg ttgtccgtta atctggatag tgtttttttc   360
ggcacccgtc tgggcattcg ccgcatgaag aataaaggct gggcgctag catcatcaat   420 atgagcagta tcagtgggct ggtaggcgat ccgatgatcg gggcatacaa tgcttccaag   480
ggggcggtac gtatcatgtc gaaaagcgca gcgctggatt gcgcagtgaa ggactacgat   540
gtgcgtgtca acacagtaca tccgggcgct atcaagaccc cgctgaccga taaatttcca   600
ggtgctgagg aaatgatctc acagcgtacg agaacccta tgggccacat tggcgaaccg   660
aatgacgtgg catggatctg tgtgtacctg gcatctgacg aatcgaaatt tgcgacgggt   720
agcgaatttg tggtcgacgg cgggtatacc gcacagtga                          759

<210> SEQ ID NO 38
<211> LENGTH: 252
<212> TYPE: PRT
<213> ORGANISM: Artificial Sequence
```

<220> FEATURE:
<223> OTHER INFORMATION: Variant of L. kefir ketoreductase

<400> SEQUENCE: 38

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Val
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 39
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 39

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg gcgcaaactg ttgtccgtta atctggatag tgttttttc      360 ggcacccgtc tgggcattcg ccgcatgaag aataaaggct gggcgctag catcatcaat      420 atgagcagta tcagtgggct ggtaggcgat ccgatgatcg gggcatacaa tgcttccaag     480
```

```
ggggcggtac gtatcatgtc gaaaagcgca gcgctggatt gcgcagtgaa ggactacgat      540
gtgcgtgtca acacagtaca tccgggcgct atcaagaccc cgatgactga taaatttcca      600
ggtgctgagg aaatgatctc acagcgtacg agaaccccta tgggccacat tggcgaaccg      660
aatgacgtgg catggatctg tgtgtacctg gcatctgacg aatcgaaatt tgcgacgggt      720
agcgaatttg tggtcgacgg cgggtatacc gcacagtga                              759
```

<210> SEQ ID NO 40
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 40

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Met Thr Asp Lys Phe Pro Gly Ala Glu Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 41
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 41

```
atgaccaacc gtctgaagag caaagtagcc atcgtaaccg gcgggaccca gggtatcggt      60
```

```
ttggcaatcg ccgataaatt tgtagaggag ggtgcgaaag tagttatcac cggtcgccgt      120
gcagatgtag gtgaaaaggc cgccaaatca atcggcggta ctgatgttat tcgctttgtc      180
cagcacgatg catccgatga agcaggctgg acgaaactgt tcgacaccac cgaggaggca      240
ttcggcccgg ttacgaccgt cgtgaacaat gcagggccca ctctgcagaa aagcgttgaa      300
gacactacca cggaggaatg gcgcaaactg ttgtccgtta atctggatag tgttttttc      360 ggcacccgtc tgggcattcg ccgcatgaag aataaaggct gggcgctag catcatcaat      420 atgagcagta tcagtgggct ggtaggcgat ccgatgatcg gggcatacaa tgcttccaag      480
ggggcggtac gtatcatgtc gaaaagcgca gcgctggatt gcgcagtgaa ggactacgat      540
gtgcgtgtca acacagtaca tccgggcgct atcaagaccc cgctgactga taaatttcca      600
ggtgctgagg aaatgatctg tcagcgtacg agaaccccta tgggccacat tggcgaaccg      660
aatgacgtgg catggatctg tgtgtacctg gcatctgacg aatcgaaatt tgcgacgggt      720
agcgaatttg tggtcgacgg cgggtatacc gcacagtga                              759
```

<210> SEQ ID NO 42
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 42

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ala Thr Leu Gln
                85                  90                  95

Lys Ser Val Glu Asp Thr Thr Glu Glu Trp Arg Lys Leu Leu Ser
                100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Cys Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240
```

-continued

Ser Glu Phe Val Val Asp Gly Gly Tyr Thr Ala Gln
            245                 250

<210> SEQ ID NO 43
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 43

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg gcgcaaactg ttgtccgtta atctggatag tgttttttc     360
ggcacccgtc tgggcattcg ccgcatgaag aataaaggct gggcgctag catcatcaat     420
atgagcagta tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgagg aaatgatcat tcagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 44
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 44

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Ile Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 45
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 45
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg cgcaaactg ttgtccgtta atctggatag tgtttttttc     360
ggcacccgtc tgggcattcg ccgcatgaag aataaaggct gggcgctag catcatcaat     420 atgagcagta tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgagg aaatgatcaa tcagcgtacg agaacccca tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 46
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 46

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Glu Glu Met Ile Asn Gln
            195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 47
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 47
atgaccaacc gtctgaagag caaagtagcc atcgtaaccg gcgggaccca gggtatcggt      60
cgcgcaatcg cccgtaaatt tgtagaggag ggtgcgaaag tagttatcac cggtcgccgt     120
gcagatgtag gtgaaaaggc cgccaaatca atcggcggta ctgatgttat ccgctttgtc     180
cagcacgatg catccgatga agcaggctgg acgaaactgt tcgacaccac cgaggaggca     240
ttcggcccgg ttacgaccgt cgtgaacaat gcggggccca ctctgcagaa aagcgttgaa     300
gacactacca cggaggaatg gcgcaaactg ttgtccgtta atctggatgg gttttttttc     360
ggcacccgtc tgggcattaa acgcatgaag aataaaggct gggcgctag catcatcaat     420 atgagctcga tcagtgggat ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aaatgatctc acagcgtacg agaaccccta tgggccacat tggcgaaccg     660
gacgacgtgg catggatctg tgtgtacctg gcatctgacg aatcgaaatt tgcgacgggt     720
agcgaatttg tggtcgacgg cgggtatacc gcacagtga                           759

<210> SEQ ID NO 48
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 48

```
Met Thr Asn Arg Leu Lys Ser Lys Val Ala Ile Val Thr Gly Gly Thr
1               5                   10                  15

Gln Gly Ile Gly Arg Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 49
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 49

```
atgaccaacc gtctgaagag caaagtagcc atcgtaaccg gcgggaccca gggtatcggt        60
tttgcaatcg cccgtaaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcaggggcca ctctgcagaa aagcgttgaa       300
gacactacca cggaggaatg gcgcaaactg ttgtccgtta atctggatgg ggttttttc       360 ggcacccgtc tgggcattcg ccgcatgaag aataaaggct gggcgctag catcatcaat       420 atgagctcga tcagtgggat ggtaggcgat ccgatgatcg gggcatacaa tgcttccaag       480
ggggcggtac gtatcatgtc gaaagcgca gcgctggatt gcgcagtgaa ggactacgat        540
gtgcgtgtca acacagtaca tccgggcgct atcaagaccc cgctgactga taaatttcca       600
```

```
ggtgctgggg aaatgatctc acagcgtacg agaacccta tgggccacat tggcgaaccg    660
gacgacgtgg catggatctg tgtgtacctg gcatctgacg aatcgaaatt tgcgacgggt    720
agcgaatttg tggtcgacgg cgggtatacc gcacagtga                          759
```

```
<210> SEQ ID NO 50
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 50

Met Thr Asn Arg Leu Lys Ser Lys Val Ala Ile Val Thr Gly Gly Thr
1               5                   10                  15

Gln Gly Ile Gly Phe Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 51
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 51
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
```

```
cagcacgatg catccgatga agcaggctgg acgaaactgt tcgacaccac cgaggaggca    240
ttcggcccgg ttacgaccgt cgtgaacaat gcagggcct ctctgaacaa aagcgttgaa     300
gacactacca cggaggaatg gcgcaaactg ttgtccgtta atctggatag tgttttttc     360 ggcacccgtc tgggcattcg ccgcatgaag aataaaggct gggcgctag catcatcaat     420 atgagctcga tcagtgggct ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtggtgggg aaatgatctc acagcgtacg agaacccct tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                          759

<210> SEQ ID NO 52
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 52

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Asn
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 53
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 53

| | | | | | |
|---|---|---|---|---|---|
| atgaccaacc | gtctgaagag | caaagtagcc | atcgtaaccg | gcgggaccca | gggtatcggt | 60 |
| ttggcaatcg | ccactaaatt | tgtagaggag | ggtgcgaaag | tagttatcac | cggtcgccgt | 120 |
| gcagatgtag | gtgaaaaggc | cgccaaatca | atcggcggta | ctgatgttat | tcgctttgtc | 180 |
| cagcacgatg | catccgatga | agcaggctgg | acgaaactgt | tcgacaccac | cgaggaggca | 240 |
| ttcggcccgg | ttacgaccgt | cgtgaacaat | gcaggggcca | ctctgcagaa | aagcgttgaa | 300 |
| gacactacca | cggaggaatg | gcacaaactg | ttgtccgtta | atctggatag | tgttttttc | 360 |
| ggcacccgtc | tgggcattcg | ccgcatgaag | aataaaggct | tgggcgctag | catcatcaat | 420 |
| atgagctcga | tcagtgggct | ggtaggcgat | ccgatgatcg | ggcatacaa | tgcttccaag | 480 |
| ggggcggtac | gtatcatgtc | gaaaagcgca | gcgctggatt | gcgcagtgaa | ggactacgat | 540 |
| gtgcgtgtca | acacagtaca | tccgggcgct | atcaagaccc | cgctgactga | taaatttcca | 600 |
| ggtgctgggg | aaatgatctc | acagcgtacg | agaaccccta | tgggccacat | tggcgaaccg | 660 |
| aatgacgtgg | catggatctg | tgtgtacctg | gcatctgacg | aatcgaaatt | tgcgacgggt | 720 |
| agcgaatttg | tggtcgacgg | cgggtatacc | gcacagtga | | | 759 |

<210> SEQ ID NO 54
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 54

Met Thr Asn Arg Leu Lys Ser Lys Val Ala Ile Val Thr Gly Gly Thr
1               5                   10                  15

Gln Gly Ile Gly Leu Ala Ile Ala Thr Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

```
Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 55
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 55
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggccac tctgcagaa aagcgttgaa      300 gacactacca cggaggaatg cgcaaactg ttgtccgtta atctggatag tgttttttc       360 ggcacccgtc tgggcattcg ccgcatgaag aataaaggct gggcgctag catcatcaat     420 atgagctcga tcagtgggct ggtaggccat ccgatgatcg gggcatacaa tgcttccaag    480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aaatgatctc acagcgtacg agaaccccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                           759

<210> SEQ ID NO 56
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 56

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95
```

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
            130                 135                 140

Ser Gly Leu Val Gly His Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
            195                 200                 205

Arg Thr Arg Thr Pro Met Gly His Ile Gly Glu Pro Asn Asp Val Ala
            210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 57
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 57
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag gtgaaaaggc cgccaaatca atcggcggta ctgatgttat cgctttgtc        180
cagcacgatg catccgatga agcaggctgg acgaaactgt tcgacaccac cgaggaggca       240
ttcggcccgg ttacgaccgt cgtgaacaat gcagggccca ctctgcagaa aagcgttgaa       300
gacactacca cggaggaatg cgcaaactg ttgtccgtta atctggatag tgtttttttc        360
ggcacccgtc tgggcattcg ccgcatgaag aataaaggct gggcgctag catcatcaat       420
atgagctcga tcagtgggct ggtaggcgat ccgatgatcg gggcatacaa tgcttccaag       480
ggggcggtac gtatcatgtc gaaaagcgca gcgctggatt gcgcagtgaa ggactacgat       540
gtgcgtgtca acacagtaca tccgggcccg atcaagaccc cgctgactga taaatttcca       600
ggtgctgggg aaatgatctc acagcgtacg agaaccccta tggccacat ggcgaaccg        660
aatgacgtgg catggatctg tgtgtacctg gcatctgacg aatcgaaatt tgcgacgggt       720
agcgaatttg tggtcgacgg cgggtatacc gcacagtga                             759

<210> SEQ ID NO 58
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 58

Met Thr Asn Arg Leu Lys Ser Lys Val Ala Ile Val Thr Gly Gly Thr
1               5                   10                  15

```
Gln Gly Ile Gly Leu Ala Ile Ala Asp Lys Phe Val Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ala Thr Leu Gln
                85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Ile Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Pro Ile Lys
            180                 185                 190
Thr Pro Leu Thr Asp Lys Phe Pro Gly Ala Gly Glu Met Ile Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250

<210> SEQ ID NO 59
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 59
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg gcgcaaactg ttgtccgtta atctggatag tgttttttc     360 ggcacccgtc tgggcattcg ccgcatgaag aataaaggct ggggcgctag catcatcaat     420
atgagctcga tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aaatgatctc acagcgtacg agaaccccta tgggccacat tggcgaaccg     660
aatgacgtgg catggatctg tgtgtacctg gcatctgacg aatcgaaatt tgcgacgggt     720
```
agcgaatttg tggtcgacgg cgggtatacc gcacagtga        759

<210> SEQ ID NO 60
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 60

```
Met Thr Asn Arg Leu Lys Ser Lys Val Ala Ile Val Thr Gly Gly
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Ala Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 61
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 61
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcaggggcca ctctgcagaa aagcgttgaa       300

```
gacactacca cggaggaatg gcgcaaactg ttgtccgtta atctggatag tgttttttc      360 ggcacccgtc tgggcattcg ccgcatgaag aataaaggct tgggcgctag catcatcaat    420
atgagctcga tcagtgggct ggtaggcgat ccgatgatcg gggcatacaa tgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtgctggtg taatgatctc acagcgtacg agaaccccta tgggccacat ggcgaaccg     660 aatgacgtgg catggatctg tgtgtacctg gcatctgacg aatcgaaatt tgcgacgggt    720
agcgaatttg tggtcgacgg cgggtatacc gcacagtga                          759
```

<210> SEQ ID NO 62
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 62

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Val Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 63
<211> LENGTH: 759
<212> TYPE: DNA

<213> ORGANISM: Artificial Sequence
<220> FEATURE:
<223> OTHER INFORMATION: Variant of L. kefir ketoreductase

<400> SEQUENCE: 63

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcca ctctgcagaa aagcgttgaa     300
gacactacca cggaggaatg gcgcaaactg ttgtccgtta atctggatag tgttttttc     360
ggcacccgtc tgggcattcg ccgcatgaag aataaaggct gggcgctag catcatcaat     420
atgagctcga tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aagtgatctc acagcgtacg agaacccta tgggccacat tggcgaaccg      660
aatgacgtgg catggatctg tgtgtacctg gcatctgacg aatcgaaatt tgcgacgggt      720
agcgaatttg tggtcgacgg cgggtatacc gcacagtga                            759
```

<210> SEQ ID NO 64
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 64

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Val Ile Ser Gln
```

```
                    195                 200                 205
Arg Thr Arg Thr Pro Met Gly His Ile Gly Glu Pro Asn Asp Val Ala
            210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 65
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 65

```
atgaccaacc gtctgaagag caaagtagcc atcgtaaccg gcgggaccca gggtatcggt     60
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggggcca ctctgcagaa aagcgttgaa    300
gacactacca cggaggaatg gcgcaaactg ttgtccgtta atctggatag tgttttttc    360
ggcacccgtc tgggcattcg ccgcatgaag aataaaggct gggcgctag catcatcaat    420
atgagctcga tcagtgggct ggtaggcgat ccgaatatcg gggcatacaa tgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtgctgggg aaatgatctc acagcgtacg agaaccccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                           759
```

<210> SEQ ID NO 66
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 66

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
```

```
              115                 120                 125
Met Lys Asn Lys Gly Leu Gly Ala Ser Ile Ile Asn Met Ser Ser Ile
        130                 135                 140

Ser Gly Leu Val Gly Asp Pro Asn Ile Gly Ala Tyr Asn Ala Ser Lys
145                 150                 155                 160

Gly Ala Val Arg Ile Met Ser Lys Ser Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 67
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 67

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggccca ctctgcagaa aagcgttgaa     300
gacactacca cggaggaatg gcgcaaactg ttgtccgtta atctggatag tgttttttc     360
ggcacccgtc tgggcattcg ccgcatgaag aataaaggct gggcgctag catcatcaat     420
atgagctcga tcagtgggct ggtaggcgat ccgtttatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aaatgatctc acagcgtacg agaaccccta tggccacat ggcgaaccg      660
aatgacgtgg catggatctg tgtgtacctg gcatctgacg aatcgaaatt tgcgacgggt     720
agcgaatttg tggtcgacgg cgggtatacc gcacagtga                          759
```

<210> SEQ ID NO 68
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 68

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
```

```
                35                  40                  45
Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ala Thr Leu Gln
                 85                  90                  95

Lys Ser Val Glu Asp Thr Thr Glu Glu Trp Arg Lys Leu Leu Ser
                100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
        130                 135                 140

Ser Gly Leu Val Gly Asp Pro Phe Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 69
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 69
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcaggggcca ctctggcaaa aagcgttgaa       300
gacactacca cggaggaatg gcgcaaactg ttgtccgtta atctggatag tgttttttc        360
ggcacccgtc tgggcattcg ccgcatgaag aataaaggct gggcgctag catcatcaat        420
atgagctcga tcagtgggct ggtaggcgat ccgatgatcg gggcatacaa tgcttccaag       480
ggggcggtac gtatcatgtc gaaaagcgca gcgctggatt gcgcagtgaa ggactacgat       540
gtgcgtgtca acacagtaca tccgggcgct atcaagaccc cgctgactga taaatttcca       600
ggtgctgggg aaatgatcac ccagcgtacg agaaccccta tgggccacat tggcgaaccg       660
aatgacgtgg catggatctg tgtgtacctg gcatctgacg aatcgaaatt tgcgacgggt       720
agcgaatttg tggtcgacgg cgggtatacc gcacagtga                             759

<210> SEQ ID NO 70
```

<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 70

```
Met Thr Asn Arg Leu Lys Ser Lys Val Ala Ile Val Thr Gly Gly
  1               5                  10                  15
Gln Gly Ile Gly Leu Ala Ile Ala Asp Lys Phe Val Glu Glu Gly Ala
                 20                  25                  30
Lys Val Val Ile Thr Gly Arg Arg Ala Asp Val Gly Glu Lys Ala Ala
             35                  40                  45
Lys Ser Ile Gly Gly Thr Asp Val Ile Arg Phe Val Gln His Asp Ala
 50                  55                  60
Ser Asp Glu Ala Gly Trp Thr Lys Leu Phe Asp Thr Thr Glu Glu Ala
 65                  70                  75                  80
Phe Gly Pro Val Thr Thr Val Val Asn Asn Ala Gly Ala Thr Leu Ala
                 85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Ile Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Gly Ala Gly Glu Met Ile Thr Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 71
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 71

```
atgaccaacc gtctgaagag caaagtagcc atcgtaaccg gcgggaccca gggtatcggt    60
ttggcaatcg ccaacaaatt tgtagaggag ggtgcgaaag tagttatcac cggtcgccgt   120
gcagatgtag gtgaaaaggc cgccaaatca atcggcggta cggatgttat tcgctttgtc   180
cagcacgatg catccgatga agcaggctgg acgaaactgt tcgacaccac cgaggaggca   240
ttcggcccgg ttacgaccgt cgtgaacaat gcaggggcca ctctgcagaa aagcgttgaa   300
gacactacca cggaggaatg cgcaaaactg ttgtccgtta atctggatag tgttttttc   360 ggcacccgtc tgggcattcg ccgcatgaag aataaaggct gggcgctag catcatcaat   420
```

```
atgagctcga tcagtgggct ggtaggcgat ccgatgatcg gggcatacaa tgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtgctgggg aaatgatctc acagcgtacg agaaccccta tgggccacat tggcgaaccg    660
aatgacgtgg catggatctg tgtgtacctg gcatctgacg aatcgaaatt tgcgacgggt    720
agcgaatttg tggtcgacgg cgggtatacc gcacagtga                          759
```

```
<210> SEQ ID NO 72
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 72
```

Met Thr Asn Arg Leu Lys Ser Lys Val Ala Ile Val Thr Gly Gly Thr
1               5                   10                  15

Gln Gly Ile Gly Leu Ala Ile Ala Asn Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Ala Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

```
<210> SEQ ID NO 73
<211> LENGTH: 759
<212> TYPE: DNA
<213> ORGANISM: Artificial Sequence
<220> FEATURE:
<223> OTHER INFORMATION: Variant of L. kefir ketoreductase
```

<400> SEQUENCE: 73

```
atgaccaacc gtctgaagag caaagtagcc atcgtaaccg gcgggaccca gggtatcggt      60
ttggcaatcg ccacaaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggggcca ctctgcagaa aagcgttgaa     300
gacactacca cggaggaatg gcgcaaactg ttgtccgtta atctggatag tgttttttttc    360
ggcacccgtc tgggcattcg ccgcatgaag aataaaggct gggcgctag catcatcaat     420
atgagctcga tcagtgggct ggtaggcgat ccgatgatcg gggcatacaa tgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtgctgggg aaatgatctc acagcgtacg agaacccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                             759
```

<210> SEQ ID NO 74
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 74

```
Met Thr Asn Arg Leu Lys Ser Lys Val Ala Ile Val Thr Gly Gly Thr
1               5                   10                  15
Gln Gly Ile Gly Leu Ala Ile Ala Thr Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ala Thr Leu Gln
                85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Ile Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Gly Ala Gly Glu Met Ile Ser Gln
        195                 200                 205
Arg Thr Arg Thr Pro Met Gly His Ile Gly Glu Pro Asn Asp Val Ala
    210                 215                 220
```

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 75
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 75

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggccac tctgcagaa aagcgttgaa      300
gacactacca cggaggaatg gcgcaaactg ttgtccgtta atctggatag tgttttttc      360
ggcacccgtc tgggcattcg ccgcatgaag aataaaggct ggggcgctag catcatcaat     420
atgagctcga tcagtgggct ggtaggcgat ccgatgatcg gggcatacaa tgcttccaag     480
gggcggtac gtatcatgtc gaaaagcgca gcgctggatt gcgcagtgaa ggactacgat      540
gtgcgtgtca acacagtaca tccgggcgct atcaagaccc cgatgactga taaatttcca     600
ggtgctgggg aaatgatctg ccagcgtacg agaaccccta tgggccacat tggcgaaccg     660
aatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 76
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 76

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Thr Leu Gln
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

```
Ser Gly Leu Val Gly Asp Pro Met Ile Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Met Thr Asp Lys Phe Pro Gly Ala Gly Glu Met Ile Cys Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 77
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 77

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggcct ctctgagcaa agcgttgaa    300
gacactacca cggaggaatg gcgcaaactg ttgtccgtta atctggatag tgttttttc    360
ggcacccgtc tgggcattcg ccgcatgaag aataaaggct gggcgctag catcatcaat   420
atgagctcga tcagtgggct ggtaggcgat ccgatgttgg gggcatacaa cgcttccaag   480
ggggcggtac gtatcatgtc gaaaagcgca gcgctggatt gcgcagtgaa ggactacgat   540
gtgcgtgtca acacagtaca tccgggcgct atcaagaccc cgctgactga taaatttcca   600
ggtggtgggg aaatgatctc acagcgtacg cgcaccccta tggcgccaca tggtgaaccg   660
aatgacgtgg catggatctg tgtgtacctg gcatctgacg aatcgaaatt tgcgacgggt   720
agcgaatttg tggtcgacgg cgggtatacc gcacagtga                         759
```

<210> SEQ ID NO 78
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 78

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60
```

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Ser
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 79
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 79

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gcgcaaactg ttgtccgtta atctggatag tgttttttc      360
ggcacccgtc tgggcattcg ccgcatgaag aataaaggct ggggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 80
<211> LENGTH: 252
<212> TYPE: PRT
<213> ORGANISM: Artificial Sequence
<220> FEATURE:

<223> OTHER INFORMATION: Variant of L. kefir ketoreductase

<400> SEQUENCE: 80

| | | | | | | | | | | | | | | | |
|---|---|---|---|---|---|---|---|---|---|---|---|---|---|---|---|
| Met | Thr | Asn | Arg | Leu | Lys | Ser | Lys | Val | Ala | Ile | Val | Thr | Gly | Gly | Thr |
| 1 | | | | 5 | | | | | 10 | | | | | 15 | |
| Gln | Gly | Ile | Gly | Leu | Ala | Ile | Ala | Asp | Lys | Phe | Val | Glu | Glu | Gly | Ala |
| | | | 20 | | | | | 25 | | | | | 30 | | |
| Lys | Val | Val | Ile | Thr | Gly | Arg | Arg | Ala | Asp | Val | Gly | Glu | Lys | Ala | Ala |
| | | 35 | | | | | 40 | | | | | 45 | | | |
| Lys | Ser | Ile | Gly | Gly | Thr | Asp | Val | Ile | Arg | Phe | Val | Gln | His | Asp | Ala |
| | 50 | | | | | 55 | | | | | 60 | | | | |
| Ser | Asp | Glu | Ala | Gly | Trp | Thr | Lys | Leu | Phe | Asp | Thr | Thr | Glu | Glu | Ala |
| 65 | | | | | 70 | | | | | 75 | | | | | 80 |
| Phe | Gly | Pro | Val | Thr | Thr | Val | Val | Asn | Asn | Ala | Gly | Ala | Ser | Leu | Pro |
| | | | | 85 | | | | | 90 | | | | | 95 | |
| Lys | Ser | Val | Glu | Asp | Thr | Thr | Glu | Glu | Trp | Arg | Lys | Leu | Leu | Ser | |
| | | | | 100 | | | | | 105 | | | | | 110 | |
| Val | Asn | Leu | Asp | Ser | Val | Phe | Phe | Gly | Thr | Arg | Leu | Gly | Ile | Arg | Arg |
| | | | 115 | | | | | 120 | | | | | 125 | | |
| Met | Lys | Asn | Lys | Gly | Leu | Gly | Ala | Ser | Ile | Ile | Asn | Met | Ser | Ser | Ile |
| | 130 | | | | | 135 | | | | | 140 | | | | |
| Ser | Gly | Leu | Val | Gly | Asp | Pro | Met | Leu | Gly | Ala | Tyr | Asn | Ala | Ser | Lys |
| 145 | | | | | 150 | | | | | 155 | | | | | 160 |
| Gly | Ala | Val | Arg | Ile | Met | Ser | Lys | Ser | Ala | Ala | Leu | Asp | Cys | Ala | Val |
| | | | | 165 | | | | | 170 | | | | | 175 | |
| Lys | Asp | Tyr | Asp | Val | Arg | Val | Asn | Thr | Val | His | Pro | Gly | Ala | Ile | Lys |
| | | | 180 | | | | | 185 | | | | | 190 | | |
| Thr | Pro | Leu | Thr | Asp | Lys | Phe | Pro | Gly | Gly | Gly | Glu | Met | Ile | Ser | Gln |
| | | | 195 | | | | | 200 | | | | | 205 | | |
| Arg | Thr | Arg | Thr | Pro | Met | Gly | His | Ile | Gly | Glu | Pro | Asn | Asp | Val | Ala |
| | 210 | | | | | 215 | | | | | 220 | | | | |
| Trp | Ile | Cys | Val | Tyr | Leu | Ala | Ser | Asp | Glu | Ser | Lys | Phe | Ala | Thr | Gly |
| 225 | | | | | 230 | | | | | 235 | | | | | 240 |
| Ser | Glu | Phe | Val | Val | Asp | Gly | Gly | Tyr | Thr | Ala | Gln | | | | |
| | | | | 245 | | | | | 250 | | | | | | |

<210> SEQ ID NO 81
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 81

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggcct ctctggcgaa agcgttgaa       300
gacactacca cggaggaatg gcgcaaactg ttgtccgtta atctggatag tgttttttc      360
ggcacccgtc tgggcattcg ccgcatgaag aataaaggct gggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
```

```
gtgcgtgtca acacagtaca tccgggcgct atcaagaccc cgctgactga taaatttcca    600
ggtggtgggg aaatgatctc acagcgtacg agaacccta tgggccacat tggtgaaccg     660
aatgacgtgg catggatctg tgtgtacctg gcatctgacg aatcgaaatt tgcgacgggt   720
agcgaatttg tggtcgacgg cgggtatacc gcacagtga                           759
```

```
<210> SEQ ID NO 82
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 82
```

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Ala
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

```
<210> SEQ ID NO 83
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 83
atgaccaacc gtctgaagag caaagtagcc atcgtaaccg gcgggaccca gggtatcggt    60
```

```
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggcct ctctgacgaa aagcgttgaa     300
gacactacca cggaggaatg gcgcaaactg ttgtccgtta atctggatag tgttttttc    360 ggcacccgtc tgggcattcg ccgcatgaag aataaaggct tgggcgctag catcatcaat    420
atgagctcga tcagtgggct ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtggtgggg aaatgatctc acagcgtacg agaaccccta tgggccacat tggtgaaccg    660
aatgacgtgg catggatctg tgtgtacctg gcatctgacg aatcgaaatt tgcgacgggt    720
agcgaatttg tggtcgacgg cgggtatacc gcacagtga                           759
```

<210> SEQ ID NO 84
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 84

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Thr
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240
```

Ser Glu Phe Val Val Asp Gly Gly Tyr Thr Ala Gln
            245                 250

<210> SEQ ID NO 85
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 85

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgaacaa aagcgttgaa     300
gacactacca cggaggaatg gcgcaaactg ttgtccgtta atctggatag tgttttttc      360
ggcacccgtc tgggcattcg ccgcatgaag aataaaggct gggcgctag catcatcaat      420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg aagaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 86
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 86

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Asn
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

```
Gly Ala Val Arg Ile Met Ser Lys Ser Ala Leu Asp Cys Ala Val
            165                 170                 175

Lys Asp Tyr Asp Val Arg Val Asn Thr Val His Pro Gly Ala Ile Lys
        180                 185                 190

Thr Pro Leu Thr Asp Lys Phe Pro Gly Gly Glu Met Ile Ser Gln
            195                 200                 205

Arg Thr Lys Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 87
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 87
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggcct ctctgaacaa aagcgttgaa      300
gacactacca cggaggaatg gcgcaaactg ttgtccgtta atctggatag tgttttttc     360 ggcacccgtc tgggcattcg ccgcatgaag aataaaggct gggcgctag catcatcaat     420 atgagctcga tcagtgggct ggtaggcgat ccgatgttgg ggtgttacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                             759
```

```
<210> SEQ ID NO 88
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 88

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

Phe Gly Pro Val Thr Thr Val Val Asn Asn Ala Gly Ala Ser Leu Asn
                 85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Cys Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 89
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 89
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcagggcct ctctgaacaa agcgttgaa        300 gacactacca cggaggaatg cgcaaactg ttgtccgtta atctggatag tgttttttc        360 ggcacccgtc tgggcattcg ccgcatgaag aataaaggct gggcgctag catcatcaat       420 atgagctcga tcagtgggct ggtaggcgat ccgatgttgg gggcatacaa cgcttccaag      480
ggggcggtac gtatcatgtc gaaaagcgca gcgctggatt gcgcagtgaa ggactacgat       540
gtgcgtgtca acacagtaca tccgggcgct atcaagaccc cgctgactga taaatttcca       600
attggtgggg aaatgatctc acagcgtacg agaaccccta tgggccacat tggtgaaccg       660
aatgacgtgg catggatctg tgtgtacctg gcatctgacg aatcgaaatt tgcgacgggt       720
agcgaatttg tggtcgacgg cgggtatacc gcacagtga                             759

<210> SEQ ID NO 90
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 90

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Asn
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ile Gly Gly Glu Met Ile Ser Gln
        195                 200                 205

Arg Thr Arg Thr Pro Met Gly His Ile Gly Glu Pro Asn Asp Val Ala
210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 91
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 91

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgaacaa agcgttgaa      300
gacactacca cggaggaatg gcgcaaactg ttgtccgtta atctggatag tgttttttc     360
ggcacccgtc tgggcattcg ccgcatgaag aataaaggct gggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ttgggtgggg aaatgatctc acagcgtacg agaaccccta tgggccacat tggtgaaccg     660
```

```
aatgacgtgg catggatctg tgtgtacctg gcatctgacg aatcgaaatt tgcgacgggt    720
agcgaatttg tggtcgacgg cgggtatacc gcacagtga                          759
```

<210> SEQ ID NO 92
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 92

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Asn
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Leu Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 93
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 93

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
```

```
cagcacgatg catccgatga agcaggctgg acgaaactgt tcgacaccac cgaggaggca    240
ttcggcccgg ttacgaccgt cgtgaacaat gcagggcct ctctgaacaa aagcgttgaa    300
gacactacca cggaggaatg gcgcaaactg ttgtccgtta atctggatag tgttttttc    360 ggcacccgtc tgggcattcg ccgcatgaag aataaaggct tgggcgctag catcatcaat    420
atgagctcga tcagtgggct ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
gctggtgggg aaatgatctc acagcgtacg agaaccccta tgggccacat tggtgaaccg    660
aatgacgtgg catggatctg tgtgtacctg gcatctgacg aatcgaaatt tgcgacgggt    720
agcgaatttg tggtcgacgg cgggtatacc gcacagtga                          759
```

```
<210> SEQ ID NO 94
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 94

Met Thr Asn Arg Leu Lys Ser Lys Val Ala Ile Val Thr Gly Gly Thr
 1               5                  10                  15

Gln Gly Ile Gly Leu Ala Ile Ala Asp Lys Phe Val Glu Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Ala
     50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ala Ser Leu Asn
                 85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 95
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 95
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat cgttttgtc      180 cagcacgatg catccgatga agcaggctgg acgaaactgt tcgacaccac cgaggaggca     240
ttcggcccgg ttacgaccgt cgtgaacaat gcaggggcct ctgtgaacaa agcgttgaa      300 gacactacca cggaggaatg gcgcaaactg ttgtccgtta atctggatag tgttttttc      360 ggcacccgtc tgggcattca gcgcatgaag aataaaggct gggcgctag catcatcaat     420 atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttccg     600
ggtggtgggg aaatgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759

<210> SEQ ID NO 96
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 96
```

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Val Asn
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys

```
            180                 185                 190
Thr Pro Leu Thr Asp Lys Phe Pro Gly Gly Gly Glu Met Ile Ser Gln
            195                 200                 205

Arg Thr Lys Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
            245                 250

<210> SEQ ID NO 97
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 97
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctatgaacaa agcgttgaa      300 gacactacca cggaggaatg gcgcaaactg ttgtccgtta atctggatag tgttttttc      360 ggcacccgtc tgggcattcg ccgcatgaag aataaaggct gggcgctag catcatcaat     420 atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
attggtgggg aaatgatctc acagcgtacg agaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 98
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 98

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Met Asn
                85                  90                  95

Lys Ser Val Glu Asp Thr Thr Thr Glu Glu Trp Arg Lys Leu Leu Ser
```

```
                100             105                 110
Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
            130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ile Gly Gly Glu Met Ile Ser Gln
            195                 200                 205

Arg Thr Arg Thr Pro Met Gly His Ile Gly Glu Pro Asn Asp Val Ala
            210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 99
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 99
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa aagcgttgaa     300
gacactacca cggaggaatg gcgcaaactg ttgtccgtta atctggatag tgttttttc     360 ggcacccgtc tgggcattcg ccgcatgaag aataaaggct tgggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
gcaggtgggg aaatgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759
```

```
<210> SEQ ID NO 100
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 100

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
```

```
                        20                  25                  30
Lys Val Val Ile Thr Gly Arg Arg Ala Asp Val Gly Glu Lys Ala Ala
                35                  40                  45

Lys Ser Ile Gly Gly Thr Asp Val Ile Arg Phe Val Gln His Asp Ala
            50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                    85                  90                  95

Lys Ser Val Glu Asp Thr Thr Thr Glu Glu Trp Arg Lys Leu Leu Ser
                100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
        130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
                180                 185                 190

Thr Pro Leu Thr Asp Lys Phe Pro Ala Gly Gly Glu Met Ile Ser Gln
            195                 200                 205

Arg Thr Lys Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 101
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 101
atgaccaacc gtctgaagag caaagtagcc atcgtaaccg gcgggaccca gggtatcggt      60
tttgcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggccct ctctgcctaa aagcgttgaa     300
gacactacca cggaggaatg gaaaaaactg ttgtccgtta atctggatgg cgttttttc      360 ggcacccgtc tgggcattcg ccgcatgaag aataaaggct gggcgctag catcatcaat      420 atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 102
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 102

Met Thr Asn Arg Leu Lys Ser Lys Val Ala Ile Val Thr Gly Gly Thr
1               5                   10                  15

Gln Gly Ile Gly Phe Ala Ile Ala Arg Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Ala
65                  70                  75                  80

Phe Gly Pro Val Thr Thr Val Asn Asn Ala Gly Ala Ser Leu Pro
                85                  90                  95

Lys Ser Val Glu Asp Thr Thr Glu Glu Trp Lys Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 103
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 103
atgaccaacc gtctgaagag caaagtagcc atcgtaaccg gcgggaccca gggtatcggt      60
cgcgcaatcg cccgcaaatt tgtagaggag ggtgcgaaag tagttatcac cggtcgccgt     120
gcagatgtag gtgaaaaggc cgccaaatca atcggcggta ctgatgttat cgctttgtc     180 cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300

-continued

```
gacactacca cggaggaatg gaaaaaactg ttgtccgtta atctggatgg cgttttttc     360 ggcacccgtc tgggcattcg ccgcatgaag aataaaggct tgggcgctag catcatcaat     420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                           759
```

```
<210> SEQ ID NO 104
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 104
```

```
Met Thr Asn Arg Leu Lys Ser Lys Val Ala Ile Val Thr Gly Gly Thr
1               5                   10                  15

Gln Gly Ile Gly Arg Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Lys Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 105
<211> LENGTH: 759
<212> TYPE: DNA
<213> ORGANISM: Artificial Sequence
```

<220> FEATURE:
<223> OTHER INFORMATION: Variant of L. kefir ketoreductase

<400> SEQUENCE: 105

```
atgaccaacc gtctgaagag caaagtagcc atcgtaaccg gcgggaccca gggtatcggt      60
tttgcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggcct ctctgcctaa aagcgttgaa      300
gacactacca cggaggaatg gaaaaaactg ttgtccgtta atctggatag tgttttttc      360
ggcacccgtc tgggcattaa gcgcatgaag aataaaggct gggcgctag catcatcaat      420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaacccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 106
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 106

```
Met Thr Asn Arg Leu Lys Ser Lys Val Ala Ile Val Thr Gly Gly Thr
1               5                   10                  15

Gln Gly Ile Gly Phe Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Lys Lys Leu Leu Ser
            100                 105                 110

Val Asn Leu Asp Ser Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205
```

Arg Thr Arg Thr Pro Met Gly His Ile Gly Glu Pro Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 107
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 107
atgaccaacc gtctgaagag caaagtagcc atcgtaaccg gcgggaccca gggtatcggt      60
cgcgcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gaaaaaactg ttgtccgtta atctggatgg cgttttttc      360 ggcacccgtc tgggcattcg ccgcatgaag aataaaggct gggcgctag catcatcaat      420 atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759

<210> SEQ ID NO 108
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 108

Met Thr Asn Arg Leu Lys Ser Lys Val Ala Ile Val Thr Gly Gly Thr
1               5                   10                  15

Gln Gly Ile Gly Arg Ala Ile Ala Arg Lys Phe Val Glu Glu Gly Ala
            20                  25                  30

Lys Val Val Ile Thr Gly Arg Arg Ala Asp Val Gly Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Lys Lys Leu Leu Ser
            100                 105                 110

Val Asn Leu Asp Gly Val Phe Phe Gly Thr Arg Leu Gly Ile Arg Arg
        115                 120                 125

```
Met Lys Asn Lys Gly Leu Gly Ala Ser Ile Ile Asn Met Ser Ser Ile
            130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
            210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 109
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 109
atgaccaacc gtctgaagag caaagtagcc atcgtaaccg gcgggaccca gggtatcggt      60
tttgcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt cgacaccac cgaggaggca     240 ttcggcccgg ttacgaccgt cgtgaacaat gcagggcct ctctgcctaa aagcgttgaa     300
gacactacca cggaggaatg gaaaaaactg ttgtccgtta atctggatgg cgtttttttc     360
ggcacccgtc tgggcattcg ccgcatgaag aataaaggct tgggcgctag catcatcaat     420
atgagctcga tcagtgggat ggtaggcgat ccgatgttgg gggcatacaa cgcttccaag     480
ggggcgatcc gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaacccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                           759

<210> SEQ ID NO 110
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 110

Met Thr Asn Arg Leu Lys Ser Lys Val Ala Ile Val Thr Gly Gly Thr
1               5                   10                  15

Gln Gly Ile Gly Phe Ala Ile Ala Arg Lys Phe Val Glu Glu Gly Ala
                20                  25                  30

Lys Val Val Ile Thr Gly Arg Arg Ala Asp Val Gly Glu Lys Ala Ala
            35                  40                  45
```

-continued

```
Lys Ser Ile Gly Gly Thr Asp Val Ile Arg Phe Val Gln His Asp Ala
 50                  55                  60
Ser Asp Glu Ala Gly Trp Thr Lys Leu Phe Asp Thr Thr Glu Glu Ala
 65                  70                  75                  80
Phe Gly Pro Val Thr Thr Val Val Asn Asn Ala Gly Ala Ser Leu Pro
                 85                  90                  95
Lys Ser Val Glu Asp Thr Thr Thr Glu Glu Trp Lys Lys Leu Leu Ser
                100                 105                 110
Val Asn Leu Asp Gly Val Phe Phe Gly Thr Arg Leu Gly Ile Arg Arg
            115                 120                 125
Met Lys Asn Lys Gly Leu Gly Ala Ser Ile Ile Asn Met Ser Ser Ile
130                 135                 140
Ser Gly Met Val Gly Asp Pro Met Leu Gly Ala Tyr Asn Ala Ser Lys
145                 150                 155                 160
Gly Ala Ile Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
                180                 185                 190
Thr Pro Leu Thr Asp Lys Phe Pro Gly Gly Glu Met Ile Ser Gln
            195                 200                 205
Arg Thr Arg Thr Pro Met Gly His Ile Gly Glu Pro Asp Asp Val Ala
210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

```
<210> SEQ ID NO 111
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 111
atgaccaacc gtctgaagag caaagtagcc atcgtaaccg gcgggaccca gggtatcggt      60
cgcgcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gcgcaaactg ttgtccgtta atctggatgg cgttttttc      360
ggcacccgtc tgggcattcg ccgcatgaag aataaaggct gggcgctag  catcatcaat     420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tggccacat  tggtgaaccg     660
gatgacgtgg catggatctg tgtgtacctg gcatctgacg aatcgaaatt tgcgacgggt     720
agcgaatttg tggtcgacgg cgggtatacc gcacagtga                           759
```

```
<210> SEQ ID NO 112
<211> LENGTH: 252
```

<212> TYPE: PRT
<213> ORGANISM: Artificial Sequence
<220> FEATURE:
<223> OTHER INFORMATION: Variant of L. kefir ketoreductase

<400> SEQUENCE: 112

Met Thr Asn Arg Leu Lys Ser Lys Val Ala Ile Val Thr Gly Gly Thr
1               5                   10                  15

Gln Gly Ile Gly Arg Ala Ile Ala Asp Lys Phe Val Glu Glu Gly Ala
            20                  25                  30

Lys Val Ile Thr Gly Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ala Ser Leu Pro
                85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Arg Arg
            115                 120                 125

Met Lys Asn Lys Gly Leu Gly Ala Ser Ile Ile Asn Met Ser Ser Ile
130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
            195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 113
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 113
atgaccaacc gtctgaagag caaagtagcc atcgtaaccg gcgggaccca gggtatcggt     60
cgcgcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggggcct ctctgcctaa agcgttgaa     300 gacactacca cggaggaatg gcgcaaactg ttgtccgtta atctggatgg tgttttttc    360 ggcacccgtc tgggcattaa gcgcatgaag aataaaggct gggcgctag catcatcaat    420

```
atgagctcga tcagtgggat ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtggtgggg aaatgatctc acagcgtacg agaaccccta tgggccacat tggtgaaccg    660
gatgacgtgg catggatctg tgtgtacctg gcatctgacg aatcgaaatt tgcgacgggt    720
agcgaatttg tggtcgacgg cgggtatacc gcacagtga                          759
```

<210> SEQ ID NO 114
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 114

```
Met Thr Asn Arg Leu Lys Ser Lys Val Ala Ile Val Thr Gly Gly Thr
1               5                   10                  15

Gln Gly Ile Gly Arg Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 115
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 115

```
atgaccaacc gtctgaagag caaagtagcc atcgtaaccg gcgggaccca gggtatcggt     60
ttggcaatcg ccgataaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggggcct ctctgcctaa aagcgttgaa    300
gacactacca cggaggaatg gcgcaaactg ttgtccgtta atctggatgg cgttttttc     360 ggcacccgtc tgggcattcg ccgcatgaag aataaaggct gggcgctag catcatcaat    420 atgagctcga tcagtgggat ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtggtgggg aaatgatctc acagcgtacg agaaccccta tgggccacat tggtgaaccg    660
gatgacgtgg catggatctg tgtgtacctg gcatctgacg aatcgaaatt tgcgacgggt    720
agcgaatttg tggtcgacgg cgggtatacc gcacagtga                          759
```

<210> SEQ ID NO 116
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 116

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asp Asp Val Ala
    210                 215                 220
```

```
Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 117
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 117
atgaccaacc gtctgaagag caaagtagcc atcgtaaccg gcgggaccca gggtatcggt        60
ttagcaatcg cccgcaaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcaggggcct ctctgcctaa aagcgttgaa       300
gacactacca cggaggaatg ggacaaactg ttgtccgtta atctggatgg cgttttttc       360 ggcacccgtc tgggcattaa agcgatgaag aataaaggct gggcgctag catcatcaat       420 atgagctcga tcagtgggat ggtaggcgat ccgatgttgg gggcatacaa cgcttccaag       480
ggggcggtac gtatcatgtc gaaaagcgca gcgctggatt cgcagtgaa ggactacgat        540 gtgcgtgtca acacagtaca tccgggcgct atcaagaccc cgctgactga taaatttcca       600
ggtggtgggg aaatgatctc acagcgtacg agaaccccta tgggccacat tggtgaaccg       660
gatgacgtgg catggatctg tgtgtacctg gcatctgacg aatcgaaatt tgcgacgggt       720
agcgaatttg tggtcgacgg cgggtatacc gcacagtga                            759

<210> SEQ ID NO 118
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 118

Met Thr Asn Arg Leu Lys Ser Lys Val Ala Ile Val Thr Gly Gly Thr
1               5                   10                  15

Gln Gly Ile Gly Leu Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Asp Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140
```

```
Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 119
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 119

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggggcct ctctgcctaa aagcgttgaa     300
gacactacca cggaggaatg cgcaaactg ttgtccgtta atctggatgg cgttttttc      360
ggcacccgtc tgggcattcg ccgcatgaag aataaaggct gggcgctag catcatcaat     420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaacccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 120
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 120

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60
```

```
Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ala Ser Leu Pro
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 121
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 121
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gaaaaaactg ttgtccgtta atctggatgg cgttttttc      360 ggcacccgtc tgggcattaa gcgcatgaag aataaaggct tgggcgctag catcatcaat     420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                            759

<210> SEQ ID NO 122
<211> LENGTH: 252
<212> TYPE: PRT
<213> ORGANISM: Artificial Sequence
<220> FEATURE:
<223> OTHER INFORMATION: Variant of L. kefir ketoreductase
```

<400> SEQUENCE: 122

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Lys Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asp Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 123
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 123
atgaccaacc gtctgaagag caaagtagcc atcgtaaccg gcgggaccca gggtatcggt     60
cgcgcaatcg cccgcaaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggcct ctctgcctaa aagcgttgaa    300
gacactacca cggaggaatg gcgcaaactg ttgtccgtta atctggatgg cgttttttc    360 ggcacccgtc tgggcattaa gcgcatgaag aataaaggct gggcgctag catcatcaat    420 atgagctcga tcagtgggct ggtaggcgat ccgatgttgg gggcatacaa cgcttccaag    480
ggggcggtac gtatcatgtc gaaaagcgca gcgctggatt gcgcagtgaa ggactacgat    540

```
gtgcgtgtca acacagtaca tccgggcgct atcaagaccc cgctgactga taaatttcca    600
ggtggtgggg aaatgatctc acagcgtacg agaacccta tgggccacat tggtgaaccg     660
gatgacgtgg catggatctg tgtgtacctg gcatctgacg aatcgaaatt tgcgacgggt    720
agcgaatttg tggtcgacgg cgggtatacc gcacagtga                          759
```

```
<210> SEQ ID NO 124
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 124

Met Thr Asn Arg Leu Lys Ser Lys Val Ala Ile Val Thr Gly Gly Thr
1               5                   10                  15

Gln Gly Ile Gly Arg Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

```
<210> SEQ ID NO 125
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 125
atgaccaacc gtctgaagag caaagtagcc atcgtaaccg gcgggaccca gggtatcggt    60
ttagcaatcg cccgcaaatt tgtagaggag ggtgcgaaag tagttatcac cggtcgccgt    120
```

```
gcagatgtag gtgaaaaggc cgccaaatca atcggcggta ctgatgttat tcgctttgtc        180
cagcacgatg catccgatga agcaggctgg acgaaactgt tcgacaccac cgaggaggca        240
ttcggcccgg ttacgaccgt cgtgaacaat gcagggccct ctctgcctaa aagcgttgaa        300
gacactacca cggaggaatg gcgcaaactg ttgtccgtta atctggatgg cgttttttc         360 ggcacccgtc tgggcattaa cgcatgaag aataaaggct tgggcgctag catcatcaat         420
atgagctcga tcagtgggct ggtaggcgat ccgatgttgg gggcatacaa cgcttccaag        480
ggggcggtac gtatcatgtc gaaaagcgca gcgctggatt gcgcagtgaa ggactacgat        540
gtgcgtgtca acacagtaca tccgggcgct atcaagaccc cgctgactga taaatttcca        600
ggtggtgggg aaatgatctc acagcgtacg agaacccta tgggccacat tggtgaaccg         660
aatgacgtgg catggatctg tgtgtacctg gcatctgacg aatcgaaatt tgcgacgggt        720
agcgaatttg tggtcgacgg cgggtatacc gcacagtga                              759
```

```
<210> SEQ ID NO 126
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 126

Met Thr Asn Arg Leu Lys Ser Lys Val Ala Ile Val Thr Gly Gly Thr
1               5                   10                  15

Gln Gly Ile Gly Leu Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
```

<210> SEQ ID NO 127
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 127

```
atgaccaacc gtctgaagag caaagtagcc atcgtaaccg gcgggaccca gggtatcggt      60
ttagcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gaaaaaactg ttgtccgtta atctggatgg cgttttttc     360
ggcacccgtc tgggcattaa agcgcatgaag aataaaggct tgggcgctag catcatcaat     420
atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 128
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 128

```
Met Thr Asn Arg Leu Lys Ser Lys Val Ala Ile Val Thr Gly Gly Thr
1               5                   10                  15

Gln Gly Ile Gly Leu Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Lys Lys Leu Leu Ser
            100                 105                 110

Val Asn Leu Asp Gly Val Phe Phe Gly Thr Arg Leu Gly Ile Lys Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
```

```
            165                 170                 175
Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asp Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 129
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 129
atgaccaacc gtctgaagag caaagtagcc atcgtaaccg gcgggaccca gggtatcggt     60
ttagcaatcg cccgcaaatt tgtagaggag ggtgcgaaag tagttatcac cggtcgccgt    120
gcagatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggcct ctctgcctaa aagcgttgaa     300
gacactacca cggaggaatg cgcaaactg ttgtccgtta atctggatag tgttttttc      360 ggcacccgtc tgggcattcg ccgcatgaag aataaaggct ggggcgctag catcatcaat    420
atgagctcga tcagtgggat ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
ggtggtgggg aaatgatctc acagcgtacg agaacccta tgggccacat tggtgaaccg     660
gatgacgtgg catggatctg tgtgtacctg gcatctgacg aatcgaaatt tgcgacgggt    720
agcgaatttg tggtcgacgg cgggtatacc gcacagtga                          759

<210> SEQ ID NO 130
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 130

Met Thr Asn Arg Leu Lys Ser Lys Val Ala Ile Val Thr Gly Gly Thr
1               5                   10                  15

Gln Gly Ile Gly Leu Ala Ile Ala Arg Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
```

```
                85                  90                  95
Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
            115                 120                 125

Met Lys Asn Lys Gly Leu Gly Ala Ser Ile Ile Asn Met Ser Ser Ile
        130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
            195                 200                 205

Arg Thr Arg Thr Pro Met Gly His Ile Gly Glu Pro Asp Asp Val Ala
        210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 131
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 131
atgaccaacc gtctgaagag caaagtagcc atcgtaaccg gcgggaccca gggtatcggt      60
cgcgcaatcg cccgcaaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggggcct ctctgcctaa aagcgttgaa     300
gacactacca cggaggaatg gcgcaaactg ttgtccgtta atctggatgg cgttttttc      360 ggcacccgtc tgggcattcg ccgcatgaag aataaaggct gggcgctag catcatcaat     420 atgagctcga tcagtgggat ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
ggtggtgggg aaatgatctc acagcgtacg agaaccccta tgggccacat tggtgaaccg     660
gatgacgtgg catggatctg tgtgtacctg gcatctgacg aatcgaaatt tgcgacgggt     720
agcgaatttg tggtcgacgg cgggtatacc gcacagtga                            759

<210> SEQ ID NO 132
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 132

Met Thr Asn Arg Leu Lys Ser Lys Val Ala Ile Val Thr Gly Gly Thr
```

```
              1               5                  10                 15
            Gln Gly Ile Gly Arg Ala Ile Ala Arg Lys Phe Val Glu Glu Gly Ala
                             20                 25                 30
            Lys Val Val Ile Thr Gly Arg Arg Ala Asp Val Gly Glu Lys Ala Ala
                        35                 40                 45
            Lys Ser Ile Gly Gly Thr Asp Val Ile Arg Phe Val Gln His Asp Ala
                   50                 55                 60
            Ser Asp Glu Ala Gly Trp Thr Lys Leu Phe Asp Thr Thr Glu Glu Ala
             65                 70                 75                 80
            Phe Gly Pro Val Thr Thr Val Asn Asn Ala Gly Ala Ser Leu Pro
                             85                 90                 95
            Lys Ser Val Glu Asp Thr Thr Glu Glu Trp Arg Lys Leu Leu Ser
                       100                105                110
            Val Asn Leu Asp Gly Val Phe Phe Gly Thr Arg Leu Gly Ile Arg Arg
                       115                120                125
            Met Lys Asn Lys Gly Leu Gly Ala Ser Ile Ile Asn Met Ser Ser Ile
                   130                135                140
            Ser Gly Met Val Gly Asp Pro Met Leu Gly Ala Tyr Asn Ala Ser Lys
            145                150                155                160
            Gly Ala Val Arg Ile Met Ser Lys Ser Ala Ala Leu Asp Cys Ala Val
                            165                170                175
            Lys Asp Tyr Asp Val Arg Val Asn Thr Val His Pro Gly Ala Ile Lys
                       180                185                190
            Thr Pro Leu Thr Asp Lys Phe Pro Gly Gly Gly Glu Met Ile Ser Gln
                       195                200                205
            Arg Thr Arg Thr Pro Met Gly His Ile Gly Glu Pro Asp Asp Val Ala
                  210                215                220
            Trp Ile Cys Val Tyr Leu Ala Ser Asp Glu Ser Lys Phe Ala Thr Gly
            225                230                235                240
            Ser Glu Phe Val Val Asp Gly Gly Tyr Thr Ala Gln
                           245                250
```

<210> SEQ ID NO 133
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 133

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggactc tctgcctaa aagcgttgaa    300
gacactacca cggaggaatg gcgcaaactg ttgtccgtta atctggatag tgttttttc    360
ggcacccgtc tgggcattcg ccgcatgaag aataaaggct gggcgctag catcatcaat   420
atgagctcga tcagtgggct ggtaggcgat ccgatgttgg gggcatacaa cgcttccaag   480
ggggcggtac gtatcatgtc gaaaagcgca gcgctggatt gcgcagtgaa ggactacgat   540
gtgcgtgtca acacagtaca tccgggcgct atcaagaccc cgctgactga taaatttcca   600
ggtggtgggg aaatgatctc acagcgtacg agaaccccta tgggccacat tggtgaaccg   660
```

```
aatgacgtgg catggatctg tgtgtacctg gcatctgacg aatcgaaatt tgcgacgggt    720
agcgaatttg tggtcgacgg cgggtatacc gcacagtga                           759
```

<210> SEQ ID NO 134
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 134

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Thr Ser Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 135
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 135

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
```

```
ttcggcccgg ttacgaccgt cgtgaacaat gcaggggccg cgctgcctaa aagcgttgaa      300
gacactacca cggaggaatg gcgcaaactg ttgtccgtta atctggatag tgttttttc       360 ggcacccgtc tgggcattcg ccgcatgaag aataaaggct tgggcgctag catcatcaat      420
atgagctcga tcagtgggct ggtaggcgat ccgatgttgg gggcatacaa cgcttccaag      480
ggggcggtac gtatcatgtc gaaaagcgca gcgctggatt gcgcagtgaa ggactacgat      540
gtgcgtgtca acacagtaca tccgggcgct atcaagaccc cgctgactga taaatttcca      600
ggtggtgggg aaatgatctc acagcgtacg agaaccccta tgggccacat tggtgaaccg      660
aatgacgtgg catggatctg tgtgtacctg gcatctgacg aatcgaaatt tgcgacgggt      720
agcgaatttg tggtcgacgg cgggtatacc gcacagtga                            759
```

<210> SEQ ID NO 136
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 136

```
Met Thr Asn Arg Leu Lys Ser Lys Val Ala Ile Val Thr Gly Gly Thr
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ala Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Gly Gly Gly Glu Met Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 137

<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 137

```
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcagggcct ctctgcctaa aagcgttgaa        300
gacactacca cggaggaatg gcgcaaactg ttgtccgtta atctggatag tgttttttc        360
ggcacccgtc tgggcattcg ccgcatgaag aataaaggct gggcgctag catcatcaat       420
atgagctcga tcagtgggct ggtaggcgat ccgatgttgg gggcatacaa cgcttccaag       480
ggggcggtac gtatcatgtc gaaaagcgca gcgctggatt gcgcagtgaa ggactacgat       540
gtgcgtgtca acacagtaca tccgggcgct atcaagaccc cgctgactga taaatttcca       600
ggtggtgggg aagtgatctc acagcgtacg agaacccta tgggccacat tggtgaaccg        660
aatgacgtgg catggatctg tgtgtacctg gcatctgacg aatcgaaatt tgcgacgggt       720
agcgaatttg tggtcgacgg cgggtatacc gcacagtga                              759
```

<210> SEQ ID NO 138
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 138

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ala Ser Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190
```

Thr Pro Leu Thr Asp Lys Phe Pro Gly Gly Gly Glu Val Ile Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
            245                 250

<210> SEQ ID NO 139
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 139

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa agcgttgaa      300
gacactacca cggaggaatg gcgcaaactg ttgtccgtta atctggatgc ggttttttc     360
ggcacccgtc tgggcattcg ccgcatgaag aataaaggct gggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
gcaggtgggg aaatgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                           759
```

<210> SEQ ID NO 140
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 140

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Val Glu Asp Thr Thr Thr Glu Glu Trp Arg Lys Leu Leu Ser
            100                 105                 110

```
Val Asn Leu Asp Ala Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Ala Gly Gly Glu Met Ile Ser Gln
        195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

```
<210> SEQ ID NO 141
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 141
atgaccaacc gtctgaagag caaagtagcc atcgtaaccg gcgggaccca gggtatcggt     60
ttggcaatcg ccgataaatt tgtagaggag ggtgcgaaag tagttatcac cggtcgccgt    120
gcagatgtag gtgaaaaggc cgccaaatca atcggcggta ctgatgttat cgctttgtc    180
cagcacgatg catccgatga agcaggctgg acgaaactgt tcgacaccac cgaggaggca    240
ttcggcccgg ttacgaccgt cgtgaacaat gcagggatct ctctgcctaa agcgttgaa    300
gacactacca cggaggaatg cgcaaactg ttgtccgtta atctggatgg ggtttttttc    360
ggcacccgtc tgggcattcg ccgcatgaag aataaaggct tgggcgctag catcatcaat    420
atgagctcga tcagtgggct ggtaggcgat ccgatgttgg gggcatacaa cgcttccaag    480
ggggcggtac gtatcatgtc gaaaagcgca gcgctggatt gcgcagtgaa ggactacgat    540
gtgcgtgtca acacagtaca tccgggcgct atcaagaccc cgctgactga taaatttcca    600
gcaggtgggg aaatgatctc acagcgtacg aaaacccta tgggccacat tggtgaaccg    660
aatgacgtgg catggatctg tgtgtacctg gcatctgacg aatcgaaatt tgcgacgggt    720
agcgaatttg tggtcgacgg cgggtatacc gcacagtga                          759
```

```
<210> SEQ ID NO 142
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 142

Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
```

```
Lys Val Val Ile Thr Gly Arg Arg Ala Asp Val Gly Glu Lys Ala Ala
            35                  40                  45
Lys Ser Ile Gly Gly Thr Asp Val Ile Arg Phe Val Gln His Asp Ala
        50                  55                  60
Ser Asp Glu Ala Gly Trp Thr Lys Leu Phe Asp Thr Thr Glu Glu Ala
 65                  70                  75                  80
Phe Gly Pro Val Thr Val Val Asn Asn Ala Gly Ile Ser Leu Pro
                 85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Arg Arg
            115                 120                 125
Met Lys Asn Lys Gly Leu Gly Ala Ser Ile Ile Asn Met Ser Ser Ile
        130                 135                 140
Ser Gly Leu Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Ala Gly Gly Glu Met Ile Ser Gln
        195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 143
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 143

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag tgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa aagcgttgaa     300
gacactacca cggaggaatg gcgcaaactg ttgtccgtta atctggatag tgtttttttc     360
ggcacccgtc tgggcattcg ccgcatgaag aataaaggct gggcgctag catcatcaat     420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatggcca     600
gcaggtgggg aaatgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                             759
```

<210> SEQ ID NO 144
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 144

```
Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ser Leu Pro
                85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Trp Pro Ala Gly Gly Glu Met Ile Ser Gln
        195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 145
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 145

| | |
|---|---|
| atgaccaacc gtctgaagag caaagtagcc atcgtaaccg gcgggaccca gggtatcggt | 60 |
| ttggcaatcg ccgataaatt tgtagaggag ggtgcgaaag tagttatcac cggtcgccgt | 120 |
| gcagatgtag gtgaaaaggc cgccaaatca atcggcggta ctgatgttat tcgctttgtc | 180 |
| cagcacgatg catccgatga agcaggctgg acgaaactgt tcgacaccac cgaggaggca | 240 |
| ttcggcccgg ttacgaccgt cgtgaacaat gcagggatct ctctgcctaa agcgttgaa | 300 |
| gacactacca cggaggaatg cgcaaactg ttgtccgtta atctggatag tgttttttc | 360 |

```
ggcacccgtc tgggcattcg ccgcatgaag aataaaggct tgggcgctag catcatcaat      420
atgagctcga tcagtgggat ggtaggcgat ccgatgttgg gggcatacaa cgcttccaag      480
ggggcggtac gtatcatgtc gaaaagcgca gcgctggatt gcgcagtgaa ggactacgat      540
gtgcgtgtca acacagtaca tccgggcgct atcaagaccc cgctgactga taaatttcca      600
gcaggtgggg aaatgatctc acagcgtacg aaaccccta tgggccacat tggtgaaccg       660
aatgacgtgg catggatctg tgtgtacctg gcatctgacg aatcgaaatt tgcgacgggt      720
agcgaatttg tggtcgacgg cgggtatacc gcacagtga                             759
```

<210> SEQ ID NO 146
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 146

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Met Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Met Ile Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 147
<211> LENGTH: 759
<212> TYPE: DNA
<213> ORGANISM: Artificial Sequence
<220> FEATURE:

<223> OTHER INFORMATION: Variant of L. kefir ketoreductase

<400> SEQUENCE: 147

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg tgtccgatga agcaggctgg acgaaactgt tcgacaccac cgaggaggca     240
ttcggcccgg ttacgaccgt cgtgaacaat gcagggatct ctctgcctaa aagcgttgaa     300
gacactacca cggaggaatg gcgcaaactg ttgtccgtta atctggatag tgttttttc      360
ggcacccgtc tgggcattcg ccgcatgaag aataaaggct gggcgctag catcatcaat      420
atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
gcaggtgggg aaatgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 148
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 148

```
Met Thr Asn Arg Leu Lys Ser Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Met Ile Ser Gln
        195                 200                 205
```

```
Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 149
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 149
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa aagcgttgaa     300
gacactacca cggaggaatg gcgcaaactg ttgtccgtta atctggatag tgttttttc      360 ggcacccgtc tgggcattcg ccgcatgaag aataaaggct gggcgctag catcatcaat      420 atgagctcga tcagtgggct ggtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
gcaggtgggg aaatgatctc acagcgtacg aaaacccta tgggccacat tggtgaaccg      660
aatgacattg catggatctg tgtgtacctg gcatctgacg aatcgaaatt tgcgacgggt     720
agcgaatttg tggtcgacgg cgggtatacc gcacagtga                            759

<210> SEQ ID NO 150
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 150

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Val Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125
```

```
Met Lys Asn Lys Gly Leu Gly Ala Ser Ile Ile Asn Met Ser Ser Ile
    130                 135                 140
Ser Gly Leu Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Ala Gly Gly Glu Met Ile Ser Gln
        195                 200                 205
Arg Thr Lys Thr Pro Met Gly His Ile Gly Glu Pro Asn Asp Ile Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 151
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 151

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcgcggta  ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatct ctctgcctaa agcgttgaa   300
gacactacca cggaggaatg cgcaaactg  ttgtccgtta atctggatag tgttttttc   360
ggcacccgtc tgggcattcg ccgcatgaag aataaaggct tgggcgctag catcatcaat   420
atgagctcga tcagtgggct ggtaggcgat ccgatgttgg gggcatacaa cgcttccaag   480
ggggcggtac gtatcatgtc gaaaagcgca gcgctggatt gcgcagtgaa ggactacgat   540
gtgcgtgtca acacagtaca tccgggcgct atcaagaccc cgatgactga taaatttcca   600
gcaggtgggg aaatgatctc acagcgtacg aaaaccccta tgggccacat tggtgaaccg   660
aatgacgtgg catggatctg tgtgtacctg gcatctgacg aatcgaaatt tgcgacgggt   720
agcgaatttg tggtcgacgg cgggtatacc gcacagtga                          759
```

<210> SEQ ID NO 152
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 152

```
Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
```

```
Lys Ser Ile Gly Gly Thr Asp Val Ile Arg Phe Val Gln His Asp Ala
 50                  55                  60
Ser Asp Glu Ala Gly Trp Thr Lys Leu Phe Asp Thr Thr Glu Glu Ala
 65                  70                  75                  80
Phe Gly Pro Val Thr Val Val Asn Asn Ala Gly Ile Ser Leu Pro
                 85                  90                  95
Lys Ser Val Glu Asp Thr Thr Glu Glu Trp Arg Lys Leu Leu Ser
                100                 105                 110
Val Asn Leu Asp Ser Val Phe Phe Gly Thr Arg Leu Gly Ile Arg Arg
                115                 120                 125
Met Lys Asn Lys Gly Leu Gly Ala Ser Ile Ile Asn Met Ser Ser Ile
130                 135                 140
Ser Gly Leu Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
                180                 185                 190
Thr Pro Met Thr Asp Lys Phe Pro Ala Gly Gly Glu Met Ile Ser Gln
                195                 200                 205
Arg Thr Lys Thr Pro Met Gly His Ile Gly Glu Pro Asn Asp Val Ala
210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 153
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 153

```
atgaccaacc gtctgaagag caaagtagcc atcgtaaccg gcgggaccca gggtatcggt        60
ttggcaatcg ccgataaatt tgtagaggag ggtgcgaaag tagttatcac cggtcgccgt       120
gcagatgtag tgaaaaggc cgccaaatca atcggcggta ctgatgttat tcgctttgtc        180
cagcacgatg catccgatga agcaggctgg acgaaactgt tcgacaccac cgaggaggca       240
ttcggcccgg ttacgaccgt cgtgaacaat gcagggatct ctctgcctaa aagcgttgaa       300
gacactacca cggaggaatg gcgcaaactg ttgtccgtta atctggatag tgttttttc        360
ggcacccgtc tgggcattcg ccgcatgaag aataaaggct gggcgctag catcatcaat       420
atgagctcga tcagtgggat tgtaggcgat ccgatgttgg gggcatacaa cgcttccaag       480
ggggcggtac gtatcatgtc gaaaagcgca gcgctggatt gcgcagtgaa ggactacgat       540
gtgcgtgtca acacagtaca tccgggcgct atcaagaccc cgctgactga taaatttcca       600
gcaggtgggg aaatgatctc acagcgtacg aaaaccccta tgggccacat tggtgaaccg       660
aatgacgtgg catggatctg tgtgtacctg gcatctgacg aatcgaaatt tgcgacgggt       720
agcgaatttg tggtcgacgg cgggtatacc gcacagtga                             759
```

<210> SEQ ID NO 154
<211> LENGTH: 252
<212> TYPE: PRT

<213> ORGANISM: Artificial Sequence
<220> FEATURE:
<223> OTHER INFORMATION: Variant of L. kefir ketoreductase

<400> SEQUENCE: 154

```
Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ser Leu Pro
                85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Ile Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Ala Ile Lys
            180                 185                 190
Thr Pro Leu Thr Asp Lys Phe Pro Ala Gly Gly Glu Met Ile Ser Gln
        195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ser Glu Phe Val Val Asp Gly Gly Tyr Thr Ala Gln
                245                 250
```

<210> SEQ ID NO 155
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 155

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa aagcctggaa     300
gacactacca cggaggaatg gcataaactg ttgtccgtta atctggatag tgttttttc      360
ggcacccgtc tgggcattcg ccgcatgaag aataaaggct gggcgctag catcatcaat      420
atgagctcga tcagtgggat cgtaggcgat ccgatgttgg gggcatacaa cgcttccaag     480
```

```
ggggcggtac gtatcatgtc gaaaagcgca gcgctggatt gcgcagtgaa ggactacgat      540
gtgcgtgtca acacagtaca tccgggcgct atcaagaccc cgctgactga taaatttcca      600
gcaggtgggg aagtgatctc acagcgtacg aaaaccccta tgggccacat tggtgaaccg      660
aatgacgtgg catgggtgtg tgtgtacctg gcatctgacg aatcgaaatt tgcgacgggt      720
agcgaatttg tggtcgacgg cgggtatacc gcacagtga                            759
```

<210> SEQ ID NO 156
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 156

```
Met Thr Asn Arg Leu Lys Ser Lys Val Ala Ile Val Thr Gly Gly Thr
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp His Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Ile Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Val Ile Ser Gln
        195                 200                 205

Arg Thr Lys Thr Pro Met Gly His Ile Gly Glu Pro Asn Asp Val Ala
    210                 215                 220

Trp Val Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 157
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 157

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatct ctctgcctaa aagcctggaa   300
gacactacca cggaggaatg gcataaactg ttgtccgtta atctggatag tgttttttc    360
ggcacccgtc tgggcattcg ccgcatgaag aataaaggct gggcgctag catcatcaat    420
atgagctcga tcagtgggat cgtaggcgat ccgatgttgg gggcatacaa cgcttccaag   480
ggggcggtac gtatcatgtc gaaaagcgca gcgctggatt gcgcagtgaa ggactacgat   540
gtgcgtgtca acacagtaca tccgggcgct atcaagaccc cgctgactga taaatttcca   600
gcaggtgggg aaatgatctc acagcgtacg aaaaccccta tgggccacat tggtgaaccg   660
aatgacgtgg catgggtgtg tgtgtacctg gcatctgacg aatcgaaatt tgcgacgggt   720
agcgaatttg tggtcgacgg cgggtatacc gcacagtga                          759
```

<210> SEQ ID NO 158
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 158

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp His Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Ile Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Met Ile Ser Gln
        195                 200                 205

Arg Thr Lys Thr Pro Met Gly His Ile Gly Glu Pro Asn Asp Val Ala
    210                 215                 220

Trp Val Cys Val Tyr Leu Ala Ser Asp Glu Ser Lys Phe Ala Thr Gly

```
225                 230                 235                 240
Ser Glu Phe Val Val Asp Gly Gly Tyr Thr Ala Gln
                245                 250
```

<210> SEQ ID NO 159
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 159

```
atgaccaacc gtctgaagag caaagtagcc atcgtaaccg gcgggaccca gggtatcggt     60
ttggcaatcg ccgataaatt tgtagaggag ggtgcgaaag tagttatcac cggtcgccgt    120
gcagatgtag gtgaaaaggc cgccaaatca atcggcggta ctgatgttat cgctttgtc    180
cagcacgatg catccgatga agcaggctgg acgaaactgt tcgacaccac cgaggaggca    240
ttcggcccgg ttacgaccgt cgtgaacaat gcagggatct ctctgcctaa agcctggaa    300
gacactacca cggaggaatg gcgcaaactg ttgtccgtta atctggatag tgttttttc    360
ggcacccgtc tgggcattcg ccgcatgaag aataaaggct gggcgctag catcatcaat    420
atgagctcga tcagtgggat cgtaggcgat ccgatgttgg gggcatacaa cgcttccaag    480
ggggcggtac gtatcatgtc gaaaagcgca cgcctggatt gcgcagtgaa ggactacgat    540
gtgcgtgtca acacagtaca tccgggcgct atcaagaccc cgctgactga taaatttcca    600
gcaggtgggg aagtgatctc acagcgtacg aaaaccccta tgggccacat ggtgaaccg    660
aatgacgtgg catggatctg tgtgtacctg gcatctgacg aatcgaaatt tgcgacgggt    720
agcgaatttg tggtcgacgg cgggtatacc gcacagtga                          759
```

<210> SEQ ID NO 160
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 160

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Ile Val Gly Asp Pro Met Leu Gly Ala Tyr Asn Ala Ser Lys
```

```
                    145                 150                 155                 160
Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Glu Val Ile Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 161
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 161
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa agcctggaa      300 gacactacca cggaggaatg gcataaactg ttgtccgtta atctggatgg tgttttttc      360 ggcacccgtc tgggcattcg ccgcatgaag aataaaggct gggcgctag catcatcaat     420 atgagctcga tcagtgggat cgtaggcgat ccgatgttgg gggcatacaa cgcttccaag     480
ggggcggtac gtatcatgtc gaaaagcgca gcgctggatt gcgcagtgaa ggactacgat     540
gtgcgtgtca acacagtaca tccgggcgct atcaagaccc cgctgactga taaatttcca     600
gcaggtgggg aaatgatctc acagcgtacg aaaaccccta tgggccacat tggtgaaccg     660
aatgacgtgg catgggtgtg tgtgtacctg gcatctgacg aatcgaaatt tgcgacgggt     720
agcgaatttg tggtcgacgg cgggtatacc gcacagtga                            759

<210> SEQ ID NO 162
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 162

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
```

```
            65                  70                  75                  80
        Phe Gly Pro Val Thr Thr Val Asn Asn Ala Gly Ile Ser Leu Pro
                        85                  90                  95

Lys Ser Leu Glu Asp Thr Thr Thr Glu Glu Trp His Lys Leu Leu Ser
                    100                 105                 110

Val Asn Leu Asp Gly Val Phe Phe Gly Thr Arg Leu Gly Ile Arg Arg
                    115                 120                 125

Met Lys Asn Lys Gly Leu Gly Ala Ser Ile Ile Asn Met Ser Ser Ile
        130                 135                 140

Ser Gly Ile Val Gly Asp Pro Met Leu Gly Ala Tyr Asn Ala Ser Lys
        145                 150                 155                 160

Gly Ala Val Arg Ile Met Ser Lys Ser Ala Ala Leu Asp Cys Ala Val
                        165                 170                 175

Lys Asp Tyr Asp Val Arg Val Asn Thr Val His Pro Gly Ala Ile Lys
                    180                 185                 190

Thr Pro Leu Thr Asp Lys Phe Pro Ala Gly Gly Glu Met Ile Ser Gln
                    195                 200                 205

Arg Thr Lys Thr Pro Met Gly His Ile Gly Glu Pro Asn Asp Val Ala
                    210                 215                 220

Trp Val Cys Val Tyr Leu Ala Ser Asp Glu Ser Lys Phe Ala Thr Gly
        225                 230                 235                 240

Ser Glu Phe Val Val Asp Gly Gly Tyr Thr Ala Gln
                        245                 250
```

<210> SEQ ID NO 163
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 163

```
atgaccaacc gtctgaagag caaagtagcc atcgtaaccg gcgggaccca gggtatcggt      60
ttggcaatcg ccgataaatt tgtagaggag ggtgcgaaag tagttatcac cggtcgccgt     120
gcagatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggatct ctctgcctaa agcctggaa      300
gacactacca cggaggaatg gcataaactg ttgtccgtta atctggatag tgttttttc      360
ggcacccgtc tgggcattcg ccgcatgaag aataaaggct gggcgctag catcatcaat      420
atgagctcga tcagtgggat cgtaggcgat ccgatgttgg gggcatacaa cgcttccaag     480
gggcggtac gtatcatgtc gaaaagcgca gcgctggatt gcgcagtgaa ggactacgat      540
gtgcgtgtca acacagtaca tccgggcgct atcaagaccc cgctgactga taaatttcca     600
gcaggtgggg aagtgatctc acagcgtacg aaaaccccta tgggccacat tggtgaaccg     660
aatgacgtgg catggatctg tgtgtacctg gcatctgacg aatcgaaatt tgcgacgggt     720
agcgaatttg tggtcgacgg cgggtatacc gcacagtga                            759
```

<210> SEQ ID NO 164
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 164

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp His Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
130                 135                 140

Ser Gly Ile Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Val Ile Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```

<210> SEQ ID NO 165
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 165

```
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
gcagatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatct ctctgcctaa aagcctggaa   300
gacactacca cggaggaatg gcacaaactg ttgtccgtta atctggatag tgttttttc    360 ggcacccgtc tgggcattcg ccgcatgaag aataaaggct gggcgctag catcatcaat   420 atgagctcga tcagtgggat cgtaggcgat ccgatgttgg gggcatacaa cgcttccaag   480
ggggcggtac gtatcatgtc gaaagcgca gcgctggatt gcgcagtgaa ggactacgat   540
gtgcgtgtca acacagtaca tccgggcgct atcaagaccc cgctgactga taaatttcca   600
```

```
gcaggtgggg aagtgatctc acagcgtacg aaaaccccta tgggccacat tggtgaaccg    660
aatgacgtgg catgggtgtg tgtgtacctg gcatctgacg aatcgaaatt tgcgacgggt    720
agcgaatttg tggtcgacgg cgggtatacc gcacagtga                           759
```

```
<210> SEQ ID NO 166
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 166

Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp Arg Lys Leu Leu Ser
            100                 105                 110

Val Asn Leu Asp Ser Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Ile Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Phe Pro Ala Gly Gly Glu Val Ile Ser Gln
        195                 200                 205

Arg Thr Lys Thr Pro Met Gly His Ile Gly Glu Pro Asn Asp Val Ala
    210                 215                 220

Trp Val Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250

<210> SEQ ID NO 167
<211> LENGTH: 759
<212> TYPE: DNA
<213> ORGANISM: Artificial Sequence
<220> FEATURE:
<223> OTHER INFORMATION: Variant of L. kefir ketoreductase

<400> SEQUENCE: 167
atgaccaacc gtctgaagag caaagtagcc atcgtaaccg gcgggaccca gggtatcggt    60
ttggcaatcg ccgataaatt tgtagaggag ggtgcgaaag tagttatcac cggtcgccgt   120
```

```
gcagatgtag gtgaaaaggc cgccaaatca atcggcggta ctgatgttat tcgctttgtc      180
cagcacgatg tgtccgatga agcaggctgg acgaaactgt tcgacaccac cgaggaggca      240
ttcggcccgg ttacgaccgt cgtgaacaat gcagggatct ctctgcctaa aagcctggaa      300
gacactacca cggaggaatg gcataaactg ttgtccgtta atctggatgg tgttttttc       360 ggcacccgtc tgggcattcg ccgcatgaag aataaaggct gggcgctag catcatcaat       420 atgagctcga tcagtgggat cgtaggcgat ccgatgttgg gggcatacaa cgcttccaag      480
ggggcggtac gtatcatgtc gaaaagcgca gcgctggatt gcgcagtgaa ggactacgat      540
gtgcgtgtca acacagtaca tccgggcgct atcaagaccc cgctgactga taaatggcca      600
gcaggtgggg aaatgatctc acagcgtacg aaaaccccta tgggccacat tggtgaaccg      660
aatgacgtgg catgggtgtg tgtgtacctg gcatctgacg aatcgaaatt tgcgacgggt      720
agcgaatttg tggtcgacgg cgggtatacc gcacagtga                            759
```

<210> SEQ ID NO 168
<211> LENGTH: 252
<212> TYPE: PRT
<213> ORGANISM: Artificial Sequence
<220> FEATURE:
<223> OTHER INFORMATION: Variant of L. kefir ketoreductase

<400> SEQUENCE: 168

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Leu Pro
                85                  90                  95

Lys Ser Leu Glu Asp Thr Thr Thr Glu Glu Trp His Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Ser Gly Ile Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Ala Ile Lys
            180                 185                 190

Thr Pro Leu Thr Asp Lys Trp Pro Ala Gly Gly Glu Met Ile Ser Gln
        195                 200                 205

Arg Thr Lys Thr Pro Met Gly His Ile Gly Glu Pro Asn Asp Val Ala
    210                 215                 220

Trp Val Cys Val Tyr Leu Ala Ser Asp Glu Ser Lys Phe Ala Thr Gly
225                 230                 235                 240

Ser Glu Phe Val Val Asp Gly Gly Tyr Thr Ala Gln
                245                 250
```